United States Patent [19]
Chang et al.

[11] Patent Number: 5,882,644
[45] Date of Patent: Mar. 16, 1999

[54] MONOCLONAL ANTIBODIES SPECIFIC FOR THE PLATELET DERIVED GROWTH FACTOR β RECEPTOR AND METHODS OF USE THEREOF

[75] Inventors: Chung Nan Chang, Foster City; Nicholas F. Landolfi, Milpitas, both of Calif.; Ulrich Martin, München, Germany

[73] Assignees: Protein Design Labs, Inc., Mountain View, Calif.; Boehringer Mannheim GmbH, Mannheim, Germany

[21] Appl. No.: 621,751

[22] Filed: Mar. 22, 1996

[51] Int. Cl.$^6$ ................................................. A61K 39/395
[52] U.S. Cl. .................................. 424/143.1; 424/133.1; 530/387.3; 530/388.22
[58] Field of Search .................. 530/388.1, 388.15, 530/388.22, 388.25, 387.3; 427/2.25; 424/130.1, 143.1, 133.1

[56] References Cited

U.S. PATENT DOCUMENTS

| | | |
|---|---|---|
| 3,817,837 | 6/1974 | Rubenstein et al. . |
| 3,850,752 | 11/1974 | Schuurs et al. . |
| 3,939,350 | 2/1976 | Kronick et al. . |
| 3,996,345 | 12/1976 | Ullman et al. . |
| 4,275,149 | 6/1981 | Litman et al. . |
| 4,277,437 | 7/1981 | Maggio et al. . |
| 4,366,241 | 12/1982 | Tom et al. . |
| 4,683,195 | 7/1987 | Mullis et al. . |
| 4,683,202 | 7/1987 | Mullis . |
| 4,754,065 | 6/1988 | Levenson et al. . |
| 4,800,159 | 1/1989 | Mullis et al. . |
| 5,468,468 | 11/1995 | LaRochelle et al. . |
| 5,620,687 | 4/1997 | Hart et al. . |

FOREIGN PATENT DOCUMENTS

| | | |
|---|---|---|
| 0451216 | 10/1991 | European Pat. Off. . |
| WO 90/07861 | 7/1990 | WIPO . |
| WO 92/13870 | 8/1992 | WIPO . |
| WO 93/10805 | 6/1993 | WIPO . |
| WO 94/19016 | 9/1994 | WIPO . |

OTHER PUBLICATIONS

Lindmark et al (Dec. 1993) Lab. Invest. vol. 69(6):682–9.
Chaudhry et al. (Feb. 15 1992) Cancer Res. vol. 52(4):1006–12.
Claesson–Welsh, "Platelet–derived growth factor receptor signals" *J. Biol. Chem.* (1994) 269:32023–32026.
Kawahara et al., "Monoclonal antibody C3.1 is a platelet derived growth factor (PDGF) antagonist" *Biochim. Biophys. Res. Commun.* (1987) 147:839–845.
Rönnstrand et al., "Characterization of two monoclonal antibodies reactive with the external domain of the platelet-–derived growth factor receptor" *J. Biol. Chem.* (1988) 263:10429–10435.
Kanakaraj et al., "Ligand–induced interaction between α— and β–type platelet–derived growth factor (PDGF) receptors: Role of receptor heterodimers in kinase activation" *Biochem.* (1991) 30:1761–1767.

Claesson–Welsh et al., "Identification and structural analysis of the A type receptor for platelet–derived growth factor" *J. Biol. Chem.* (1989) 264:1742–1747.
Seifert et al., "Two different subunits associate to create isoform–specific platelet–derived growth factor receptors" *J. Biol. Chem.* (1989) 264:8771–8778.
Kumjian et al., "Platelet–derived growth factor (PDGF) binding promotes physical association of PDGF receptor with phospholipase C" *Proc. Natl. Acad. Sci. USA* (1989) 86:8232–8236.
Bishayee et al., "Characterization of a novel anti–peptide antibody that recognizes a specific conformation of the platelet–derived growth factor receptor" *Mol. Cell Biol.* (1988) 8:3696–3702.
Hart et al., "Synthesis, phosphorylation, and degradation of multiple forms of the platelet–derived growth factor receptor studied using a monoclonal antibody" *J. Biol. Chem.* (1987) 262:10780–10785.
Escobedo et al., "Platelet–derived growth factor receptors expressed by cDNA transfection couple to a diverse group of cellular responses associated with cell proliferation" *J. Biol. Chem.* (1988) 263:1482–1487.
Daniel et al., "Biosynthetic and glycosylation of cell surface platelet–derived growth factor receptors" *J. Biol. Chem.* (1987) 262:9778–9784.
Keating et al., "Processing of the platelet–derived growth factor receptor" *J. Biol. Chem.* (1987) 262:7932–7937.
Kazlauskas et al., "Phosphorylation of the PDGF receptor β subunit creates a tight binding site for phosphatidylinositol 3 kinase" *EMBO J.* (1990) 9:3279–3286.
Holmes et al., "Comparison of complications during percutaneous transluminal coronary angioplasty from 1977 to 1981 and from 1985 to 1986: The National Heart, Lung, and Blood Institute Percutaneous Transluminal Coronary Angioplasty Registry" *J.Amer. Coll. Cardiol.* (1988) 12:1149–1155.
Köhler et al., "Derivation of specific antibody–producing tissue culture and tumor lines by cell fusion" *Eur. J. Immunol.* (1976) 6:511–519.
Gillam et al., "Site–specific mutagenesis using synthetic oligodeoxyribonucleotide primers: I. Optimum conditions and minimum oligodeoxyribonucleotide length" *Gene* (1979) 8:81–97.
Roberts et al., "Generation of an antibody with enhanced affinity and specificity for its antigen by protein engineering" *Nature* (1987) 328:731–734.
Thorpe et al., "Monoclonal antibody–toxin conjugates: aiming the magic bullet," *Monoclonal Antibodies in Clinical Medicine*, (1982) McMichael et al., eds., Academic Press, pp. 168–190.

(List continued on next page.)

*Primary Examiner*—Christina Y. Chan
*Assistant Examiner*—Patrick Nolan
*Attorney, Agent, or Firm*—Morrison & Foerster, LLP

[57] ABSTRACT

The invention relates to monoclonal antibodies, humanized monoclonal antibodies and functional derivatives thereof specific for the platelet-derived growth factor receptor β. Methods of use of the antibody, particularly in ameliorating restenosis, are also provided.

13 Claims, 31 Drawing Sheets

OTHER PUBLICATIONS

Vitetta et al., "Redesigning nature's poisons to create anti-tumor reagents" *Science* (1987) 238:1098–1104.

Winter et al., "Man–made antibodies" *Nature* (1991) 349:293–299.

Olsnes et al., "Chimeric Toxins," *Pharmac. Ther.* (1982) 15:355–381.

Chatal et al., "Clinical prospective study with radioiodiated monoclonal antibodies directed against colorectal cancer" *Monoclonal Antibodies for Cancer Detection and Therapy* Baldwin et al. eds., (1985) Academic Press, pp. 159–180.

Jansen et al., "Efficiency and tolerance of the treatment with immuno–A–chain–toxins in human bone marrow transplantations" *Monoclonal Antibodies for Cancer Detection and Therapy* Baldwin et al., eds. (1985) Academic Press, pp. 223–248.

Myers, "The use of immuno–toxins to eliminate tumour cells from human leukemic marrow autografts" *Monoclonal Antibodies from Cancer Detection and Therapy* Baldwin et al., eds., (1985) Academic press, pp. 223–248.

Glaser et al., "Dissection of the combining site in a humanized anti–Tac antibody" *J. Immunol.* (1992) 149:2607–2614.

Tempest et al., "Reshaping a human monoclonal antibody to inhibit human respiratory syncytial virus infection in vivo" *Biotechnology* (1992) 9:266–271.

Shalaby et al., "Development of humanized bispecific antibodies reactive with cytotoxic lymphocytes and tumor cells overexpressing the HER2 protooncogene" *J. Exp. Med.* (1992) 17:217–225.

Levitt, "Molecular dynamics of native protein. I. Computer simulation of trajectories" *J. Mol. Biol.* (1983) 168:595–620.

Dohlsten et al., "Monoclonal antibody–superantigen fusion proteins: Tumor–specific agents for T–cell–based tumor therapy" *Proc. Natl. Acad. Sci. USA* (1994) 91:8945–8949.

Bird et al., "Single–chain antigen–binding proteins" *Science* (1988) 242:423–426.

Fiedler et al., "High–level production and long–term storage of engineered antibodies in transgenic tobacco seeds" *Biotechnology* (1995) 13:1090–1093.

Kanehisa, "Use of statistical criteria for screening potential homologies in nucleic acid sequences" *Nucl. Acids Res.* (1984) 12:203–213.

Cockett et al., "High level expression of tissue inhibitor of metalloproteinases in Chinese hamster ovary cells using glutamine synthetase gene amplification" *Bio/Technology* (1990) 8:662–667.

Serruys et al., "Heparin–coated Palmaz–Schatz stents in human coronary arteries. Early outcome of the Benestent–II pilot study" *Circ.* (1996) 93:412–422.

Co et al., "Chimeric and humanized antibodies with specificity for the CD33 antigen" *J. Immunol.* (1992) 148:1149–1154.

Escobedo et al., "Platelet–derived growth factor receptors expressed by cDNA transfection couple to a diverse group of cellular responses associated with cell proliferation" *J. Biol. Chem.* (1988) 263:1482–1487.

Chen et al., "High efficiency transformation of mammalian cells by plasmid DNA" *Mol. Cell. Biol.* (1987) 7:2745–2752.

Queen et al., "A humanized antibody that binds to the interleukin 2 receptor" *Proc. Natl. Acad. Sci. USA* (1989) 86:10029–10033.

Ellison et al., "Linkage and sequence homology of two human immunoglobulin γ heavy chain constant region genes" *Proc. Natl. Acad. Sci. USA* (1982) 79:1984–988.

Horgan et al., "Studies on antigen binding by intact and hinge–deleted chimeric antibodies" *J. Immunol.* (1993) 150:5400–5407.

Queen et al., "Fine mapping of an immunoglobulin gene activator" *Mol. Cell. Biol.* (1984) 4:1042–1049.

Afink et al., "Molecular cloning and functional characterization of the human platelet–derived growth factor α receptor gene promoter" *Oncogene*(1995)10:1667–1672.

Ahlman et al., "Growth regulation in carcinoid tumors" *Endocrinology and Metabolism Clinics of North America* (1993)22:889–915.

Ascoli et al., "Platelet–derived growth factor receptor immunoreactivity in mesothelioma and nonneoplastic mesothelial cells in serous effusions" *J. Clin. Cytology and Cytopathology* (1995) 39:613–622.

Bishayee, S., "A novel 200 kDa plasma membrane glycoprotein with high basal tyrosine kinase activity in tumor cells" *Indian J. Biochem. Biophy.* (1997) 34:18–24.

Böhling et al., "Expression of growth factors and growth factor receptors in capillary hemangioblastoma" *J. Neuropath. Exper. Neuro.* (1996) 55:522–527.

Chaudhry et al., "Expression of growth factor peptides and their receptors in neuroendocrine tumors of the digestive system" *Acta Oncologica* (1993) 32:107–114.

Cheng et al., "J774A. 1 macrophage cell line produces PDGF–like and non–PDGF–like growth factors for bone cells" *J. Bone Mineral Res.* (1987) 2:467–474.

Dialog Abstract of article: Deuel et al., "Human platelet-–derived growth factor. Purification and resolution into two active protein fractions" *J. Biol. Chem.* (1981) 256:8896–8899. (1 page total).

Dialog Abstract of article: Kaji, K., "Function, molecular structure and gene expression regulation of platelet–derived growth factor" *Nippon Rinsho(Japan)* (1992) 50:1902–1909. (1 page total).

Di Rocco et al., "Platelet–derived growth factor and its receptor expression in human oligodendrogliomas" *Neurosurgery* (1998) 42:341–346.

Ebert et al., "Overexpression of platelet–derived growth factor (PDGF) B chain and type β PDGF receptor in human chronic pancreatitis" *Digestive Diseases and Sciences* (1998) 43:567–574.

Fatatis et al., "Platelet–derived growth factor (PDGF)–induced $Ca^{++}$ signaling in the CG4 oligodendroglial cell line and in transformed oligodendrocytes expressing the β–PDGF receptor" *J. Biol. Chem.* (1997) 272:4351–4358.

Fellström et al., "Platelet–derived growth factor receptors in the kidney–upregulated expression in inflammation" *Kidney International* (1989) 36:1099–1102.

Heldin et al., "Binding of different dimeric forms of PDGF to human fibroblasts: evidence for two separate receptor types" *EMBO J.* (1988) 7:1387–1393.

Henriksen et al., "Expression and prognostic significance of platelet–derived growth factor and its receptors in epithelial ovarian neoplasma" *Cancer Research* (1993) 53:4550–4554.

Hermanson et al., "PDGF and its receptors following facial nerve axotomy in rats: expression in neurons and surrounding glia" *Exp. Brain* (1995) 102:415–422.

Hermanson et al., "Platelet–derived growth factor and its receptors inhuman glioma tissue: Expression of messenger RNA and protein suggests the presence of autocrine and paracrine loops" *Cancer Research* (1992) 52:3213–3219.

Hogg et al., "Interaction of platelet–derived growth factor with thrombospondin–1" *J. Biochem.* (1997) 326:709–716.

Hsu et al., "Platelet–derived growth factor–B increases colon cancer cell growth in vivo by a paracrine effect" *J. Cell. Phys.* (1995) 165:239–245.

Huang et al., "Human platelet–derived growth factor: Radioimmunoassay and discovery of a specific plasma–binding protein" *J. Cell Bio.* (1983) 97:383–388.

Kawai et al., "Expression in lung carcinomas of platelet––derived growth factor and its receptors" *Laboratory Investigation* (1997) 77:431–436.

Kee et al., "Receptor protein tyrosine kinases in perinatal developing rat kidney" *Kidney International* (1997) 52:309–317.

Kenagy et al., "Primate smooth muscle cell migration from aortic explants is mediated by endogenous platelet–derived growth factor and basic fibroblast growth factor acting through matrix metalloproteinases 2 and 9" *Basic Science Reports* (1997) 96:3555–3560.

Kim et al., "Transforming growth factor β1–induced delay of cell cycle progression and its association with growth–related gene expression in mouse fibroblasts" *Cancer Letters* (1993) 71:125–132.

Kovalenko et al., "Phosphorylation site–specific inhibition of platelet–derived growth factor β–receptor autophosphorylation by the receptor blocking Tyrophostin AG1296" *Biochem.* (1997) 36:6260–6269.

Krupinski et al., "A putative role for platelet–derived growth factor in angiogenesis and neuroprotection after ischemic stroke in humans" *Stroke* (1997) 28:564–573.

Lindmark et al., "Stromal expression of platelet–derived growth factor β–receptor and platelet–derived growth factor B–chain in colorectal cancer" *Laboratory Investigation* (1993) 69:682–689.

Lindroos et al., "Alveolar Macrophages stimulated with titanium dioxide, chrysotile asbestos . . . " *Resp. Cell Mol. Bio.* (1997) 16:283–292.

Lokker et al., "Functional importance of platelet–derived growth factor (PDGF) receptor extracellular immunoglobulin–like domains: Identification of PDGF binding site . . . " *J. Biol. Chem.* (1997) 272:33037–33044.

Marra et al., "Phosphatidylinositol 3–kinase is required for platelet–derived growth factor's actions on hepatic stellate cells" *Gastroenterology* (1997) 112:1297–1306.

Medline GenBank Accession # 452901 created from original journal article: Rorsman et al. "Characterization of the mouse PDGF A–chain gene. Evolutionary conservation of gene structure, nucleotide sequence and alternative splicing" *Growth Factors* (1992) 6:303–313. (2 pages total).

Medline GenBank Accession # 206058 created from original journal articles: Katayose et al., "Expression of platelet––derived growth factor (PDGF)–A and –B chains . . . " unpublished and Pollock et al., Investigations into the function . . . Theses–University College of London, London, England (1992) pp. 105–121. (1 page total).

Medline GenBank Accession # 2135935 created from original journal article: Cook et al., "Purification and analysis of proteinase–resistant mutants . . . " *J. Biochem.* (1992) 281:57–65. (1 page total).

Medline GenBank Accession # 35377 created from original journal article: Cook et al., "Purification and analysis of proteinase–resistant mutants . . . " *J. Biochem.* (1992) 281:57–65. (1 page total).

Mitchell et al., "Thrombin–stimulated immunoprecipitation of phosphatidylinositol 3–kinase from human platelets" *Proc. Natl. Acad. Sci. USA* (1990) 87:9396–9400.

Murlas et al., "Interleukin–1β increases airway epithelial cell mitogenesis partly by stimulating endothelin–1 production" *Lung* (1997) 175:117–126.

Naito et al., "Clinical assessment of the significance of platelet–derived growth factor in patients with immunoglobulin A nephropathy" *Lab. Clin. Med.* (1997) 130:63–68.

Ohshiro et al., "Increased insulin–like growth factor and platelet–derived growth factor system in the pyloric muscle in infantile hypertrophic pyloric stenosis" *J. Ped. Surg.* (1998) 33:378–381.

Pontén et al., "Epithelial–stromal interactions in basal cell cancer: The PDGF system" *Soc. Invest. Derm.* (1994) 102:304–309.

Rubin et al., "Expression of platelet–derived growth factor receptors is induced on connective tissue cells during chronic synovial inflammation" *Scand. J. Immunol.* (1988) 27:285–294.

Rubin et al., "Induction of B–type receptors for platelet––derived growth factor in vascular inflammation: Possible implications for development of vascular proliferation lesions" *Lancet* (1988) 1:1353–1356.

Senior et al., "Chemotactic activity of platelet alpha granule proteins for fibroblasts" *J. Cell Bio.* (1983) 96:382–385.

Shamah et al., "Detection of activated platelet–derived growth factor receptors in human meningioma" *Cancer Res.* (1997) 57:4141–4147.

Shulman et al., "An antibody reactive with domain 4 of the platelet–derived growth factor β receptor allows BB binding while inhibiting proliferation by impairing receptor dimerization" *J. Biol. Chem.* (1997) 272:17400–17404.

Sjöborg et al., "Expression of platelet–derived growth factor after intrastriatal ibotenic acid injury" *Exp. Brain Res.* (1998) 119:245–250.

Spacey et al., "Indolocarbazoles: Potent and selective inhibitors of platelet–derived growth factor receptor autophosphorylation" *Biochemical Pharmacology* (1998) 55:261–271.

Sundberg et al., "Tumor cell and connective tissue cell interactions in human colorectal adenocarcinoma: Transfer of platelet–derived growth factor–AB/BB to stromal cells" *Amer. J. Path* (1997) 151:479–492.

Terracio et al., "Induction of platelet–derived growth factor receptor expression in smooth muscle cells and fibroblasts upon tissue culturing" *J. Cell Bio.* (1988) 107:1947–1957.

Tingström et al., "Expression of platelet–derived growth factor–β receptors on human fibroblasts: Regulation by recombinant platelet–derived growth factor–BB, IL–1, and tumor necrosis factor–α" *J. Immunol.* (1992) 148:546–554.

Vassbotn et al., "A monoclonal antibody against PDGF B–chain inhibits PDGF–induced DNA synthesis in C3H fibroblasts and prevents binding of PDGF to its receptor" *Biochimica et Biophysica Acta.* (1990) 1054:246–249.

Vassbotn et al., "Neomycin is a platelet–derived growth factor (PDGF) antagonist that allows discrimination of PDGF α– and β–receptor signals in cells expressing both receptor types" *J. Biol. Chem.* (1992) 267:15635–15641.

Vernon et al., "Endothelial cell–conditioned medium down regulates smooth muscle contractile protein expression" *American Physiol. Soc.* (1997) 272:C582–C591.

Vinik et al., "Role of growth factors in pancreatic endocrine cells: Growth and differentiation" *Endocrin. Metabol. Clinics North America* (1993) 22:875–887.

Wakikawa et al., "Thrombopoietin inhibits in vitro osteoclastogenesis from murine bone marrow cells" *Endocrin.* (1997) 138:4160–4166.

Wang et al., "Cell proliferation in human soft tissue tumors correlates with platelet–derived growth factor B chain expression: An immunohistochemical and in situ hybridization study" *Cancer Res.* (1994) 54:560–564.

Yeh et al., "Ultrastructural localization of a platelet–derived growth factor/v–cis–related protein(s) in cytoplasm and nucleus of simian sarcoma virus–transformed cells" *Proc. Natl. Acad. Sci. USA* (1987) 84:2317–2321.

Zubiaur et al., "A small GTP–binding protein, Rho, associates with the platelet–derived growth factor type–β receptor upon ligand binding" *J. Biol. Chem.* (1995) 270:17221–17228.

González–Rubio et al., "Oxidative stress induces tyrosine phosphorylation of PDGF α– and β–receptors and pp60$^{c-src}$ in mesangial cells" *Kidney International* (1996) 50:164–173.

Krane et al., "Increased dermal expression of platelet––derived growth factor receptors in growth–activated skin wounds and psoriasis" *J. Invest. Dermatol.* (1991) 96:983–986.

Shulman et al., "An antibody reactive with domain 4 of the platelet–derived growth factor beta receptor allows BB binding while inhibiting proliferation by impairing receptor dimerization" *J. Biol. Chem.* (1997) 272(28):17400–17404.

SEQ ID NO:1

```
ATGAGGGTCC TTGCTGAGCT CCTGGGGCTG CTGCTGTTCT GCTTTTTAGG TGTGAGATGT    60
GACATCCAGA TGAACCAGTC TCCATCCAGT CTGTCTGCAT CCCTTGGAGA CACAATTACC   120
ATCACTTGCC ATGCCAGTCA GAACATTAAT GTTTGGTTAA GCTGGTACCA GCGGAAACCA   180
GGAAATATTC CTAAACTATT GATCTATAAG GCTTCCAACC TGCACACAGG CGTCCCTTCA   240
AGGTTTAGTG GCAGTGGATC TGGTACAGGT TTCACATTAA CCATCAGCAG CCTGCAGCCT   300
GAAGACATTG CCACCTACTA CTGTCAACAG GGTCAAAGTT TTCCATTCAC GTTCGGCTCG   360
GGGACAAAGT TGGAAATAAA A                                            381
```

FIG. 1A

SEQ ID NO:2

| | | | | | | | | | | | | | | | | | | | | |
|---|---|---|---|---|---|---|---|---|---|---|---|---|---|---|---|---|---|---|---|---|
| M | R | V | L | A | E | L | L | G | L | L | L | F | C | F | L | G | V | R | C | 20 |
| D | I | Q | M | N | Q | S | P | S | S | L | S | A | S | L | G | D | T | I | T | 40 |
| I | T | C | H | A | S | Q | N | I | N | V | W | L | S | W | Y | Q | R | K | P | 60 |
| G | N | I | P | K | L | L | I | Y | K | A | S | N | L | H | T | G | V | P | S | 80 |
| R | F | S | G | S | G | S | G | T | G | F | T | L | T | I | S | S | L | Q | P | 100 |
| E | D | I | A | T | Y | Y | C | Q | Q | G | Q | S | F | P | F | T | F | G | S | 120 |
| G | T | K | L | E | I | K | | | | | | | | | | | | | | 127 |

FIG. 1B

SEQ ID NO:3

| | | | | | | |
|---|---|---|---|---|---|---|
| ATGGCTGTCC | TGGCGCTACT | CCTCTGCCTG | GTGACTTTCC | CAAGCTGTGC | CCTGTCCCAG | 60 |
| GTGCAGCTGA | AGGAGTCAGG | ACCTGGCCTG | GTGGCGCCCT | CACAGAGCCT | GTCCATCACA | 120 |
| TGCACTGTCT | CTGGGTTCTC | ATTAACCAAC | TATGCTATAA | ACTGGGTTCG | CCAGCCACCA | 180 |
| GGACAGGGTC | TGGAGTGGCT | TGGAATAATA | TGGACTGGTG | GAGGCACAAG | TTATAATTCT | 240 |
| GCTCTCAAAT | CCAGACTGAG | CATCAGCAAA | GACAACTCCA | AGAGTCAAGT | TTTCTTAAAA | 300 |
| ATGAACAGTC | TACAAACTGA | TGACACAGCC | AGGTATTACT | GTGCCAGAAC | TGGGACGAGG | 360 |
| GGATATTTCT | TTGACTACTG | GGGCCAAGGC | ACCACTCTCA | CAGTCTCCTC | A | 411 |

FIG. 1C

SEQ ID NO:4

| M | A | V | L | A | L | L | C | L | V | T | F | P | S | C | A | L | S | Q | | 20 |
| V | Q | L | K | E | S | G | P | G | L | V | A | P | S | Q | S | L | S | I | T | 40 |
| C | T | V | S | G | F | S | L | T | <u>N</u> | <u>Y</u> | <u>A</u> | <u>I</u> | <u>N</u> | W | V | R | Q | P | P | 60 |
| G | Q | G | L | E | W | L | G | <u>I</u> | <u>I</u> | <u>W</u> | <u>T</u> | <u>G</u> | <u>G</u> | <u>T</u> | <u>S</u> | <u>Y</u> | <u>N</u> | <u>S</u> | | 80 |
| <u>A</u> | <u>L</u> | <u>K</u> | <u>S</u> | R | L | S | I | S | K | D | N | S | K | S | Q | V | F | L | K | 100 |
| M | N | S | L | Q | T | D | D | T | A | R | Y | Y | C | A | R | <u>T</u> | G | <u>T</u> | <u>R</u> | 120 |
| <u>G</u> | <u>Y</u> | <u>F</u> | <u>F</u> | <u>D</u> | <u>Y</u> | W | G | Q | G | T | T | L | T | V | S | S | | | | 137 |

FIG. 1D

SEQ ID NO:5

ATGAGGGTCC TTGCTGAGCT CCTGGGGCTG CTGCTGTTCT GCTTTTTAGG TGTGAGATGT 60
GACATCCAGA TGACCCAGTC TCCATCCTCC CTGTCTGCTT CTGTAGGAGA CAGAGTCACC 120
ATCACTTGCC ATGCCAGTCA GAACATTAAT GTTTGGTTAA GCTGGTATCA GCAAAAACCA 180
GGGAAAGCCC CTAAGCTCCT GATCTACAAG GCTTCCAACC TGCACACAGG GGTCCCATCA 240
AGGTTCAGTG GAAGTGGATC TGGGACAGGT TTCACTTTAA CCATCAGCAG CCTGCAGCCT 300
GAAGATATTG CAACATATTA CTGTCAACAG GGTCAAAGTT TTCCATTCAC GTTCGGCGGA 360
GGGACCAAGG TGGAGATCAA A 381

FIG. 2A

SEQ ID NO:6

| | | | | | | | | | | | | | | | | | | | | |
|---|---|---|---|---|---|---|---|---|---|---|---|---|---|---|---|---|---|---|---|---|
| M | R | V | L | A | E | L | L | G | L | L | L | F | C | F | L | G | V | R | C | 20 |
| D | I | Q | M | T | Q | S | P | S | S | L | S | A | S | V | G | D | R | V | T | 40 |
| I | T | C | H | A | S | Q | N | I | N | V | W | L | S | W | Y | Q | Q | K | P | 60 |
| G | K | A | P | K | L | L | I | Y | K | A | S | N | L | H | T | G | V | P | S | 80 |
| R | F | S | G | S | G | S | G | T | G | F | T | L | T | I | S | S | L | Q | P | 100 |
| E | D | I | A | T | Y | Y | C | Q | Q | G | Q | S | F | P | F | T | F | G | G | 120 |
| G | T | K | V | E | I | K | | | | | | | | | | | | | | 127 |

FIG. 2B

SEQ ID NO:7

| | | | | | |
|---|---|---|---|---|---|
| ATGGCTGTCC | TGGCGCTACT | CCTCTGCCTG | GTGACTTTCC | CAAGCTGTGC | CCTGTCCCAG | 60
| GTGCAGCTGC | AGGAGTCGGG | CCCAGGACTG | GTGAAGCCTT | CGGAGACCCT | GTCCCTCACC | 120
| TGCACTGTCT | CTGGTTTCTC | CTTAACCAAC | TATGCTATAA | ACTGGGTTCG | GCAGCCACCA | 180
| GGGAAGGGAC | TGGAGTGGCT | TGGGATAATA | TGGACTGGTG | GAGGCACAAG | TTATAATTCT | 240
| GCTCTCAAAT | CCCGACTGAC | CATATCAAAA | GACACTTCCA | AGAACCAGGT | TTCCCTGAAG | 300
| CTGAGCTCTG | TTACCGCTGC | GGACACGGCC | GTGTATTACT | GTGCGAGAAC | TGGGACGAGG | 360
| GGATATTTCT | TTGACTACTG | GGGCCAGGGA | ACCCTGGTCA | CCGTCTCCTC | A | 411

FIG. 2C

SEQ ID NO:8

| | | | | | | | | | | | | | | | | | | | | |
|---|---|---|---|---|---|---|---|---|---|---|---|---|---|---|---|---|---|---|---|---|
| M | A | V | L | A | L | L | L | C | L | V | T | F | P | S | C | A | L | S | <u>Q</u> | 20 |
| V | Q | L | Q | E | S | G | P | G | L | V | K | P | S | E | T | L | S | L | T | 40 |
| C | T | V | S | G | F | S | L | T | <u>N</u> | <u>Y</u> | <u>A</u> | <u>I</u> | <u>N</u> | W | V | R | Q | P | P | 60 |
| G | K | G | L | E | W | L | G | <u>I</u> | <u>I</u> | <u>W</u> | <u>T</u> | <u>G</u> | <u>G</u> | <u>G</u> | <u>T</u> | <u>S</u> | <u>Y</u> | <u>N</u> | <u>S</u> | 80 |
| <u>A</u> | <u>L</u> | <u>K</u> | <u>S</u> | R | L | T | I | S | K | D | T | S | K | N | Q | V | S | L | K | 100 |
| L | S | S | V | T | A | A | D | T | A | V | Y | Y | C | A | R | <u>T</u> | <u>G</u> | <u>T</u> | <u>R</u> | 120 |
| <u>G</u> | <u>Y</u> | <u>F</u> | <u>F</u> | <u>D</u> | <u>Y</u> | W | G | Q | G | T | L | V | T | V | S | S | | | | 137 |

FIG. 2D

SEQ ID NO:9

| | | | | | |
|---|---|---|---|---|---|
| ATGGAGACAG | AAACACTCCT | GCTATGGGTG | CTGCTGCTCT | GGGTTCCAGG | TTCCACAGGT | 60
| GACATTGTGC | TGACCCAATC | TCCACCTTCT | TTGGCTGTGT | CTCTAGGGCA | GAGGGCCACC | 120
| ATATCCTGCA | GAGCCAGTGA | AAGTGTTGAT | AGTTATGGCA | ATAGTTTTAT | GCACTGGTAC | 180
| CAGCAGAAAC | CAGGACAGCC | ACCCAAACTC | CTCATCTATC | GTGCATCCAA | CCTAGAATCT | 240
| GGGATCCCTG | CCAGGTTCAG | TGGCGGTGGG | TCTAGGACAG | ACTTCACCCT | CACCATTAAT | 300
| CCTGTGGAGG | CTGATGATGT | TGCAACCTAT | TACTGTCAAC | AAAGTAATGA | GGATCCTCCG | 360
| ACGTTCGGTG | GAGGCACCAA | GCTGGAAATC | AAA | | | 393

FIG. 7A

SEQ ID NO:10

| | | | | | | | | | | | | | | | | | | | | |
|---|---|---|---|---|---|---|---|---|---|---|---|---|---|---|---|---|---|---|---|---|
| M | E | T | E | T | L | L | W | V | L | L | L | W | V | P | G | S | T | G | | 20 |
| D | I | V | L | T | Q | S | P | P | S | L | A | V | S | L | G | Q | R | A | T | 40 |
| I | S | C | R | A | S | E | S | V | D | S | Y | G | N | S | F | M | H | W | Y | 60 |
| Q | Q | K | P | G | Q | P | P | K | L | L | I | Y | R | A | S | N | L | E | S | 80 |
| G | I | P | A | R | F | S | G | G | G | S | R | T | D | F | T | L | T | I | N | 100 |
| P | V | E | A | D | D | V | A | T | Y | Y | C | Q | Q | S | N | E | D | P | P | 120 |
| T | F | G | G | G | T | K | L | E | I | K | | | | | | | | | | 131 |

FIG. 7B

SEQ ID NO:11

| | | | | | |
|---|---|---|---|---|---|
| ATGGAAAGGC | ACTGGATCTT | TCTCTTCCTG | TTTTCAGTAA | CTGCAGGTGT | CCACTCCCAG | 60
| GTCCAGCTTC | AGCAGTCTGG | GGCTGAAGTG | GCAAAACCTG | GGGCCTCAGT | GAAGATGTCC | 120
| TGCAAGGCTT | CTGGCTACAC | CTTTACTAAC | TGCTGGATGC | ACTGGGTAAA | ACAGAGGCCT | 180
| GGACAGGGTC | TGGAATGGAT | TGGATACATT | AATCCTACCA | CTGGTTATTC | TGAGTACAAT | 240
| CAGAACTTCA | AGGACAAGGC | CACATTGACT | GCAGACAAAT | CCTCCAACAC | AGCCTACATT | 300
| CAACTGAGTA | GCCTGACATC | TGAGGACTCT | GCAGTCTATT | ACTGTACAAG | CAACTATGGT | 360
| CACTACGACT | GGTTTGCTAA | CTGGGGCCAA | GGGACTCTGG | TCACT | | 405

FIG. 7C

SEQ ID NO:12

SEQ ID NO:13

| | | | | | | |
|---|---|---|---|---|---|---|
| ATGGAGACCG | ATACCCTCCT | GCTATGGGTC | CTCCTGCTAT | GGGTCCCAGG | ATCAACCGGA | 60 |
| GACATCCAGA | TGACCCAGTC | TCCATCCTCC | CTGTCTGCTA | GCGTAGGAGA | CAGGGTCACC | 120 |
| ATCACTTGCA | GAGCCAGTGA | AAGTGTTGAT | AGTTATGGCA | ATAGTTTTAT | GCACTGGTAC | 180 |
| CAGCAGAAAC | CAGGGAAAGC | TCCTAAGCTC | CTGATCTATC | GTGCATCCAA | CCTAGAATCT | 240 |
| GGAATCCCAT | CTCGGTTCAG | TGGCAGTGGA | TCTAGGACAG | ATTTCACTCT | CACCATCAGC | 300 |
| AGCCTGCAGC | CTGAAGATGT | TGCAACTTAT | TACTGTCAAC | AAAGTAATGA | GGACCCTCCG | 360 |
| ACGTTCGGTC | AAGGGACCAA | GGTGGAAATC | AAA | | | 393 |

FIG. 8A

SEQ ID NO:14

| | | | | | | | | | | | | | | | | | | | | |
|---|---|---|---|---|---|---|---|---|---|---|---|---|---|---|---|---|---|---|---|---|
| M | E | T | D | T | L | L | L | W | V | L | L | L | W | V | P | G | S | T | G | 20 |
| <u>D</u> | I | Q | M | T | Q | S | P | S | S | L | S | A | S | V | G | D | R | V | T | 40 |
| I | T | C | <u>R</u> | <u>A</u> | <u>S</u> | <u>E</u> | <u>S</u> | <u>V</u> | <u>D</u> | <u>S</u> | <u>Y</u> | <u>G</u> | <u>N</u> | <u>S</u> | <u>F</u> | <u>M</u> | <u>H</u> | W | Y | 60 |
| Q | Q | K | P | G | K | A | P | K | L | L | I | Y | <u>R</u> | <u>A</u> | <u>S</u> | <u>N</u> | <u>L</u> | <u>E</u> | <u>S</u> | 80 |
| G | I | P | S | R | F | S | G | S | G | S | R | T | D | F | T | L | T | I | S | 100 |
| S | L | Q | P | E | D | V | A | T | Y | Y | C | <u>Q</u> | <u>Q</u> | <u>S</u> | <u>N</u> | <u>E</u> | <u>D</u> | <u>P</u> | <u>P</u> | 120 |
| <u>T</u> | F | G | Q | G | T | K | V | E | I | K | | | | | | | | | | 131 |

FIG. 8B

SEQ ID NO:15

| | | | | | | |
|---|---|---|---|---|---|---|
| ATGGGATGGA | GCTGGATCTT | TCTCTTCCTC | CTGTCAGGTA | CCGCGGGGCGT | GCACTCTCAG | 60 |
| GTGCAGCTGG | TGCAGTCTGG | GGCTGAGGTG | AAGAAGCCTG | GCGCCCTCGGT | AAAGGTCTCC | 120 |
| TGCAAGGCTT | CTGGATACAC | CTTCACTAAC | TGCTGGATGC | ATTGGGTGCG | ACAGGCCCCT | 180 |
| GGACAAGGGC | TTGAGTGGAT | TGGATACATT | AATCCTACCA | CTGGTTATTC | TGAGTACAAT | 240 |
| CAGAAACTTCA | AGGACAAGGC | CACGATTACC | GCGGACAAAT | CCACGAGCAC | AGCCTACATG | 300 |
| GAGCTGAGCA | GCCTGAGATC | TGAGGACACG | GCCGTGTATT | ACTGTACAAG | CAACTATGGT | 360 |
| CACTACGACT | GGTTTGCTAA | CTGGGGCCAG | GGAACCCCTGG | TCACA | | 405 |

FIG. 8C

SEQ ID NO:16

| | | | | | | | | | | | | | | | |  |
|---|---|---|---|---|---|---|---|---|---|---|---|---|---|---|---|---|
| M | G | W | S | W | I | F | L | F | L | L | S | G | T | A | G | V | H | S | <u>Q</u> | 20 |

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..381

( i x ) FEATURE:
        ( A ) NAME/KEY: mat_peptide
        ( B ) LOCATION: 61..381

( i x ) FEATURE:
        ( A ) NAME/KEY: misc_feature
        ( B ) LOCATION: group(130..162, 208..228, 325..351)
        ( D ) OTHER INFORMATION: /note= "Complementarity Determining
            Regions(CDR- 1, CDR-2 and CDR-3)"

( x i ) SEQUENCE DESCRIPTION: SEQ ID NO:1:

```
ATG  AGG  GTC  CTT  GCT  GAG  CTC  CTG  GGG  CTG  CTG  CTG  TTC  TGC  TTT  TTA      48
GGT  GTG  AGA  TGT  GAC  ATC  CAG  ATG  AAC  CAG  TCT  CCA  TCC  AGT  CTG  TCT      96
GCA  TCC  CTT  GGA  GAC  ACA  ATT  ACC  ATC  ACT  TGC  CAT  GCC  AGT  CAG  AAC     144
ATT  AAT  GTT  TGG  TTA  AGC  TGG  TAC  CAG  CGG  AAA  CCA  GGA  AAT  ATT  CCT     192
AAA  CTA  TTG  ATC  TAT  AAG  GCT  TCC  AAC  CTG  CAC  ACA  GGC  GTC  CCT  TCA     240
AGG  TTT  AGT  GGC  AGT  GGA  TCT  GGT  ACA  GGT  TTC  ACA  TTA  ACC  ATC  AGC     288
AGC  CTG  CAG  CCT  GAA  GAC  ATT  GCC  ACC  TAC  TAC  TGT  CAA  CAG  GGT  CAA     336
AGT  TTT  CCA  TTC  ACG  TTC  GGC  TCG  GGG  ACA  AAG  TTG  GAA  ATA  AAA          381
```

( 2 ) INFORMATION FOR SEQ ID NO:2:

( i ) SEQUENCE CHARACTERISTICS:
        ( A ) LENGTH: 127 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Arg  Val  Leu  Ala  Glu  Leu  Leu  Gly  Leu  Leu  Leu  Phe  Cys  Phe  Leu
 1              5                        10                       15
Gly  Val  Arg  Cys  Asp  Ile  Gln  Met  Asn  Gln  Ser  Pro  Ser  Ser  Leu  Ser
              20                       25                       30
Ala  Ser  Leu  Gly  Asp  Thr  Ile  Thr  Ile  Thr  Cys  His  Ala  Ser  Gln  Asn
         35                       40                       45
Ile  Asn  Val  Trp  Leu  Ser  Trp  Tyr  Gln  Arg  Lys  Pro  Gly  Asn  Ile  Pro
     50                       55                       60
Lys  Leu  Leu  Ile  Tyr  Lys  Ala  Ser  Asn  Leu  His  Thr  Gly  Val  Pro  Ser
65                       70                       75                       80
Arg  Phe  Ser  Gly  Ser  Gly  Ser  Gly  Thr  Gly  Phe  Thr  Leu  Thr  Ile  Ser
              85                       90                       95
Ser  Leu  Gln  Pro  Glu  Asp  Ile  Ala  Thr  Tyr  Tyr  Cys  Gln  Gln  Gly  Gln
            100                      105                      110
```

Ser Phe Pro Phe Thr Phe Gly Ser Gly Thr Lys Leu Glu Ile Lys
            115                     120                     125

(2) INFORMATION FOR SEQ ID NO:3:

(i) SEQUENCE CHARACTERISTICS:
        (A) LENGTH: 411 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..411

(ix) FEATURE:
        (A) NAME/KEY: mat_peptide
        (B) LOCATION: 58..411

(ix) FEATURE:
        (A) NAME/KEY: misc_feature
        (B) LOCATION: group(148..152, 205..252, 349..378)
        (D) OTHER INFORMATION: /note= "Complementarity Determining
            Regions(CDR-1, CDR-2 and CDR-3)"

(xi) SEQUENCE DESCRIPTION: SEQ ID NO:3:

```
ATG GCT GTC CTG GCG CTA CTC CTC TGC CTG GTG ACT TTC CCA AGC TGT      48
GCC CTG TCC CAG GTG CAG CTG AAG GAG TCA GGA CCT GGC CTG GTG GCG      96
CCC TCA CAG AGC CTG TCC ATC ACA TGC ACT GTC TCT GGG TTC TCA TTA     144
ACC AAC TAT GCT ATA AAC TGG GTT CGC CAG CCA CCA GGA CAG GGT CTG     192
GAG TGG CTT GGA ATA ATA TGG ACT GGT GGA GGC ACA AGT TAT AAT TCT     240
GCT CTC AAA TCC AGA CTG AGC ATC AGC AAA GAC AAC TCC AAG AGT CAA     288
GTT TTC TTA AAA ATG AAC AGT CTA CAA ACT GAT GAC ACA GCC AGG TAT     336
TAC TGT GCC AGA ACT GGG ACG AGG GGA TAT TTC TTT GAC TAC TGG GGC     384
CAA GGC ACC ACT CTC ACA GTC TCC TCA                                 411
```

(2) INFORMATION FOR SEQ ID NO:4:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Val Leu Ala Leu Leu Leu Cys Leu Val Thr Phe Pro Ser Cys
 1               5                  10                  15

Ala Leu Ser Gln Val Gln Leu Lys Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Thr Asn Tyr Ala Ile Asn Trp Val Arg Gln Pro Pro Gly Gln Gly Leu
        50                  55                  60

Glu Trp Leu Gly Ile Ile Trp Thr Gly Gly Gly Thr Ser Tyr Asn Ser
 65                  70                  75                  80

Ala Leu Lys Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Arg Tyr
            100                 105                 110

```
Tyr  Cys  Ala  Arg  Thr  Gly  Thr  Arg  Gly  Tyr  Phe  Phe  Asp  Tyr  Trp  Gly
          115                      120                      125

Gln  Gly  Thr  Thr  Leu  Thr  Val  Ser  Ser
          130                 135
```

( 2 ) INFORMATION FOR SEQ ID NO:5:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..381

( i x ) FEATURE:
        ( A ) NAME/KEY: mat_peptide
        ( B ) LOCATION: 61..381

( i x ) FEATURE:
        ( A ) NAME/KEY: misc_feature
        ( B ) LOCATION: group(130..162, 208..228, 325..351)
        ( D ) OTHER INFORMATION: /note= "Complementarity Determining
              Regions(CDR- 1, CDR-2 and CDR-3)"

( x i ) SEQUENCE DESCRIPTION: SEQ ID NO:5:

```
ATG  AGG  GTC  CTT  GCT  GAG  CTC  CTG  GGG  CTG  CTG  CTG  TTC  TGC  TTT  TTA       48
GGT  GTG  AGA  TGT  GAC  ATC  CAG  ATG  ACC  CAG  TCT  CCA  TCC  TCC  CTG  TCT       96
GCT  TCT  GTA  GGA  GAC  AGA  GTC  ACC  ATC  ACT  TGC  CAT  GCC  AGT  CAG  AAC      144
ATT  AAT  GTT  TGG  TTA  AGC  TGG  TAT  CAG  CAA  AAA  CCA  GGG  AAA  GCC  CCT      192
AAG  CTC  CTG  ATC  TAC  AAG  GCT  TCC  AAC  CTG  CAC  ACA  GGG  GTC  CCA  TCA      240
AGG  TTC  AGT  GGA  AGT  GGA  TCT  GGG  ACA  GGT  TTC  ACT  TTA  ACC  ATC  AGC      288
AGC  CTG  CAG  CCT  GAA  GAT  ATT  GCA  ACA  TAT  TAC  TGT  CAA  CAG  GGT  CAA      336
AGT  TTT  CCA  TTC  ACG  TTC  GGC  GGA  GGG  ACC  AAG  GTG  GAG  ATC  AAA           381
```

( 2 ) INFORMATION FOR SEQ ID NO:6:

( i ) SEQUENCE CHARACTERISTICS:
        ( A ) LENGTH: 127 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Arg  Val  Leu  Ala  Glu  Leu  Leu  Gly  Leu  Leu  Leu  Phe  Cys  Phe  Leu
 1                   5                        10                      15

Gly  Val  Arg  Cys  Asp  Ile  Gln  Met  Thr  Gln  Ser  Pro  Ser  Ser  Leu  Ser
               20                      25                      30

Ala  Ser  Val  Gly  Asp  Arg  Val  Thr  Ile  Thr  Cys  His  Ala  Ser  Gln  Asn
          35                      40                      45

Ile  Asn  Val  Trp  Leu  Ser  Trp  Tyr  Gln  Gln  Lys  Pro  Gly  Lys  Ala  Pro
     50                      55                      60

Lys  Leu  Leu  Ile  Tyr  Lys  Ala  Ser  Asn  Leu  His  Thr  Gly  Val  Pro  Ser
65                  70                      75                           80

Arg  Phe  Ser  Gly  Ser  Gly  Ser  Gly  Thr  Gly  Phe  Thr  Leu  Thr  Ile  Ser
                    85                      90                      95

Ser  Leu  Gln  Pro  Glu  Asp  Ile  Ala  Thr  Tyr  Tyr  Cys  Gln  Gln  Gly  Gln
               100                     105                     110
```

```
Ser  Phe  Pro  Phe  Thr  Phe  Gly  Gly  Gly  Thr  Lys  Val  Glu  Ile  Lys
          115                 120                      125
```

(2) INFORMATION FOR SEQ ID NO:7:

(i) SEQUENCE CHARACTERISTICS:
  (A) LENGTH: 411 base pairs
  (B) TYPE: nucleic acid
  (C) STRANDEDNESS: double
  (D) TOPOLOGY: linear (ix) FEATURE:
  (A) NAME/KEY: CDS
  (B) LOCATION: 1..411

(ix) FEATURE:
  (A) NAME/KEY: mat_peptide
  (B) LOCATION: 58..411

(ix) FEATURE:
  (A) NAME/KEY: misc_feature
  (B) LOCATION: group(147..162, 205..252, 349..378)
  (D) OTHER INFORMATION: /note= "Complementarity Determining
   Regions(CDR- 1, CDR-2 and CDR-3)"

(xi) SEQUENCE DESCRIPTION: SEQ ID NO:7:

```
ATG  GCT  GTC  CTG  GCG  CTA  CTC  CTC  TGC  CTG  GTG  ACT  TTC  CCA  AGC  TGT     48
GCC  CTG  TCC  CAG  GTC  CAG  CTG  CAG  GAG  TCG  GGC  CCA  GGA  CTG  GTG  AAG     96
CCT  TCG  GAG  ACC  CTG  TCC  CTC  ACC  TGC  ACT  GTC  TCT  GGT  TTC  TCC  TTA    144
ACC  AAC  TAT  GCT  ATA  AAC  TGG  GTT  CGG  CAG  CCA  CCA  GGG  AAG  GGA  CTG    192
GAG  TGG  CTT  GGG  ATA  ATA  TGG  ACT  GGT  GGA  GGC  ACA  AGT  TAT  AAT  TCT    240
GCT  CTC  AAA  TCC  CGA  CTG  ACC  ATA  TCA  AAA  GAC  ACT  TCC  AAG  AAC  CAG    288
GTT  TCC  CTG  AAG  CTG  AGC  TCT  GTT  ACC  GCT  GCG  GAC  ACG  GCC  GTG  TAT    336
TAC  TGT  GCG  AGA  ACT  GGG  ACG  AGG  GGA  TAT  TTC  TTT  GAC  TAC  TGG  GGC    384
CAG  GGA  ACC  CTG  GTC  ACC  GTC  TCC  TCA                                        411
```

(2) INFORMATION FOR SEQ ID NO:8:

(i) SEQUENCE CHARACTERISTICS:
  (A) LENGTH: 137 amino acids
  (B) TYPE: amino acid
  (D) TOPOLOGY: linear (ii) MOLECULE TYPE: protein (xi) SEQUENCE DESCRIPTION: SEQ ID NO:8:

```
Met  Ala  Val  Leu  Ala  Leu  Leu  Leu  Cys  Leu  Val  Thr  Phe  Pro  Ser  Cys
 1              5                        10                       15
Ala  Leu  Ser  Gln  Val  Gln  Leu  Gln  Glu  Ser  Gly  Pro  Gly  Leu  Val  Lys
               20                       25                  30
Pro  Ser  Glu  Thr  Leu  Ser  Leu  Thr  Cys  Thr  Val  Ser  Gly  Phe  Ser  Leu
          35                       40                  45
Thr  Asn  Tyr  Ala  Ile  Asn  Trp  Val  Arg  Gln  Pro  Pro  Gly  Lys  Gly  Leu
     50                       55                  60
Glu  Trp  Leu  Gly  Ile  Ile  Trp  Thr  Gly  Gly  Gly  Thr  Ser  Tyr  Asn  Ser
 65                      70                  75                            80
Ala  Leu  Lys  Ser  Arg  Leu  Thr  Ile  Ser  Lys  Asp  Thr  Ser  Lys  Asn  Gln
                    85                  90                       95
Val  Ser  Leu  Lys  Leu  Ser  Ser  Val  Thr  Ala  Ala  Asp  Thr  Ala  Val  Tyr
               100                      105                      110
Tyr  Cys  Ala  Arg  Thr  Gly  Thr  Arg  Gly  Tyr  Phe  Phe  Asp  Tyr  Trp  Gly
```

|  | 115 |  |  |  | 120 |  |  |  | 125 |  |  |
|---|---|---|---|---|---|---|---|---|---|---|---|

Gln Gly Thr Leu Val Thr Val Ser Ser
       130                  135

(2) INFORMATION FOR SEQ ID NO:9:

(i) SEQUENCE CHARACTERISTICS:
        (A) LENGTH: 393 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..393

(ix) FEATURE:
        (A) NAME/KEY: mat_peptide
        (B) LOCATION: 61..393

(ix) FEATURE:
        (A) NAME/KEY: misc_feature
        (B) LOCATION: group(130..174, 220..240, 337..360)
        (D) OTHER INFORMATION: /note= "Complementarity Determining
            Regions(CDR-1, CDR-2 and CDR-3)"

(xi) SEQUENCE DESCRIPTION: SEQ ID NO:9:

```
ATG GAG ACA GAA ACA CTC CTG CTA TGG GTG CTG CTG CTC TGG GTT CCA      48
GGT TCC ACA GGT GAC ATT GTG CTG ACC CAA TCT CCA CCT TCT TTG GCT      96
GTG TCT CTA GGG CAG AGG GCC ACC ATA TCC TGC AGA GCC AGT GAA AGT     144
GTT GAT AGT TAT GGC AAT AGT TTT ATG CAC TGG TAC CAG CAG AAA CCA     192
GGA CAG CCA CCC AAA CTC CTC ATC TAT CGT GCA TCC AAC CTA GAA TCT     240
GGG ATC CCT GCC AGG TTC AGT GGC GGT GGG TCT AGG ACA GAC TTC ACC     288
CTC ACC ATT AAT CCT GTG GAG GCT GAT GAT GTT GCA ACC TAT TAC TGT     336
CAA CAA AGT AAT GAG GAT CCT CCG ACG TTC GGT GGA GGC ACC AAG CTG     384
GAA ATC AAA                                                          393
```

(2) INFORMATION FOR SEQ ID NO:10:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:10:

```
Met Glu Thr Glu Thr Leu Leu Leu Trp Val Leu Leu Leu Trp Val Pro
 1               5                  10                  15
Gly Ser Thr Gly Asp Ile Val Leu Thr Gln Ser Pro Pro Ser Leu Ala
            20                  25                  30
Val Ser Leu Gly Gln Arg Ala Thr Ile Ser Cys Arg Ala Ser Glu Ser
        35                  40                  45
Val Asp Ser Tyr Gly Asn Ser Phe Met His Trp Tyr Gln Gln Lys Pro
    50                  55                  60
Gly Gln Pro Pro Lys Leu Leu Ile Tyr Arg Ala Ser Asn Leu Glu Ser
65                  70                  75                  80
Gly Ile Pro Ala Arg Phe Ser Gly Gly Gly Ser Arg Thr Asp Phe Thr
                85                  90                  95
Leu Thr Ile Asn Pro Val Glu Ala Asp Asp Val Ala Thr Tyr Tyr Cys
                100                 105                 110
```

Gln Gln Ser Asn Glu Asp Pro Pro Thr Phe Gly Gly Gly Thr Lys Leu
115                     120                     125

Glu Ile Lys
    130

( 2 ) INFORMATION FOR SEQ ID NO:11:

( i ) SEQUENCE CHARACTERISTICS:
        ( A ) LENGTH: 405 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..405

( i x ) FEATURE:
        ( A ) NAME/KEY: mat_peptide
        ( B ) LOCATION: 58..405

( i x ) FEATURE:
        ( A ) NAME/KEY: misc_feature
        ( B ) LOCATION: group(147..162, 205..255, 352..381)
        ( D ) OTHER INFORMATION: /note= "Complementarity Determining
            Regions(CDR- 1, CDR-2 and CDR-3)"

( x i ) SEQUENCE DESCRIPTION: SEQ ID NO:11:

ATG GAA AGG CAC TGG ATC TTT CTC TTC CTG TTT TCA GTA ACT GCA GGT    48

GTC CAC TCC CAG GTC CAG CTT CAG CAG TCT GGG GCT GAA GTG GCA AAA    96

CCT GGG GCC TCA GTG AAG ATG TCC TGC AAG GCT TCT GGC TAC ACC TTT   144

ACT AAC TGC TGG ATG CAC TGG GTA AAA CAG AGG CCT GGA CAG GGT CTG   192

GAA TGG ATT GGA TAC ATT AAT CCT ACC ACT GGT TAT TCT GAG TAC AAT   240

CAG AAC TTC AAG GAC AAG GCC ACA TTG ACT GCA GAC AAA TCC TCC AAC   288

ACA GCC TAC ATT CAA CTG AGT AGC CTG ACA TCT GAG GAC TCT GCA GTC   336

TAT TAC TGT ACA AGC AAC TAT GGT CAC TAC GAC TGG TTT GCT AAC TGG   384

GGC CAA GGG ACT CTG GTC ACT                                       405

( 2 ) INFORMATION FOR SEQ ID NO:12:

( i ) SEQUENCE CHARACTERISTICS:
        ( A ) LENGTH: 135 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

Met Glu Arg His Trp Ile Phe Leu Phe Leu Phe Ser Val Thr Ala Gly
1               5                   10                  15

Val His Ser Gln Val Gln Leu Gln Gln Ser Gly Ala Glu Val Ala Lys
            20                  25                  30

Pro Gly Ala Ser Val Lys Met Ser Cys Lys Ala Ser Gly Tyr Thr Phe
        35                  40                  45

Thr Asn Cys Trp Met His Trp Val Lys Gln Arg Pro Gly Gln Gly Leu
    50                  55                  60

Glu Trp Ile Gly Tyr Ile Asn Pro Thr Thr Gly Tyr Ser Glu Tyr Asn
65                  70                  75                  80

Gln Asn Phe Lys Asp Lys Ala Thr Leu Thr Ala Asp Lys Ser Ser Asn
                85                  90                  95

```
Thr  Ala  Tyr  Ile  Gln  Leu  Ser  Ser  Leu  Thr  Ser  Glu  Asp  Ser  Ala  Val
               100                      105                     110

Tyr  Tyr  Cys  Thr  Ser  Asn  Tyr  Gly  His  Tyr  Asp  Trp  Phe  Ala  Asn  Trp
               115                      120                     125

Gly  Gln  Gly  Thr  Leu  Val  Thr
          130                      135
```

(2) INFORMATION FOR SEQ ID NO:13:

(i) SEQUENCE CHARACTERISTICS:
        (A) LENGTH: 393 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..393

(ix) FEATURE:
        (A) NAME/KEY: mat_peptide
        (B) LOCATION: 61..393

(ix) FEATURE:
        (A) NAME/KEY: misc_feature
        (B) LOCATION: group(130..174, 220..240, 337..360)
        (D) OTHER INFORMATION: /note= "Complementarity Determining
            Regions(CDR-1, CDR-2 and CDR-3)"

(xi) SEQUENCE DESCRIPTION: SEQ ID NO:13:

```
ATG  GAG  ACC  GAT  ACC  CTC  CTG  CTA  TGG  GTC  CTC  CTG  CTA  TGG  GTC  CCA        48

GGA  TCA  ACC  GGA  GAC  ATC  CAG  ATG  ACC  CAG  TCT  CCA  TCC  TCC  CTG  TCT        96

GCT  AGC  GTA  GGA  GAC  AGG  GTC  ACC  ATC  ACT  TGC  AGA  GCC  AGT  GAA  AGT       144

GTT  GAT  AGT  TAT  GGC  AAT  AGT  TTT  ATG  CAC  TGG  TAC  CAG  CAG  AAA  CCA       192

GGG  AAA  GCT  CCT  AAG  CTC  CTG  ATC  TAT  CGT  GCA  TCC  AAC  CTA  GAA  TCT       240

GGA  ATC  CCA  TCT  CGG  TTC  AGT  GGC  AGT  GGA  TCT  AGG  ACA  GAT  TTC  ACT       288

CTC  ACC  ATC  AGC  AGC  CTG  CAG  CCT  GAA  GAT  GTT  GCA  ACT  TAT  TAC  TGT       336

CAA  CAA  AGT  AAT  GAG  GAC  CCT  CCG  ACG  TTC  GGT  CAA  GGG  ACC  AAG  GTG       384

GAA  ATC  AAA                                                                         393
```

(2) INFORMATION FOR SEQ ID NO:14:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:14:

```
Met  Glu  Thr  Asp  Thr  Leu  Leu  Leu  Trp  Val  Leu  Leu  Leu  Trp  Val  Pro
 1                   5                        10                       15

Gly  Ser  Thr  Gly  Asp  Ile  Gln  Met  Thr  Gln  Ser  Pro  Ser  Ser  Leu  Ser
               20                      25                      30

Ala  Ser  Val  Gly  Asp  Arg  Val  Thr  Ile  Thr  Cys  Arg  Ala  Ser  Glu  Ser
               35                      40                      45

Val  Asp  Ser  Tyr  Gly  Asn  Ser  Phe  Met  His  Trp  Tyr  Gln  Gln  Lys  Pro
          50                       55                      60

Gly  Lys  Ala  Pro  Lys  Leu  Leu  Ile  Tyr  Arg  Ala  Ser  Asn  Leu  Glu  Ser
 65                      70                      75                        80

Gly  Ile  Pro  Ser  Arg  Phe  Ser  Gly  Ser  Gly  Ser  Arg  Thr  Asp  Phe  Thr
```

|  |  |  |  | 85 |  |  |  |  | 90 |  |  |  |  | 95 |  |
|---|---|---|---|---|---|---|---|---|---|---|---|---|---|---|---|
| Leu | Thr | Ile | Ser | Ser | Leu | Gln | Pro | Glu | Asp | Val | Ala | Thr | Tyr | Tyr | Cys |
|  |  |  | 100 |  |  |  |  | 105 |  |  |  |  | 110 |  |  |
| Gln | Gln | Ser | Asn | Glu | Asp | Pro | Pro | Thr | Phe | Gly | Gln | Gly | Thr | Lys | Val |
|  |  |  | 115 |  |  |  |  | 120 |  |  |  |  | 125 |  |  |
| Glu | Ile | Lys |  |  |  |  |  |  |  |  |  |  |  |  |  |
|  |  | 130 |  |  |  |  |  |  |  |  |  |  |  |  |  |

( 2 ) INFORMATION FOR SEQ ID NO:15:

( i ) SEQUENCE CHARACTERISTICS:
        ( A ) LENGTH: 405 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..405

( i x ) FEATURE:
        ( A ) NAME/KEY: mat_peptide
        ( B ) LOCATION: 58..405

( i x ) FEATURE:
        ( A ) NAME/KEY: misc_feature
        ( B ) LOCATION: group(147..162, 206..255, 352..381)
        ( D ) OTHER INFORMATION: /note= "Complementarity Determing
                Regions(CDR- 1, CDR-2 and CDR-3)"

( x i ) SEQUENCE DESCRIPTION: SEQ ID NO:15:

| ATG | GGA | TGG | AGC | TGG | ATC | TTT | CTC | TTC | CTC | CTG | TCA | GGT | ACC | GCG | GGC | 48 |
| GTG | CAC | TCT | CAG | GTG | CAG | CTG | GTG | CAG | TCT | GGG | GCT | GAG | GTG | AAG | AAG | 96 |
| CCT | GGC | GCC | TCG | GTA | AAG | GTC | TCC | TGC | AAG | GCT | TCT | GGA | TAC | ACC | TTC | 144 |
| ACT | AAC | TGC | TGG | ATG | CAT | TGG | GTG | CGA | CAG | GCC | CCT | GGA | CAA | GGG | CTT | 192 |
| GAG | TGG | ATT | GGA | TAC | ATT | AAT | CCT | ACC | ACT | GGT | TAT | TCT | GAG | TAC | AAT | 240 |
| CAG | AAC | TTC | AAG | GAC | AAG | GCC | ACG | ATT | ACC | GCG | GAC | AAA | TCC | ACG | AGC | 288 |
| ACA | GCC | TAC | ATG | GAG | CTG | AGC | AGC | CTG | AGA | TCT | GAG | GAC | ACG | GCC | GTG | 336 |
| TAT | TAC | TGT | ACA | AGC | AAC | TAT | GGT | CAC | TAC | GAC | TGG | TTT | GGT | AAC | TGG | 384 |
| GGC | CAG | GGA | ACC | CTG | GTC | ACA |  |  |  |  |  |  |  |  |  | 405 |

( 2 ) INFORMATION FOR SEQ ID NO:16:

( i ) SEQUENCE CHARACTERISTICS:
        ( A ) LENGTH: 135 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Met | Gly | Trp | Ser | Trp | Ile | Phe | Leu | Phe | Leu | Leu | Ser | Gly | Thr | Ala | Gly |
|---|---|---|---|---|---|---|---|---|---|---|---|---|---|---|---|
| 1 |  |  |  | 5 |  |  |  |  | 10 |  |  |  |  | 15 |  |
| Val | His | Ser | Gln | Val | Gln | Leu | Val | Gln | Ser | Gly | Ala | Glu | Val | Lys | Lys |
|  |  |  | 20 |  |  |  |  | 25 |  |  |  |  | 30 |  |  |
| Pro | Gly | Ala | Ser | Val | Lys | Val | Ser | Cys | Lys | Ala | Ser | Gly | Tyr | Thr | Phe |
|  |  |  | 35 |  |  |  |  | 40 |  |  |  |  | 45 |  |  |
| Thr | Asn | Cys | Trp | Met | His | Trp | Val | Arg | Gln | Ala | Pro | Gly | Gln | Gly | Leu |
|  |  |  | 50 |  |  |  |  | 55 |  |  |  |  | 60 |  |  |
| Glu | Trp | Ile | Gly | Tyr | Ile | Asn | Pro | Thr | Thr | Gly | Tyr | Ser | Glu | Tyr | Asn |
| 65 |  |  |  |  | 70 |  |  |  |  | 75 |  |  |  |  | 80 |

-continued

```
Gln  Asn  Phe  Lys  Asp  Lys  Ala  Thr  Ile  Thr  Ala  Asp  Lys  Ser  Thr  Ser
                    85                      90                      95

Thr  Ala  Tyr  Met  Glu  Leu  Ser  Ser  Leu  Arg  Ser  Glu  Asp  Thr  Ala  Val
                   100                     105                     110

Tyr  Tyr  Cys  Thr  Ser  Asn  Tyr  Gly  His  Tyr  Asp  Trp  Phe  Gly  Asn  Trp
              115                     120                     125

Gly  Gln  Gly  Thr  Leu  Val  Thr
         130                     135
```

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Gly  Gly  Gly  Gly  Ser  Gly  Gly  Gly  Gly  Ser  Gly  Gly  Gly  Gly  Ser
 1                     5                    10                     15
```

MONOCLONAL ANTIBODIES SPECIFIC FOR THE PLATELET DERIVED GROWTH FACTOR β RECEPTOR AND METHODS OF USE THEREOF

FIELD OF THE INVENTION

The invention relates to antibodies specific for the platelet derived growth factor (PDGF) β receptor (PDGF-R β) binding not within the fifth extracellular Ig-like domain. The antibodies inhibit proliferation induced by PDGF BB and are suitable for use in various medical applications, particularly in ameliorating restenosis.

BACKGROUND

Platelet derived growth factor (PDGF) is a mitogen and chemoattractant for cells of mesenchymal origin, such as fibroblasts, smooth muscle cells, and glial cells. This cytokine was first described as a platelet-derived mitogenic activity in serum, although subsequent studies have revealed that a variety of cells, including macrophages, endothelial cells and several tumor cell types also secrete the cytokine. PDGF is encoded by two genes, the products of which are designated A and B. The active PDGF molecule is a disulfide-linked dimer of these polypeptides, and thus can exist in three forms: the homodimers AA or BB, or the heterodimer AB. Platelets synthesize 70% AB, 20% BB and 10% AA. The A and B polypeptides exhibit a 60% homology at the amino acid sequence level, with complete conservation of eight cysteine residues.

Studies examining the interaction of PDGF with responsive cells have revealed the existence of two specific receptors, designated α and β. Each receptor type is composed of five extracellular antibody-like domains attached to an intracellular tyrosine kinase domain via a transmembrane segment. The molecular weights of the mature forms of the PDGF receptors are 170,000 and 180,000 Daltons for the α and β forms, respectively. The receptors are heavily glycosylated; carbohydrates on the extracellular portion of the receptors account for approximately 30% of the total molecular mass.

The active form of the PDGF receptor (PDGF-R) is a dimer, with two receptor molecules being bridged by a single PDGF dimer. The different forms of PDGF exhibit different affinities for the two forms of the PDGF receptor. PDGF-R α can interact with all three forms of PDGF; PDGF-R β can only interact with PDGF BB and AB. This pattern of reactivity dictates that PDGF AA can signal the cell only through homodimers of PDGF-R α; PDGF BB can signal the cell through homodimers of PDGF-R α or PDGF-R β, or the heterodimer of PDGF-R α and PDGF-R β; and PDGF AB can stimulate cells through either homodimers of PDGF-R α, or the heterodimers. Claesson-Welsh, J. Biol. Chem. 269:32023 (1994).

Antibodies specific for PDGF-R have been isolated. Early antibodies had little utility. Kawahara et al. (1987) Biochim. Biophys. Res. Commun. 147:839–845. Additional monoclonal antibodies have been raised against the extracellular PDGF-binding domain of PDGF-R from porcine uterus but these antibodies did not inhibit binding of $^{125}$I-labeled PDGF to human fibroblasts. Rönnstrand and Terracio (1988) J. Biol. Chem. 263:10429–10435. Numerous antibodies specific for a PDGF-R have been isolated but did not inhibit PDGF activity. Kanakaraj et al. (1991) Biochem. 30:1761–1767; Claesson-Welsh et al. (1989) J. Biol. Chem. 264:1742–1747; Seifert et al. (1989) J. Biol. Chem. 264:8771–8778; Kumjian et al. (1989) Proc. Natl. Acad. Sci. USA 86:8232–8236; Bishayee et al. (1988) Mol. Cell Biol. 8:3696–3702; Hart et al. (1987) J. Biol. Chem. 262:10780–10785; Escobedo et al. (1988) J. Biol. Chem. 263:1482–1487; Daniel et al. (1987) J. Biol. Chem. 262:9778–9784; Keating and Williams (1987) J. Biol. Chem. 262:7932–7937; and Kazlauskas and Copper (1990) EMBO J. 9:3279–3286. More recently, antibodies that inhibit the effects of PDGF have been described. WO 93/10805; and WO 94/19016. The antibodies described in WO 93/10805 bind to the fifth Ig-like domain of PDGF-R β. WO 94/19016 describes the use of antibodies specific for PDGF-R α and β to reduce intimal hyperplasia.

As a potent mitogenic and chemotactic agent, PDGF has been implicated as a contributing factor in a number of pathologic conditions that involve the migration and proliferation of PDGF responsive cells. Such conditions include arteriosclerosis, restenosis following coronary bypass surgery or balloon angioplasty, nephritis, scleroderma, and some types of cancer including lung cancer and Kaposi's sarcoma.

Restenosis is a common complication of balloon angioplasty or coronary bypass surgery, occurring after up to 40% of such procedures. Holmes et al. (1988) J. Amer. Coll. Cardiol. 12:1149. Histologically, the restenosis is due almost entirely to the accumulation and proliferation of neointimal smooth muscle cells, i.e., to intimal hyperplasia. PDGF is both chemotactic and mitogenic for smooth muscle cells, suggesting that this cytokine is involved in causing restenosis. Experimental support for a connection of PDGF to restenosis exists. Treatment of rats with a goat polyclonal antiserum raised against human PDGF (all isoforms) resulted in a 40% decrease in subsequent neointima formation following vascular de-endothelialization via a balloon catheter. Ferns et al. (1991). Thus, neutralizing the PDGF-mediated mitogenesis of smooth muscle cells appears to be a viable therapeutic tactic for this complication.

All references cited herein, both supra and infra, are hereby incorporated herein by reference.

SUMMARY OF THE INVENTION

The invention encompasses monoclonal antibodies ("MAb") including specific binding fragments thereof that specifically bind to the PDGF-R β but do not bind to the fifth extracellular domain of PDGF-R β (i.e., "not within" this region). These antibodies are hereafter designated "Δ5." In one embodiment, specific binding of Δ5 antibodies to the PDGF-R β inhibits binding of PDGF to PDGF-R β, and inhibits stimulation of proliferation of cells expressing PDGF-R β by PDGF BB. In another embodiment, specific binding of Δ5 antibodies to the PDGF-R β inhibits such stimulation of proliferation but does not inhibit binding of PDGF to PDGF-R β. Thus, as described in more detail below, the invention further encompasses methods of inhibiting PDGF BB stimulation of proliferation of cells expressing PDGF-R β.

The invention further encompasses the exemplary Δ5 murine monoclonal antibodies (muAb) designated muM4TS.11 and muM4TS.22. Many of the Δ5 antibodies compete with these antibodies for specific binding to PDGF-R β.

In one embodiment, the Δ5 antibodies specifically recognize an epitope in the third or fourth extracellular domain of PDGF-R β. In another embodiment, the Δ5 antibodies bind to the same epitope of PDGF-R β as antibody muM4TS.11 or muM4TS.22.

In addition to intact antibodies, the invention also provides specific binding fragments of Δ5 antibodies including, but not limited to, Fab, Fab', F(ab')$_2$, Fv or single-chain antibodies.

The invention encompasses Δ5 antibodies that are non-human, e.g., muab, humanized antibodies ("HuAb") or human antibodies. As used herein, the term Δ5 antibody encompasses all variants of the antibodies and specific binding fragments thereof.

A HuAb comprises a humanized heavy chain variable region and a humanized light chain variable region. The humanized light chain variable region comprises complementarity determining regions (e.g., CDR1, CDR2, CDR3) having amino acid sequences from the light chain of a muAb selected from the group consisting of muM4TS.11 and muM4TS.22, and having a variable region framework sequence substantially identical to a human light chain variable region framework sequence. The humanized heavy chain variable region comprises complementarity determining regions (e.g., CDR1, CDR2 and CDR3) having amino acid sequences from the corresponding muAb heavy chain, and having a variable region framework sequence substantially identical to a human heavy chain variable region framework sequence. The antibodies optionally contain constant regions substantially identical to human constant regions. Exemplary Δ5 antibodies are HuM4TS.11 and HuM4TS.22, the construction, expression and activity of which are as described in detail herein.

In particular embodiments of the Δ5 HuAbs of this invention, the humanized light chain variable region has a sequence substantially identical to the mature sequence depicted in FIG. 2B (SEQ ID NO:6) or FIG. 8B (SEQ ID NO:14) and the humanized heavy chain variable region has a sequence substantially identical to the mature sequence depicted in FIG. 2D (SEQ ID NO:8) or FIG. 8D (SEQ ID NO:16).

In another aspect, the invention provides purified nucleic acid segments encoding a light or heavy chain variable region of one of the MAbs discussed above.

The invention further encompasses pharmaceutical compositions comprising the Δ5 antibodies and pharmaceutically acceptable excipients.

The invention further encompasses methods of treatment using the Δ5 antibody pharmaceutical compositions. The methods of treatment are particularly effective for inhibiting intimal hyperplasia in the vasculature of a patient, e.g., by balloon dilatation.

BRIEF DESCRIPTION OF THE DRAWINGS

FIG. 1 depicts the sequences of the cDNA and translated amino acid sequences of the light and heavy chains of the variable regions of muM4TS.22. FIG. 1A depicts the cDNA sequence of the light chain (SEQ ID NO:1). FIG. 1B depicts the amino acid sequence of the light chain (SEQ ID NO:2). FIG. 1C depicts the cDNA sequence of the heavy chain (SEQ ID NO:3). FIG. 1D depicts the amino acid sequence of the heavy chain (SEQ ID NO:4). The first amino acid of each mature chain is indicated by a double underline. The three CDRs in each chain are underlined.

FIG. 2 depicts the sequences of the synthetic DNA and translated amino acid sequences of the light and heavy chains of the variable regions of HuM4TS.22. FIG. 2A depicts the DNA sequence of the light chain (SEQ ID NO:5). FIG. 2B depicts the amino acid sequence of the light chain (SEQ ID NO:6). FIG. 2C depicts the DNA sequence of the heavy chain (SEQ ID NO:7). FIG. 2D depicts the amino acid sequence of the heavy chain (SEQ ID NO:8). The first amino acid of each mature chain is indicated by a double underline. The three CDRs in each chain are underlined.

FIG. 7 depicts the sequences of the cDNA and translated amino acid sequences of the light and heavy chains of the variable regions of muM4TS.11. FIG. 7A depicts the cDNA sequence of the light chain (SEQ ID NO:9). FIG. 7B depicts the amino acid sequence of the light chain (SEQ ID NO:10). FIG. 7C depicts the cDNA sequence of the heavy chain (SEQ ID NO:11). FIG. 7D depicts the amino acid sequence of the heavy chain (SEQ ID NO:12). The first amino acid of each mature chain is indicated by a double underline. The three CDRs in each chain are underlined.

FIG. 8 depicts sequences of the synthetic DNA and translated amino acid sequences of the light and heavy chains of the variable regions of HuM4TS.11. FIG. 8A depicts the DNA sequence of the light chain (SEQ ID NO:13). FIG. 8B depicts the amino acid sequence of the light chain (SEQ ID NO:14). FIG. 8C depicts the DNA sequence of the heavy chain (SEQ ID NO:15). FIG. 8D depicts the amino acid sequence of the heavy chain (SEQ ID NO:16). The first amino acid of each mature chain is indicated by a double underline. The three CDRs in each chain are underlined.

FIG. 14 is a series of bar graphs depicting the results of ELISA to measure binding of the indicated antibodies to the indicated PDGF-R β deletion proteins, performed as described in the text (D1–5=purified soluble PDGF-R β).

DESCRIPTION OF THE PREFERRED EMBODIMENTS

Figure 3:
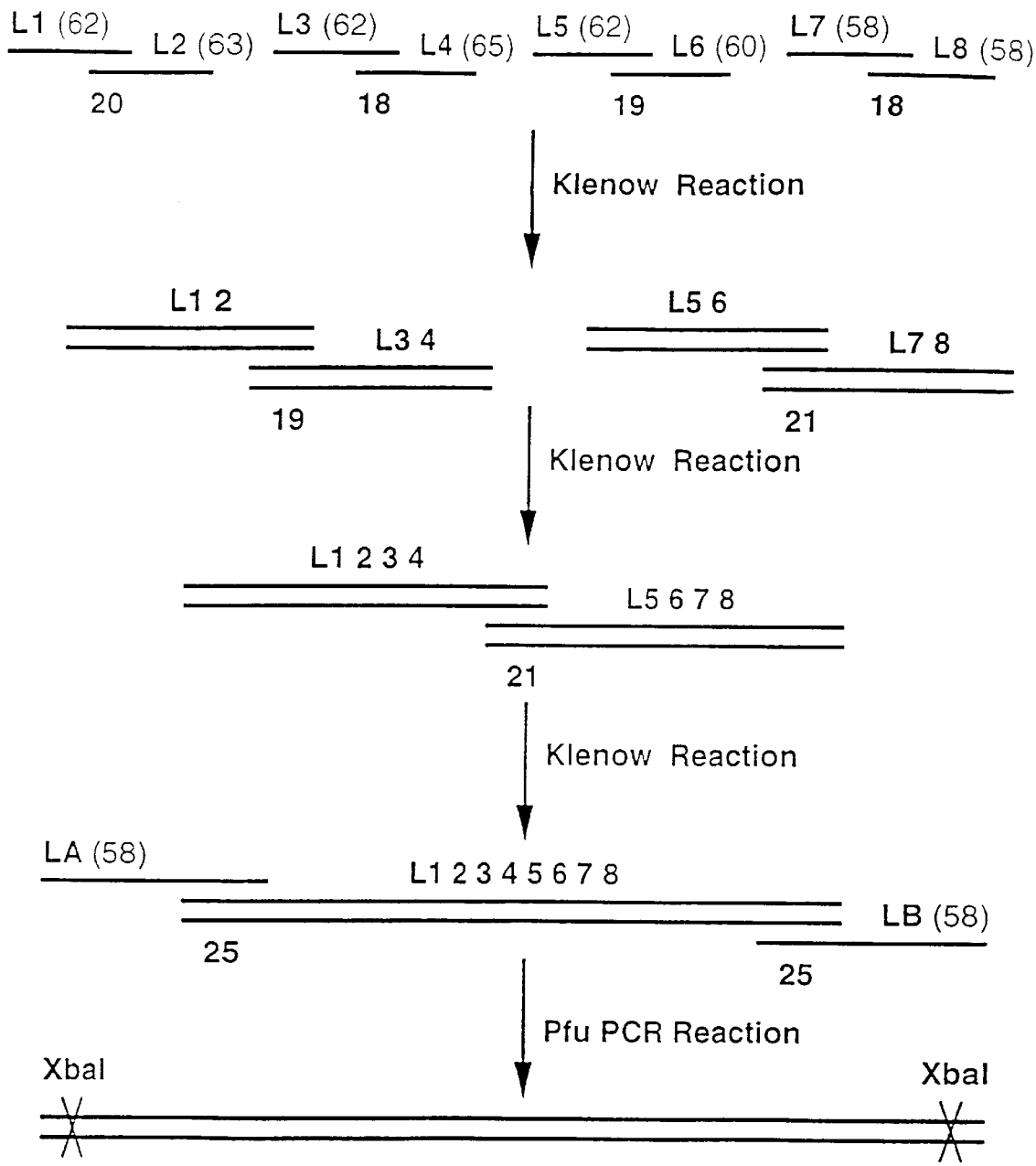
FIG. 3 is a schematic diagram of the construction of the HuM4TS.22 light chain variable region gene. The numbers in parentheses indicate the length of each oligonucleotide, and the numbers underneath the lines indicate the length of the overlapping region of each pair of oligonucleotides.

The present invention provides antibodies, and specific binding fragments thereof, specific for PDGF-R β extracellular domains 1–4. In one embodiment, the antibodies block binding of PDGF BB to PDGF-R β. In all embodiments, the antibodies inhibit PDGF BB induced proliferation. The invention further encompasses exemplary muAbs, their humanized forms and the nucleotides encoding these antibodies. The antibodies can be formulated with pharmaceutical excipients to provide pharmaceutical compositions. Methods of use of the pharmaceutical compositions are provided which prevent PDGF BB-induced cellular proliferation, particularly during restenosis.

The definitions provided below are for the purpose of clarifying the terms used herein. The definitions are not meant to be limiting, and more detailed explanations and examples are provided throughout the specification.

As used herein, "antibody" or "immunoglobulin" refers to proteins which have specific immunoreactivity and consist of one or more polypeptide chains substantially encoded by immunoglobulin genes. Immunoglobulin genes include those coding for the light chains, which may be of the kappa or lambda types, and those coding for the heavy chains. Heavy chain types are alpha, gamma, delta, epsilon and mu. The carboxy terminal portions of immunoglobulin heavy and light chains are constant regions, while the amino terminal portions are encoded by the myriad immunoglobulin variable region genes. The variable regions of an immunoglobulin are the portions that provide antigen recognition specificity. In particular, the specificity primarily resides in the complementarity determining regions (CDRs), also known as hypervariable regions, of the immunoglobulins. Antibodies are typically tetramers of immunoglobulin polypeptide chains, but may exist in a variety of other forms including, but not limited to, Fv, Fab, and F(ab')$_2$, as well as in single chains. See, generally, Hood, et al. "Immunology", Benjamin, N.Y., 2nd ed. (1984).

MAbs may be obtained by various techniques familiar to those skilled in the art. Briefly, spleen cells from an animal immunized with a desired antigen are immortalized, commonly by fusion with a myeloma cell. See Kohler and Milstein, Eur. J. Inuunol. 6:511–519 (1976). Alternative methods of immortalization include transformation with Epstein Barr Virus (EBV), oncogenes, or retroviruses, or other methods well known in the art. Colonies arising from single immortalized cells are screened for production of antibodies of the desired specificity and affinity for the antigen. Yield of the MAbs produced by such cells may be enhanced by various techniques, including injection into the peritoneal cavity of a vertebrate host.

Monospecific antibodies may also be produced by recombinant techniques in prokaryotic or eukaryotic host cells.

"Chimeric" antibodies are encoded by immunoglobulin genes that have been genetically engineered so that the light and heavy chain genes are composed of immunoglobulin gene segments belonging to different species. For example, the variable (V) segments of the genes from a muMAb may be joined to human constant (C) segments. Such a chimeric antibody is likely to be less antigenic to a human than antibodies with murine constant regions as well as murine variable regions.

As used herein, the term humanized antibody (HuAb) refers to an antibody with a framework substantially identical (i.e., at least 85%) to a human framework, having CDRs from a non-human antibody, and in which any constant region present has at least about 85–90%, and preferably about 95% polypeptide sequence identity to a human immunoglobulin constant region. See, for example, PCT Publication WO 90/07861 and European Patent No. 0451216. Hence, all parts of such a HuAb, except possibly the CDR's, are substantially identical to corresponding parts of one or more native human immunoglobulin sequences. The term "framework region", as used herein, refers to those portions of immunoglobulin light and heavy chain variable regions that are relatively conserved (ie., other than the CDR's) among different immunoglobulins in a single species, as defined by Kabat, et al. (1987) *Sequences of Proteins of Immunologic Interest*, 4th Ed., US Dept. Health and Human Services.

Human constant region DNA sequences can be isolated in accordance with well known procedures from a variety of human cells, but preferably from immortalized B cells. The variable regions or CDRs for producing the humanized antibodies of the present invention will be similarly derived from MAbs capable of binding to the human type beta PDGF receptor, and will be produced in any convenient mammalian source, including, mice, rats, rabbits, or other vertebrates capable of producing antibodies, by well known methods.

Suitable source cells for the DNA sequences and host cells for antibody expression and secretion can be obtained from a number of sources, such as the American Type Culture Collection ("Catalogue of Cell Lines and Hybridomas," Fifth edition (1985) Rockville, Md., U.S.A.).

In addition to the chimeric and HuAbs specifically described herein, other substantially identical modified antibodies can be readily designed and manufactured utilizing various recombinant DNA techniques well known to those skilled in the art. In general, modifications of the genes may be readily accomplished by a variety of well-known techniques, such as site-directed mutagenesis. See, Gillman and Smith (1979) Gene 8:81–97; and Roberts et al. (1987) Nature 328:731–734.

Alternatively, polypeptide fragments comprising only a portion of the primary immunoglobulin structure may be produced. For example, it may be desirable to produce antibody polypeptide fragments that possess one or more antibody activities in addition to, or other than, antigen recognition (e.g., complement fixation).

The invention also encompasses Δ5 antibodies conjugated to a label capable of producing a detectable signal or to other functional moieties, such as toxins. Immunoglobulin genes, in whole or in part, may also be combined with functional regions from other genes (e.g., enzymes), or with other molecules such as toxins or labels to produce fusion proteins (e.g., "immunotoxins") having novel properties. In these cases of gene fusion, the two components are present within the same polypeptide chain. Alternatively, Δ5 antibodies may be chemically bonded to the toxin or label by any of a variety of well-known chemical procedures. For example, when the label or cytotoxic agent is a protein and the second component is an intact antibody, the linkage may be by way of heterobifunctional cross-linkers, e.g., SPDP, carbodiimide glutaraldehyde, or the like or by recombinant methods. The labels may be covalently linked to Δ5 antibodies, or conjugated through a secondary reagent, such as a second antibody, protein A, or a biotin-avidin complex.

Suitable labels include, but are not limited to, radionuclides, enzymes, substrates, cofactors, inhibitors, fluorescent dyes, chemiluminescent dyes, bioluminescent compounds and magnetic particles. See, for examples of patents teaching the use of such labels, U.S. Pat. Nos. 3,817,837; 3,850,752; 3,939,350; 3,996,345; 4,277,437; 4,275,149; and 4,366,241.

Immunotoxins, including single chain molecules, may also be produced by recombinant means. Production of various immunotoxins is well-known in the art, and methods can be found, for example in "Monoclonal Antibody-Toxin Conjugates: Aiming the Magic Bullet," Thorpe et al. (1982) *Monoclonal Antibodies in Clinical Medicine*, Academic Press, pp. 168–190; Vitatta, Science (1987) 238:1098–1104; and Winter and Milstein (1991), Nature 349:293–299.

A variety of cytotoxic agents are suitable for use in immunotoxins. Cytotoxic agents include, but are not limited to, radionuclides, such as Iodine-131, Yttrium-90, Rhenium-188, and Bismuth-212; a number of chemotherapeutic drugs, such as vindesine, methotrexate, adriamycin, and cisplatinum; and cytotoxic proteins such as ribosomal inhibiting proteins like pokeweed antiviral protein, Pseudomonas exotoxin A, ricin, diphtheria toxin, ricin A chain, etc., or an agent active at the cell surface, such as the phospholipase enzymes (e.g., phospholipase C). See, generally, "Chimeric Toxins," Olsnes and Pihl, Pharmac. Ther., 15:355–381 (1981); and "Monoclonal Antibodies for Cancer Detection and Therapy," eds. Baldwin and Byers, pp. 159–179, 224–266, Academic Press (1985).

The invention also encompasses HuAbs. The choice of framework residues can be critical in retaining high binding affinity. In principle, a framework sequence from any HuAb can serve as the template for CDR grafting; however, it has been demonstrated that straight CDR replacement into such a framework can lead to significant loss of binding affinity to the antigen. Glaser et al. (1992) J. Immunol. 149:2606; Tempest et al. (1992) Biotechnology 9:266; and Shalaby et al. (1992) J. Exp. Med. 17:217. The more homologous a HuAb is to the original muAb, the less likely that the human framework will introduce distortions into the murine CDRs that could reduce affinity. Based on a sequence homology search against an antibody sequence database, the HuAb IC4 provides good framework homology to muM4TS.22, although other highly homologous HuAbs would be suitable as well, especially kappa light chains from human subgroup I or heavy chains from human subgroup III. Kabat et al. (1987). Various computer programs such as ENCAD (Levitt et al. (1983) J. Mol. Biol. 168:595) are available to predict the ideal sequence for the variable region. The invention thus encompasses HuAbs with different variable regions. It is within the skill of one in the art to determine suitable variable region sequences and to optimize these sequences. For exemplification, see Examples 5 and 9 and the tables therein.

The invention further encompasses fusion proteins comprising one or more Δ5 polypeptide. A Δ5 fusion polypeptide can be prepared, for example, by chemical synthesis, or by creating and translating a polynucleotide in which the peptide regions are encoded in the desired relationship. Alternatively, fusion proteins may be made in expression systems of co-transfected plasmids comprising encoding regions for different functional regions of the protein.

Useful heterologous sequences for inclusion in a fusion polypeptide include sequences that provide for secretion from a host cell, enhance immunological reactivity, or facilitate the coupling of the polypeptide to an immunoassay support or a vaccine carrier. One example is a bacterial "super antigen", such as staphylococcal enterotoxin A (SEA). Dohlsten et al. (1994) Proc. Natl. Acad. Sci. USA 91:8945–8949. In a preferred example, a Δ5 polypeptide is fused with a bioresponse modifier, particularly a cytokine. Examples of bioresponse modifiers include, but are not limited to, cytokines and lymphokines such as GM-CSF, interleukin-2 (IL-2), interleukin 4 (IL-4), and γ-interferon. GM-CSF and IL-2 are especially preferred. The preferred arrangement is for the cytokine effector unit to be fused to the C-terminal of the immunoglobulin heavy chain.

Δ5 polypeptide derivatives comprising both a Δ5 light chain and a Δ5 heavy chain may be formed as separate light and heavy chains and then assembled, or assembled in situ by an expression system for both chains. Such expression systems may be created by transfecting a host cell with a plasmid comprising separate transcribable regions for the light and heavy chain, or by co-transfecting the same cell with plasmids for each chain. In a third method, a suitable plasmid with a heavy chain encoding region is transfected into a heavy chain loss mutant.

The invention also encompasses a hybrid antibody, in which one pair of heavy and light chains is obtained from a first antibody, while the other pair of heavy and light chains is obtained from a different second antibody. For purposes of this invention, one pair of light and heavy chains is from Δ5. In one example, each light-heavy chain pair binds different epitopes of PDGF-R β. Such hybrids may also be formed using humanized heavy or light chains.

Another Δ5 derivative contemplated by this invention is an antibody in which the Δ5 heavy or light chain has been modified to provide additional properties. For instance, a change in amino acid sequence can result in reduced immunogenicity of the resultant Δ5 polypeptide. The changes range from changing of one or more amino acids to the complete redesign of a region such as a constant region domain. Typical changes include, but are not limited to, those related to complement fixation, interaction with membrane receptors, and other effector functions. A recombinant Δ5 antibody may also be designed to aid the specific delivery of a substance (such as a lymphokine) to an effector cell. Also contemplated are proteins in which various immunoglobulin domains have been placed in an order other than that which occurs in nature.

The invention also encompasses single chain variable region fragments ("scFv") of Δ5. Single chain variable region fragments are made by linking light and/or heavy chain variable regions by using a short linking peptide. Bird et al. (1988) Science 242:423–426. Any peptide having sufficient flexibility and length can be used as a linker in a scFv. Usually the linker is selected to have little to no immunogenicity. An example of a linking peptide is $(GGGGS)_3$ (SEQ ID NO:17), which bridges approximately 3.5 nm between the carboxy terminus of one variable region and the amino terminus of another variable region. Other linker sequences may also be used, and may provide additional functions, such as a means for attaching a drug or to a solid support.

All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or portion thereof. Also contemplated are scFvs in which the heavy chain variable region is from Δ5, and the light chain variable region is from another antibody. It is also possible to construct a biphasic, scFv in which one component is a Δ5 polypeptide and another component is a different polypeptide, such as a T cell epitope. The scFvs can be assembled in any order, for example, $V_H$—(linker)—$V_L$ or $V_L$—(linker)—$V_H$.

Single chain variable regions may be produced either recombinantly or synthetically. For synthetic production of scFv, an automated synthesizer can be used. For recombinant production of scFv, a suitable plasmid containing polynucleotide that encodes the scFv can be introduced into a suitable host cell.

The invention encompasses polypeptide and substantially identical polypeptide fragments of Δ5 antibodies. The invention encompasses polypeptide fragments of Δ5 antibodies containing at least a portion of a variable region of Δ5. Preferred fragments are those with immunological activity of Δ5.

Also preferred are fragments which comprise amino acid sequences substantially different from other antibodies, and fragments comprising a CDR. In one embodiment, the invention includes a polypeptide fragment of the Δ5 light chain variable region, comprising at least 25 consecutive amino acids, more preferably 30 consecutive amino acids of SEQ ID NOS:2, 6, 10 or 14; or 5 consecutive amino acids of the CDR1 thereof, or at least 7 consecutive amino acids, preferably at least 9 consecutive amino acids of the CDR2 or CDR3 thereof. The invention also includes a polypeptide fragment of the Δ5 heavy chain variable region, comprising at least 25 consecutive amino acids, more preferably 30 consecutive amino acids of SEQ ID NOS:4, 8, 12 or 16; or 7 consecutive amino acids of the CDR2 thereof, or at least 8 consecutive amino acids, preferably 10 consecutive amino acids of the CDR1 or CDR3 thereof.

The size of the Δ5 polypeptide fragments may be only the minimum size required to provide a desired function and specificity. It may optionally comprise additional amino acid sequence, either native to Δ5, or from a heterologous source, as desired. Δ5 fragments may contain only 5 consecutive amino acids from a Δ5 variable region sequence. Polypeptides comprising 7 amino acids, more preferably about 10 amino acids, more preferably about 15 amino acids, more preferably about 25 amino acids, more preferably about 50 amino acids, more preferably about 75 amino acids from the Δ5 light or heavy chain variable region are also included. Even more preferred are polypeptides comprising the entire Δ5 light or heavy chain variable region.

The invention includes modified Δ5 polypeptides which are functionally equivalent to Δ5, or have altered but measurable Δ5 immunologic activity. Fragments with improved Δ5 immunologic activity are preferred. Examples of modified polypeptides include polypeptides with conservative substitutions of amino acid residues, and one or more deletions or additions of amino acids which do not significantly deleteriously change the functional activity.

One example of this is Δ5 polypeptides comprising one or more amino acid substitutions in comparison with the prototype Δ5 sequence. Substitutions can range from changing or modifying one or more amino acids to complete redesign of a region, such as the variable region. Amino acid substitutions, if present, are preferably conservative substitutions that do not deleteriously affect folding or functional properties of the peptide. Groups of functionally related amino acids within which conservative substitutions may be made are glycine/alanine; valine/isoleucine/leucine; asparagine/glutamine; aspartic acid/glutamic acid; serine/threonine/methionine; lysine/arginine; and phenylalanine/tryosine/tryptophan. Polypeptides of this invention may be in glycosylated or unglycosylated form, may be modified post-translationally (e.g., acetylation, and phosphorylation) or may be modified synthetically (e.g., the attachment of a labeling group).

The terms "peptide", "polypeptide" or "protein" are used interchangeably herein. The term "substantial identity", when referring to polypeptides, indicates that the polypeptide or protein in question is at least about 50% identical to an entire naturally occurring protein or a portion thereof, usually at least about 70% identical, and preferably at least about 95% identical.

Those skilled in the art will readily appreciate that the various adaptations of Δ5 described in this section may be combined in various fashions to yield other Δ5 polypeptides with desirable properties. In another example, a Δ5 scFv is fused to a cytokine, such as IL-2. All such combinations are contemplated in this invention.

The polypeptides of this invention can be made by any suitable procedure, including proteolysis of the Δ5 antibody, by recombinant methods or by chemical synthesis.

Δ5 polypeptides, especially shorter polypeptides up to about 50 amino acids, are conveniently made by chemical synthesis, based on the sequence data and other information provided herein.

Certain Δ5 polypeptides which are fragments of the whole molecule may alternatively be prepared from enzymatic cleavage of intact Δ5. Examples of proteolytic enzymes include, but are not limited to, trypsin, chymotrypsin, pepsin, papain, V8 protease, subtilisin, plasmin, and thrombin. Intact Δ5 can be incubated with one or more proteinases simultaneously or sequentially. Alternatively, or in addition, intact Δ5 can be treated with disulfide reducing agents. Peptides may then be separated from each other by techniques known in the art, including but not limited to, gel filtration chromatography, gel electrophoresis, and reverse-phase HPLC.

A Δ5 polypeptide can also be made by obtaining a polynucleotide encoding it according to the information provided elsewhere in this application, and introducing it into a suitable expression system. Typically, polynucleotides encoding a Δ5 polypeptide are ligated into an expression vector under control of a suitable promoter and used to genetically alter the intended host cell. Both eukaryotic and prokaryotic host systems can be used. The polypeptide is then isolated from lysed cells or from the culture medium and purified to the extent needed for its intended use. Examples of prokaryotic host cells appropriate for use with this invention include *Escherichia coli*. Examples of eukaryotic host cells include avian, insect, plant, and animal cells such as COS7, HeLa, CHO cells and myeloma cells.

In certain applications, such as when a Δ5 polypeptide is expressed in a suitable storage medium such as a plant seed, the Δ5 polypeptide can be used without purification. Fiedler et al. (1995) Biotechnology 13:1090–1093. For most applications, it is generally preferable that the polypeptide is at least partially purified from other cellular constituents. Preferably, the polypeptide is at least about 50% pure as a weight percent of total protein. More preferably, the protein is at least about 50–75% pure. For clinical use, the polypeptide is preferably at least about 95% pure.

As used herein, the terms "isolated", "substantially pure" and "substantially homogeneous" are used interchangeably and describe a protein that has been separated from components which naturally accompany it. Typically, a protein is substantially pure when at least about 60 to 75% of a sample exhibits the same amino acid sequence. Minor variants or chemical, modifications typically share the same sequence. A substantially purified protein will typically comprise at least about 85 to 90% of a protein sample, more usually at least about 95% and preferably will be over about 99% pure. Protein purity or homogeneity may be indicated by a number of means well known in the art, such as polyacrylamide gel electrophoresis (PAGE) of a protein sample, followed by visualizing a single polypeptide band on a polyacrylamide gel upon staining. For certain purposes, high resolution will be needed and HPLC or a similar means for analysis utilized.

A polypeptide is substantially free of naturally associated components when it is separated from the native contaminants which accompany it in its natural state. Thus, a polypeptide which is chemically synthesized or synthesized in a cellular system different from the cell from which it naturally originates will be substantially free from its naturally-associated components. Proteins may be purified to substantial homogeneity by standard techniques well known in the art, including selective precipitation with such substances as ammonium sulfate, column chromatography, immunopurification methods, and others. See, for instance, R. Scopes, Protein Purification: Principles and Practice, Springer-Verlag: N.Y. (1982).

The invention further encompasses polynucleotides (or nucleic acids) encoding the Δ5 antibodies or portions thereof. The term, nucleic acids, as used herein, may be DNA or RNA either coding or noncoding strands. When referring to nucleic acids, the term "substantial identity" indicates that the sequences of two nucleic acids, or designated portions thereof, when optimally aligned and compared, are identical, with appropriate nucleotide insertions or deletions, in at least about 80% of the nucleotides, usually at least about 90% to 95%, and more preferably at least about 98 to 99.5% of the nucleotides.

Alternatively, substantial nucleic acid sequence identity exists when a nucleic acid segment will hybridize under selective hybridization conditions, to a complement of another nucleic acid strand.

"Substantially complementary" similarly means that one nucleic acid is identical to, or hybridizes selectively to, another nucleic acid. Typically, selective hybridization will occur when there is at least about 55% identity over a stretch of at least 14–25 nucleotides, preferably at least about 65% identity, more preferably at least about 75%, and most preferably at least about 90% identity. See, Kanehisa (1984) Nucl. Acids Res. 12:203.

Stringent hybridization conditions will typically include salt concentrations of less than about 1M, more usually less than about 500 mM and preferably less than about 200 mM. Temperature conditions will typically be greater than 22° C., more typically greater than about 30° C. and preferably in excess of about 37° C. As other factors may dramatically affect the stringency of hybridization, including base composition and size of the complementary strands, presence of organic solvents and extent of base mismatching, the combination of parameters is more important than the absolute measure of any one alone.

Hybridization reactions can be performed under conditions of different "stringency". Conditions that increase stringency of a hybridization reaction are published. See, for example, Sambrook and Maniatis. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15M NaCl and 15 mM citrate buffer) and their equivalent using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

"Isolated" or "substantially pure", when referring to nucleic acids, refer to those that have been purified away from other cellular components or other contaminants, e.g., other cellular nucleic acids or proteins, by standard techniques, including alkaline/SDS (sodium dodecyl sulfate) treatment, CsCl banding, column chromatography, and other methods well known in the art. See, F. Ausubel et al. (1987) ed. *Current Protocols in Molecular Biology*, Greene Publishing and Wiley-Interscience, New York.

A nucleic acid is "operably linked" when it is placed into a functional relationship with another nucleic acid sequence. For instance, a promoter or enhancer is operably linked to a coding sequence if it affects the transcription of the sequence. Generally, operably linked means that the nucleic acid sequences being linked are contiguous and, where necessary to join two protein coding regions, contiguous and in reading frame.

The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al. 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al. eds., 1987); "PCR: The Polymerase Chain Reaction", (Mullis et al. eds., 1994); "Current Protocols in Immunology" (J. E. Coligan et al. eds., 1991).

These techniques are applicable to the production of the polynucleotides and polypeptides of the invention, and, as such, may be considered in making and practicing the invention. Particularly useful techniques for particular embodiments will be discussed in the sections that follow.

The invention provides various polynucleotides encoding the antibody Δ5 or specific binding fragments of Δ5, based on the polynucleotide sequences provided herein. Various embodiments are described in this section, comprising a number of different combinations of the Δ5 heavy or light chain variable region sequences. In general, a Δ5 polynucleotide of this invention encodes at least one feature that is unique to the Δ5 molecule (in comparison with other immunoglobulins). Preferably, this feature is related in some way to an immunological reactivity of Δ5.

The invention encompasses a polynucleotide encoding a portion of the Δ5 light or heavy chain variable regions, comprising at least about 70 consecutive nucleotides, preferably at least about 80 consecutive nucleotides, more preferably at least about 100 consecutive nucleotides, even more preferably at least about 150 nucleotides, e.g., of SEQ ID NOS:1, 3, 5, 7, 9, 11, 13 and 15. The invention further encompasses polynucleotides complementary to the coding polynucleotides.

The invention also encompasses polynucleotides encoding for specific binding fragments of Δ5 and functionally equivalent fragments thereof which may enhance, decrease or not significantly affect properties of the polypeptides encoded thereby. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide.

The Δ5 polynucleotides of the invention may comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention.

Useful polynucleotides encoding fragments of Δ5 may be identified by generating polynucleotide fragments (based on SEQ ID NOS:1, 3, 5, 7, 9, 11, 13, or 15, for example) and testing the polypeptides encoded thereby for a function of interest. Alternatively, the polypeptide fragment encoded by a particular polynucleotide may be prepared and tested for a function of interest. Alternatively, given a Δ5 polypeptide with desirable properties, a polynucleotide could be designed that encodes it.

Included in all these embodiments are polynucleotides with encoding regions for Δ5 polymers, fusion proteins, HuAbs, single-chain variable regions, and other particular polypeptides of interest. These polypeptides are described in more detail herein.

The invention also provides polynucleotides covalently linked with a detectable label. Such polynucleotides are useful, for example, as probes for detection of related nucleotide sequences.

The polynucleotides of this invention can be obtained using chemical synthesis, recombinant cloning methods, PCR, or any combination thereof.

Methods of chemical polynucleotide synthesis are well known in the art and need not be described in detail herein. One of skill in the art can use the sequence data provided herein to obtain a desired polynucleotide by employing a DNA synthesizer or by ordering from a commercial service.

Alternatively, Δ5 polynucleotide sequences can be obtained from a Δ5 antibody producing cell line, Δ5 cloning vector, or Δ5 expression vector. RNA or DNA encoding the desired sequence may be isolated, amplified, and processed by standard recombinant techniques. Such techniques include digestion with restriction nucleases, and amplification by polymerase chain reaction (PCR), or a suitable combination thereof. PCR technology is for instance, described in U.S. Pat. Nos. 4,683,195, 4,800,159, 4,754,065 and 4,683,202. A polynucleotide comprising a desired sequence can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. Amplified DNA can be isolated from the host cell by standard methods. See, e.g., Sambrook et al. (1989). RNA may also be obtained from transformed host cell, it may be obtained by using an DNA-dependent RNA polymerase.

The polynucleotides of this invention have several uses. Δ5 polynucleotides are useful, for example, in expression systems for the production of Δ5 or Δ5 fragments. They are also useful as hybridization probes to assay for the presence of Δ5 polynucleotide or related sequences in a sample using methods well known to those in the art. Further, Δ5 polynucleotides are also useful as primers to effect amplification of desired polynucleotides. The polynucleotides of this invention are also useful in pharmaceutical compositions including vaccines and for gene therapy.

The invention further encompasses vectors comprising the Δ5 polynucleotides. "Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in E. coli for cloning and construction, and in eukaryotic cells for expression.

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxic substances, e.g., ampicillin, neomycin, methotrexate; (b) complement auxotrophic deficiencies; or (c) supply critical nutrients not available from complex media. The choice of the proper marker gene will depend on the host cell, and appropriate genes for different hosts are known in the art. Cloning and expression vectors typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, or may carry genes for a marker that can be used in selecting clones containing the vector. Suitable examples include, but are not limited to, plasmids and bacterial viruses, e.g., pUC18, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide encoding a Δ5 polypeptide of interest. The polynucleotide encoding the Δ5 polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from the Δ5 gene, or they may be heterologous (i.e., derived from other genes or other organisms). A polynucleotide sequence encoding a signal peptide can also be included to allow a Δ5 polypeptide to cross or lodge in cell membranes or be secreted from the cell. A number of expression vectors suitable for expression in eukaryotic cells including yeast, avian, and mammalian cells are known in the art. One example of an expression vector is pcDNA3 (Invitrogen, San Diego, Calif.), in which transcription is driven by the cytomegalovirus (CMV) early promoter/enhancer. This vector also contains recognition sites for multiple restriction enzymes for insertion of the Δ5 polynucleotide of interest. Another example of an expression vector (system) is the baculovirus/insect system.

The claimed vectors can be used for expression of recombinant polypeptides as well as a source of Δ5 polynucleotides. Cloning vectors can be used to obtain replicate copies of the Δ5 polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express Δ5 polypeptides in an individual and thus have intact cells capable of synthesizing the polypeptide, such as in gene therapy. Suitable cloning and expression vectors include any known in the art, e.g., those for use in bacterial, mammalian, yeast and insect expression systems. Specific vectors and suitable host cells are known in the art and need not be described in detail herein. For example, see Gacesa and Ramji (1994) Vectors, John Wiley & Sons.

Other embodiments of this invention are host cells transformed with Δ5 polynucleotides and vectors comprising Δ5 polynucleotide sequences, as described above. Both prokaryotic and eukaryotic host cells may be used. Prokaryotic hosts include bacterial cells, for example E. coli and Mycobacteria. Among eukaryotic hosts are yeast, insect, avian, plant and mammalian cells. Host systems are known in the art and need not be described in detail herein. One example of a mammalian host cell is NS0, obtainable from the European Collection of Cell Cultures (England). Transfection of NS0 cells with a plasmid, for example, which is driven by a CMV promoter, followed by amplification of this plasmid in using glutamine synthetase provides a useful system for protein production. Cockett et al. (1990) Bio/Technology 8:662–667.

The host cells of this invention can be used, for a variety of purposes, including, but not limited to, repositories of Δ5 polynucleotides, vehicles for production of Δ5 polynucleotides and polypeptides and as vehicles for expression of Δ5 polypeptides.

Mammalian cell lines are often used as host cells for the expression of polypeptides derived from eukaryotes. Propagation of mammalian calls in culture is per se well known. See Tissue Culture, Academic Press, Kruse and Patterson, eds. (1973). Host cell lines may also include such organisms as bacteria (e.g., E. coli or Bacillus subtilis), yeast, filamentous fungi, plant cells, or insect cells, among others.

"Transformation" refers to the introduction of vectors containing the nucleic acids of interest directly into host cells by well known methods. Transformation methods, which vary depending on the type of host cell, include electroporation; transfection employing calcium chloride, rubidium chloride calcium phosphate, DEAE-dextran, or other substances; microprojectile bombardment; lipofection; infection (where the vector is an infectious agent); and other methods. See generally, Sambrook et al. (1989) and Ausubel et al., (ed.), (1987). Reference to cells into which the nucleic acids described above have been introduced is meant to also include the progeny of such cells.

Once introduced into a suitable host cell, for example, E. coli or COS-7, expression of a Δ5 polypeptide can be determined using any of the assays described herein. For example, presence of Δ5 polypeptide can be detected by RIA or ELISA of the culture supernatant or cell lysates.

The invention also encompasses pharmaceutical compositions comprising a Δ5 antibody and a pharmaceutically acceptable excipient. The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the Δ5 antibody dissolved or suspended in an pharmaceutically acceptable excipient or carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of Δ5 antibody in the pharmaceutical compositions can vary widely, i.e., from less than about 1%, usually at or at least about 10–15% to as much as 50% or more, by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of Δ5 antibody. Actual methods for preparing parenterally administrable compounds are known or apparent to those skilled in the art and are described in more detail in, for example, Remington's Pharmaceutical Science 17 ed., Mack Publishing Company, Easton, Pa. (1985).

In addition to pharmaceutical compositions, the invention further encompasses various devices for local delivery of the antibodies to the effected site. These devices include, but are not limited to, coated stents or grafts (such as Dacron, etc.). Methods of coating these devices are known in the art as exemplified by the method of heparin coating described by Serruys et al. (1996) Circ. 93:412–422. Coated stents are particularly useful in treating restenosis.

The invention also encompasses methods of treatment of disorders related to PDGF activity. As used herein, "treatment" refers to clinical intervention in an attempt to alter the natural course of the individual being treated, and may be performed either for prophylaxis or during the course of clinical pathology. Desirable effects include preventing occurrence or recurrence of disease, alleviation of symptoms, diminishment of any direct or indirect pathological consequences of the disease, decreasing the rate of disease progression, amelioration or palliation of the disease state, and remission or improved prognosis. An "individual" is a vertebrate, preferably a mammal, more preferably G64 a human. Mammals include, but are not limited to, humans, farm animals, sport animals, and pets.

The "pathology" associated with a disease condition is any condition that compromises the well-being, normal physiology, or quality of life of the affected individual. This may involve, but is not limited to, destructive invasion of affected tissues into previously unaffected areas, growth at the expense of normal tissue function, irregular or suppressed biological activity, aggravation or suppression of an inflammatory or immunological response, increased susceptibility to other pathogenic organisms or agents, and undesirable clinical symptoms such as pain, fever, nausea, fatigue, mood alterations, and such other features as may be determined by an attending physician. For instance, in the case of restenosis, the pathology is characterized by a decrease in the diameter of the lumen of a vessel wall. Suitable indications include those related to PDGF-mediated diseases involving proliferation of smooth muscle cells. These include, but are not limited to, restenosis following angioplasty, endarterectomy or other procedures that remove atherosclerotic plaques from blood vessels, and acute vascular injuries such as anastomosis of a vascular graft and those occurring during organ transplantation.

An "effective amount" is an amount sufficient to effect a beneficial or desired clinical result. An effective amount can be administered in one or more doses. For purposes of this invention, an effective amount of Δ5 is, e.g., an amount that lessens or prevents intimal hyperplasia after invasive treatment of a vessel. In terms of treatment, an effective amount is an amount that is sufficient to palliate, ameliorate, stabilize, reverse or slow the progression of the disease, or otherwise reduce the pathological consequences of the disease. Preferably, the antibodies are used in prevention or reduction of restenosis after coronary angioplasty, e.g., by balloon dilatation.

Therapeutically effective doses will depend on, e.g., the nature of the Δ5 antibody composition, the manner of administration, the stage and severity of the disease being treated, the weight and general state of health of the patient, and the judgment of the prescribing physician, but will generally range from about 0.01 mg/kg to about 100.0 mg/kg of antibody per dose, with dosages of from about 0.1 mg/kg to about 10 mg/kg of antibody per dose being more commonly used.

It must be kept in mind that the Δ5 antibody may be employed in serious disease states, that is, life-threatening or potentially life-threatening situations. In such cases, it is possible and may be felt desirable by the treating physician to administer substantial excesses of these compositions. Thus, human Δ5 antibodies or substantially human Δ5 antibodies are most preferred under these circumstances.

Single or multiple administrations of the compositions can be carried out with dose levels and pattern being selected by the treating physician. In any event, the pharmaceutical formulations should provide a quantity of Δ5 antibody sufficient to effectively treat the patient. Administration should begin at the first indication of undesirable cellular proliferation or shortly after diagnosis, and continue until symptoms are substantially abated and for a period thereafter. In well established cases of disease, loading doses followed by maintenance doses will be required. Preferably, the antibodies are administered by single or repeated intravenous injections. The use of infusions is less likely, but still feasible.

In addition to systemic administration, the invention also encompasses methods of local administration. For instance, the compositions can be directly coated onto the vessel wall during surgery or other treatment. For a more long lasting local delivery, the use of coated stents and grafts as described above, is preferred. For inhibition of stenosis in vascular grafts, Δ5 antibodies can be covalently attached to the graft through their constant regions or incorporated into the graft in slow-release formulations. These methods of drug delivery are known in the art and need not be described in detail herein.

The Δ5 antibodies of this invention can be prepared in several ways.

For example, the cells producing the antibodies can be cultured in a suitable medium, and spent medium can be used as an antibody source. Optionally, matrix-coated channels or beads and cell co-cultures may be included to enhance growth of antibody-producing cells. For the production of large amounts of antibody, it is generally convenient to obtain an ascites fluid. The method of raising ascites generally comprises injecting hybridoma cells into an immunologically naive histocompatible or immunotolerant mammal, especially a murine. The mammal is optionally primed for ascites production by prior administration of a suitable composition; for example, Pristane.

Alternatively, Δ5 antibodies or, particularly, specific binding fragments thereof, can be chemically synthesized using sequence data and other information provided in this disclosure, in conjunction with standard methods of protein synthesis. A suitable method is the solid-phase Merrifield technique. Automated peptide synthesizers are commercially available, such as those manufactured by Applied Biosystems, Inc. (Foster City, Calif.).

Δ5 may also be obtained by employing routine recombinant methods such as described in Sambrook et al. (1989). For instance, using the sequences and information provided herein, a polynucleotide encoding either the Δ5 heavy or light chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of Δ5 may be produced separately, and then combined by disulfide bond rearrangement. Alternatively, vectors with separate polynucleotides encoding each chain of Δ5, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The Δ5 thus produced in the host cell can be purified using standard techniques in the art. A polynucleotide encoding Δ5 for use in the production of Δ5 by any of these methods can in turn be obtained from the hybridoma producing Δ5, or be produced synthetically or recombinantly from the DNA sequences provided herein.

Methods of antibody production and isolation are well known in the art. See, for example, Harlow and Lane (1988) *Antibodies: A Laboratory Manual*, Cold Spring Harbor Laboratory, N.Y. Purification methods may include salt precipitation (for example, with anmnonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-antibody. Δ5 may also be purified on affinity columns comprising a PDGF-R β antigen; for example, in the form of a purified Ab1 or Ab3.

If Δ5 is to be administered to an individual, it is preferably at least 90% pure, more preferably it is at least 95% pure, even more preferably it is at least 98% pure and free of pyrogens and other contaminants. In this context, the percent purity is calculated as a weight percent of the total protein content of the preparation, and does not include constituents which are deliberately added to the composition after the Δ5 is purified.

The invention also encompasses methods of detecting PDGF-R β antigen in a biological sample. The methods include obtaining a biological sample, contacting the sample with the Δ5 antibody under conditions that allow antibody antigen binding and detecting binding, if any, of the antibody to the antigen.

The Δ5 polypeptides produced according to the present invention may be of the IgG, IgM, IgA or IgD isotype, and may further be any of the appropriate subclasses thereof, including, but not limited to, $IgG_1$, $IgG_2$, $IgG_3$ or $IgG_4$. Using recombinant techniques, "class-switching" of the Δ5 polypeptides can be readily accomplished. In this method, polynucleotides encoding the constant regions which determine the isotype of the immunoglobulin molecule of interest are replaced by polynucleotides encoding a desired isotype or subclass, as generally described in European patent publication EP 314,161. Class-switched immunoglobulins may also be isolated by selecting cells that have undergone spontaneous switching using selection methods known in the art.

All nucleic acid and antibody manipulations, constructions and assays in the following examples were performed by methods known to those skilled in the art including oligonucleotide synthesis, PCR, and ELISA and flow cytometry. See, Sambrook et al. (1989); and Harlow et al. (1988).

The following examples are meant to illustrate, but not limit, the claimed invention.

EXAMPLE 1
Preparation of Soluble and Membrane-bound Forms of the PDGF β Receptor A gene encoding the PDGF-R β, lacking the nucleotides encoding several amino acids at the 5' end, was obtained from the American Type Culture Collection; the missing part including secretion signal sequence was constructed by oligonucleotide synthesis and used to reconstruct the entire gene. To produce a soluble form of PDGF-R β, the gene encoding the protein was truncated immediately before the transmembrane sequence and a stop codon followed by an XbaI restriction endonuclease site was inserted. This gene fragment within two XbaI sites was inserted into the plasmid pVk as described by Co et al. (1992) J. Immunol. 148:1149. The resulting plasmid was cotransfected by the calcium-phosphate procedure into Chinese hamster ovary (CHO) cells together with plasmid pVg1 (Co et al. (1992)), which contains a DHFR gene. Clones expressing DHFR were selected, and were amplified by methotrexate selection. The most resistant clones were used for production of PDGF-R β.

The CHO cells expressing the truncated PDGF-R β were then grown in roller bottles. When confluent, cells were washed and incubated in protein-free media for 72 hours. The media supernatant was harvested and bound to lentil lectin-Sepharose, which binds specifically to α-D-mannosyl residues of glycoproteins, and eluted with α-D-mannose. The eluant containing PDGF-R β was dialyzed and concentrated to approximately 300 μg/ml. The purified protein was more than 95% pure based on SDS-PAGE gel analysis. Purified PDGF BB was obtained from Boehringer Mannheim.

It has been shown that CHO cells transfected with the PDGF receptor will undergo increased DNA synthesis and cell proliferation in the presence of PDGF. Escobedo et al. (1988) J. Biol. Chem. 263:1482. A cell line (CHO C4) that expresses PDGF-R β and undergoes PDGF-mediated proliferation in this manner was constructed by transfecting a plasmid containing the PDGF-R β gene into CHO DHFR⁻ cells (ATCC CRL 9096) using the calcium-phosphate method essentially as described by Chen and Okayama, Mol. Cell. Biol. 7:2745 (1987). In addition, plasmid DNA was also introduced into the Sp2/0 cell line by electroporation, and cells selected for resistance to mycophenolic acid. The Sp2/0 transfectants express PDGF-R β on their surface as detected by flow cytometry, but PDGF BB does not stimulate proliferation of these cells.

EXAMPLE 2
Generation of MAbs to PDGF-R β

Outbred Swiss Webster mice were immunized with 50 μg purified soluble PDGF-R β in adjuvant via intraperitoneal injection. The mice received booster immunizations of 50 μg PDGF-R β every 1–2 weeks. Mice were bled one week following each boost and the sera were tested for reactivity with PDGF-R by ELISA. The mouse exhibiting the highest serum titer of anti-PDGF-R activity was sacrificed 3 days after receiving a final boost of 50 μg PDGF-R, and the spleen was removed. Cells were prepared from the spleen by standard methods and fused to cells of the murine myeloma cell line P3X63.Ag8.853 at a ratio of 5 spleen cells to 1 myeloma cell, using a Shimadzu somatic cell hybridizer (model SSH-2) set to the following parameters: Frequency: 1 Mhz, Voltage (AC): 40 V, Initial time: 30 sec, Pulse width: 20 μsec, Voltage (DC): 460 V, Field Strength: 2.30 kV/cm, Repeat interval: 1 sec, Pulses: 2, Voltage decrease rate: 100%, Final time: 30 sec.

Following electrofusion, the cells were resuspended in HYCDMEM (DMEM+10% FCS, 10% NCTC109) and dispersed into 96-well plates. Following a 24 hour incubation, a standard hypoxanthine aminopterin thymidine mixture (HAT) was added to the wells to select for hybrids, and the plates were incubated for an additional 10–14 days. Supernatants from wells positive for growth were tested for reactivity with PDGF-R β by an ELISA performed according to standard methods, in which purified soluble PDGF-R β was used to coat the wells of Immulon I 96-well plates, supernatants were added to the plates after blocking with BSA and washing, and goat anti-murine IgG - horseradish peroxidase conjugate was used as the second step reagent.

Cells from wells that exhibited reactivity were cloned, confirmed for reactivity by ELISA, and used to produce purified antibody. A number of MAbs reacting with soluble PDGF-R β, including two designated muM4TS.11 and muM4TS.22, were isolated in this manner.

To show that muM4TS.11 and muM4TS.22 bind to PDGF-R β expressed on the cell membrane, antibody-containing supernatants or purified antibodies (final concentration 0.1–1 μg/ml) were incubated with 250,000–500,000 CHO or CHO PDGF-R β transfectant cells for 30 min at 4° C. The cells were washed once in cold PBS and resuspended in 50 μl of PBS containing 10 μg/ml FITC-conjugated goat anti-mouse IgG and incubated for 30 min. After another wash, the cells were fixed by resuspension in 0.25 ml of paraformaldehyde in PBS, and analyzed for fluorescence by flow cytometry on a FACScan (Becton Dickinson). Both muM4TS.11 and muM4TS.22 specifically bound to CHO PDGF-R β transfectant cells but not to untransfected CHO cells.

EXAMPLE 3
Properties of MAbs to PDGF-R β

To determine the ability of muM4TS.11 and muM4TS.22 to block binding of PDGF BB to PDGF-R β, the following competitive binding experiments were performed. Transfectant cells expressing PDGF-R β were harvested, washed twice with cold DMEM, and resuspended at $10^6$ cells/ml in DMEM. The assay was carried out in triplicate by incubating 100 μl of the cell suspension with either: 1) no antibody (to determine total binding); 2) varying concentrations of antibody; or 3) 100 ng cold PDGF BB (to saturate specific binding sites and determine non-specific binding) for 15 minutes at 4° C. Each sample received 1.0 ng $^{125}$I-labeled PDGF BB, and was incubated for an additional 60 min at 4° C. Unbound $^{125}$I-labeled PDGF BB was separated from that bound to the cell by layering the sample over a mixture of 80% dibutylphthalate, 20% olive oil in a microfuge tube, and microfuging briefly to pellet the cells through the oil mixture. The tubes were placed in dry ice to freeze the contents, the tip of the tube containing the cell pellet was cut off into a vial, and radioactivity was determined in a gamma counter. As described below, muM4TS.22 competitively blocked binding of PDGF BB to PDGF-R β, but muM4TS.11 did not (see FIG. 10).

To determine the ability of muM4TS.11 and muM4TS.22 to block PDGF-mediated proliferation, a CHO transfectant cell line expressing PDGF-R β (CHO C4) was generated, as described above. Proliferation of this line, as measured by incorporation of $^3$H-thymidine by DNA synthesis, is stimulated several-fold by PDGF BB. The CHO PDGF-R β transfectants were plated in a 96-well tissue culture plate at about 50,000 cells/well in Ham's F-12+10% FCS and incubated for 1–2 days. The medium was removed, and the cells were washed once with serum-free medium (Ham's F-12+1 mg/ml BSA) and incubated in this media for 1–2 days to put them in a quiescent state. The appropriate amount of antibody in serum-free medium was added, and after 1–3 hours, 50 ng/ml PDGF BB was added. After overnight incubation, 1 μCi $^3$H-thymidine was added, and after a final 4 hour incubation, the cells were harvested using a PHD cell harvester (Cambridge Technology) and analyzed with a scintillation counter. As described below, both muM4TS.11 and muM4TS.22 at sufficient concentrations completely inhibited proliferation of the cells induced by PDGF BB (see FIGS. 6 and 12).

Similar experiments were also carried out using the human primary fibroblast cell line AG1523B, except DMEM media was used instead of Ham's F12, 300 ng/ml of PDGF BB was applied to the cells, and the final incubation after addition of $^3$H-thymidine was for 48 hr. muM4TS.11 and muM4TS.22 effectively inhibited the stimulation of proliferation by PDGF BB, again showing the ability of these antibodies to neutralize the biological activity of PDGF BB.

EXAMPLE 4
Cloning and Sequencing of muM4TS.22 Variable Region cDNAs

MuM4TS.22 heavy and light chain variable region cDNAs were cloned from mRNA isolated from hybridoma cells using anchored PCR according to the method described by Co et al. (1992). The 5' primers used annealed to poly-dG tails added to the cDNA, and the 3' primers to the constant regions. The amplified gene fragments were then inserted into pUC19, and several heavy and light chain clones were sequenced and respectively found to be the same. These variable region cDNA sequences and the amino acid sequences derived from them are shown in FIG. 1 (SEQ ID NOS:1–4).

EXAMPLE 5
Design of HuM4TS.22 Variable Regions

To retain the binding affinity of the muAb in the HuAb, the general procedures used were in accordance with those described by Queen et al. (1989) Proc. Natl. Acad. Sci. USA 86:10029; and WO 90/07861.

In order to ensure a functional HuAb, the computer program ENCAD was used to construct a molecular model of the muM4TS.22 variable domain, which was used to locate the amino acids in the muM4TS.22 framework that were close enough to the CDRs to potentially interact with them. To design the HuM4TS.22 heavy and light chain variable regions, the CDRs from muM4TS.22 were grafted into the framework regions of the human IC4 antibody. At framework positions where the computer model suggested significant contact with the CDRs, the amino acids from the muAb were substituted for the original human framework amino acids. For HuM4TS.22, this was done at residues 27, 29, 30, 37, 48, 67, 71, and 78 of the heavy chain and at residue 70 of the light chain. Also, framework residues that occurred only rarely at their positions in the database of HuAbs were replaced by a human consensus amino acid at those positions. For HuM4TS.22 this was done at residues 40, 73, 83, and 85 of the heavy chain and at residues 65 and 73 of the light chain.

The final sequence of HuM4TS.22 heavy and light chain variable regions is shown in FIG. 2 (SEQ ID NOS:5–8). However, many of the potential CDR-contact residues are amenable to substitutions of other amino acids that may still allow the antibody to retain substantial affinity to the antigen. Table 1 lists a number of positions in the framework where alternative amino acids may be suitable (LC=light chain, HC=heavy chain).

TABLE 1

| Position | HuM4TS.22 | Alternatives |
|---|---|---|
| LC-70 | G | D |
| HC-30 | T | S |
| HC-37 | V | I |
| HC-48 | L | I |
| HC-67 | L | V |
| HC-83 | S | I |

Likewise, many of the framework residues not in contact with the CDRs in the HuM4TS.22 heavy and light chains can accommodate substitutions of amino acids from the corresponding positions of the human IC4 antibody, from other HuAbs, from muM4TS.22, or from other muAbs, without significant loss of the affinity or non-immunogenicity of the HuAb. Table 2 lists a number of additional positions in the framework where alternative amino acids may be suitable.

TABLE 2

| Position | HuM4TS.22 | Alternatives |
|----------|-----------|--------------|
| LC-5     | T         | N            |
| HC-1     | Q         | E            |
| HC-73    | T         | L, I, M      |
| HC-74    | S         | A, T         |

Selection of combinations of alternative amino acids might be used to produce versions of HuM4TS.22 that have varying combinations of affinity, specificity, non-immunogenicity, ease of manufacture, and other desirable properties. Thus, the examples in the above tables are offered by way of illustration, not of limitation.

EXAMPLE 6
Construction of HuM4TS.22

Once the humanized variable region amino acid sequences had been designed as described above, genes were constructed to encode them, including signal peptides, splice donor signals and appropriate restriction sites. Each variable region gene was constructed and amplified using ten overlapping synthetic oligonucleotides in four steps as show in FIG. 3: (1) the four central pairs of overlapping oligonucleotides were denatured, allowed to anneal, and extended with the Klenow fragment of DNA polymerase to produce four longer overlapping oligonucleotides from eight shorter ones; (2) these four oligonucleotides were denatured and then similarly combined to form two overlapping fragments of DNA; (3) the resulting pair of oligonucleotides were likewise joined to form the central portion of the gene; and (4) the final two flanking oligonucleotides, each containing an XbaI restriction endonuclease site, were used in PCR to complete and amplify the genes.

The humanized variable region genes were inserted into human expression vectors containing either the human $C_\kappa$ gene (vector pVk; see Co et al. (1992)) or the human $C\gamma_4$ gene (vector pVg4, constructed from the pVg1 vector described in Co et al. (1992) by replacing the γ1 constant region gene with the γ4 constant region gene. Ellison and Hood, Proc. Natl. Acad. Sci. USA 79:1984 (1982). After the inserted variable region genes were sequenced, the two expression plasmids were linearized with BamnHI in preparation for transfection. Approximately 20 μg of each plasmid was transfected into 1×10⁷ Sp2/0-Ag14 cells (a murine myeloma cell line, ATCC CRL 1581) using a Gene Pulser apparatus (Bio-Rad) at 360 V and 25 μF according to the manufacturer's instructions. The cells were plated in a 96-well tissue culture plate, and after two days, selection medium (DMEM, 10% FCS, 1× penicillin-streptomycin (P/S) (Gibco), 1× HT supplement (Sigma), 0.25 mg/mil xanthine, 1 μg/ml mycophenolic acid) was applied. After approximately two weeks, the clones that appeared were screened for antibody production by ELISA. Antibody from a high-producing clone was prepared by growing the cells to confluency in regular medium (DMEM with 10% FCS), then replacing the medium with DMEM without serum but containing 0.1% Primatone, and culturing until the cells died. The culture supernatant was run over a protein A-Sepharose column (Pharmacia); antibody was eluted with 0.1M acetic acid, 150 mM NaCl, pH 3.0 and subsequently dialyzed against phosphate-buffered saline (PBS). The purity of the antibody was verified by PAGE and its concentration was determined by an $OD_{280}$ reading, assuming 1.3 mg of antibody protein has an $OD_{280}$ reading of 1.0.

EXAMPLE 7
Properties of HuM4TS.22

To show that the HuM4TS.22 binds specifically to PDGF-R β, antibody was incubated on ice for 30 minutes with Sp2/0 transfectant cells expressing PDGF-R β. The cells were washed with cold PBS, incubated for an additional 30 minutes with FITC-labeled goat-anti-human Ig (Tago Immunologicals) and analyzed by flow cytometry (FACS). 50 ng HuM4TS.22 stained the transfectant cells but did not stain untransfected Sp2/0 cells at all, indicating that the HuAb retains the ability to specifically bind to PDGF-R β.

Figure 4:
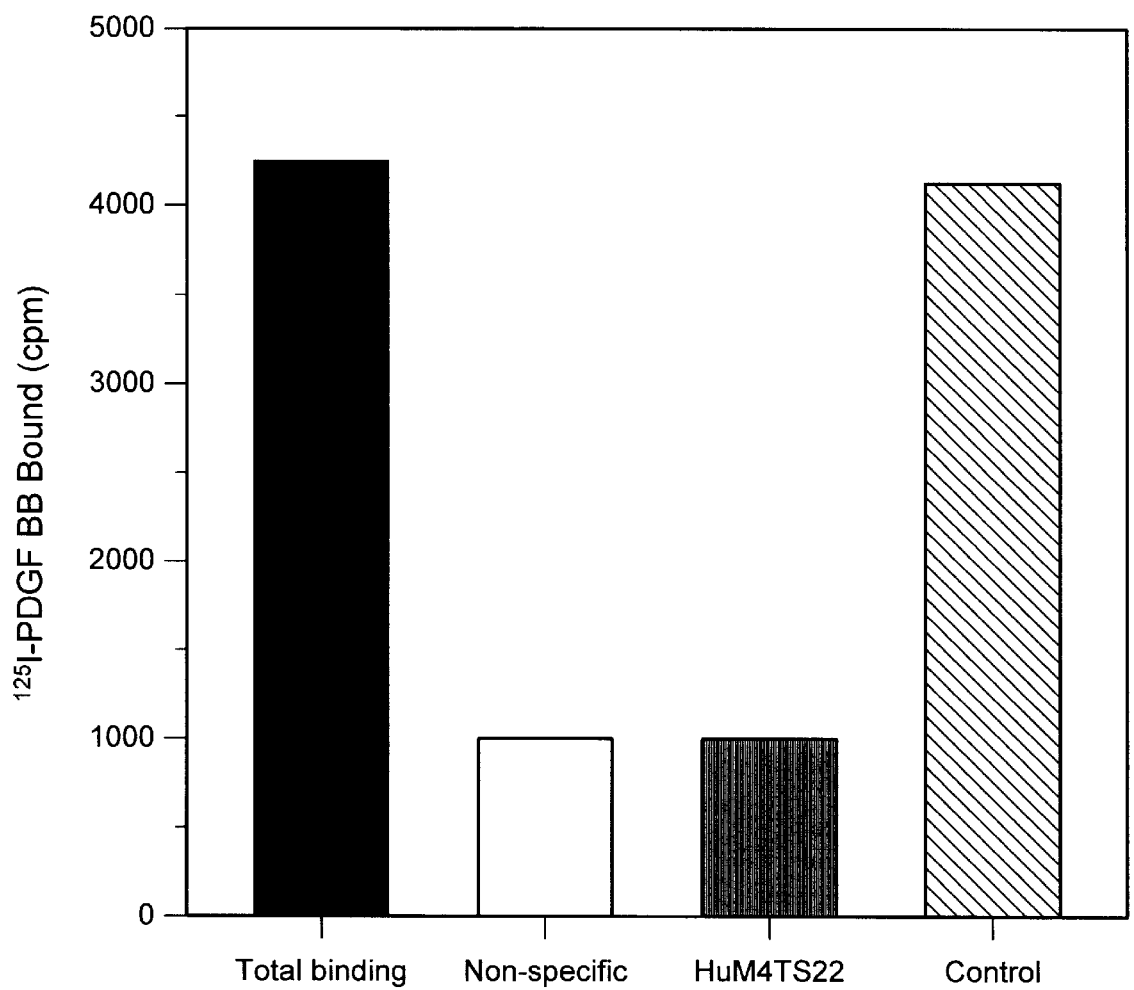
FIG. 4 is a bar graph depicting inhibition of $^{125}$I-PDGF BB binding to Sp2/0 transfectant cells expressing the PDGF-R β by HuM4TS.22 and controls.

To assess the ability of HuM4TS.22 to block the binding of PDGF BB to its receptor, competitive binding experiments of HuM4TS.22 with $^{125}$I-PDGF BB were performed according to the method described in Example 3. HuM4TS.22 reduced the binding of radiolabelled PDGF BB ligand to the PDGF-R β transfectant cells to the non-specific level, while the control antibody had no effect on binding, demonstrating that HuM4TS.22 has this ability (FIG. 4).

Figure 5:
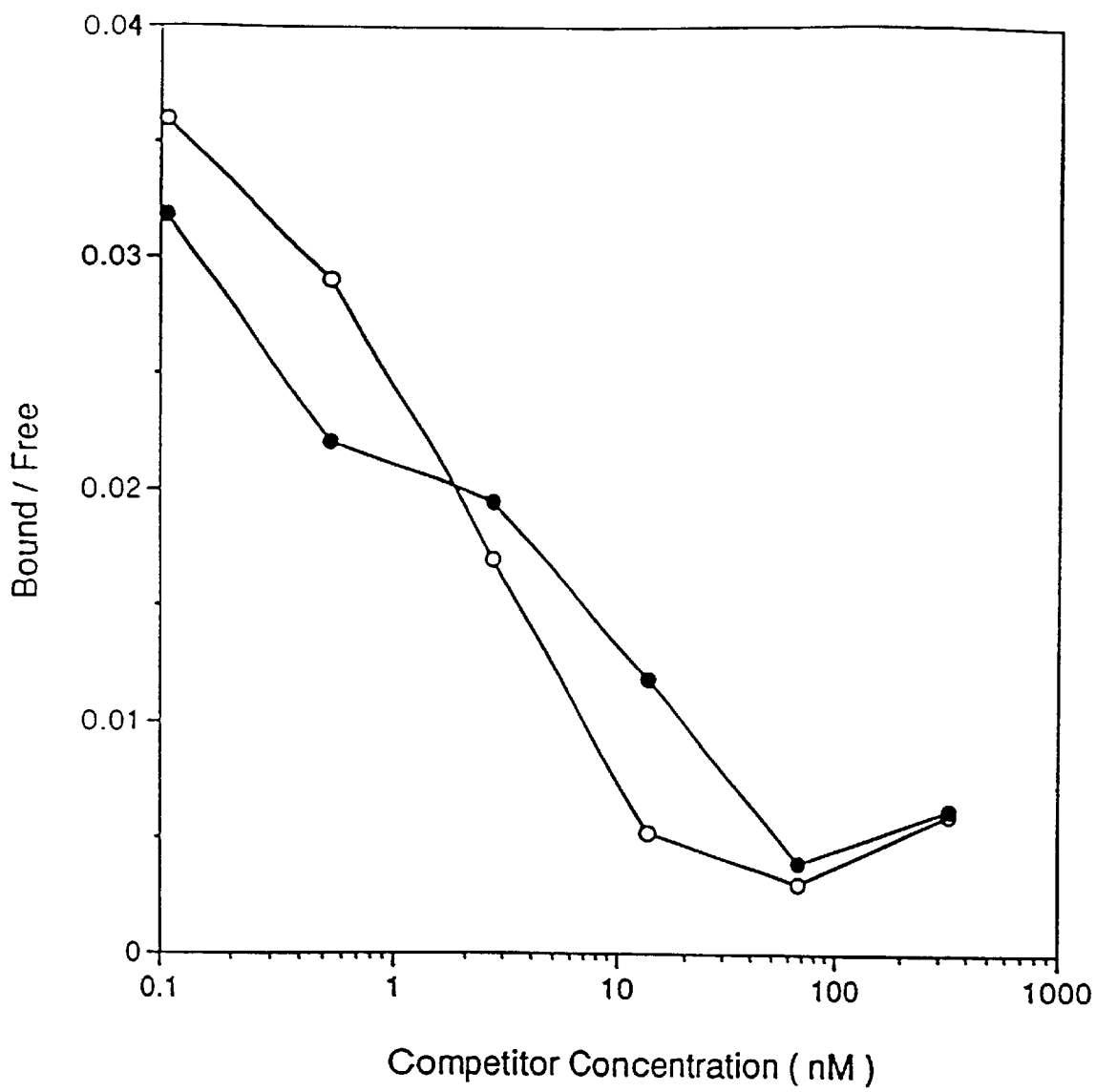
FIG. 5 is a graph depicting competitive binding of muM4TS.22 (closed circles) and HuM4TS.22 (open circles). Increasing concentrations of cold competitor antibodies were incubated with the Sp2/0 transfectants expressing PDGF-R β in the presence of radiolabeled tracer muM4TS.22, and the ratio of bound/free radioactivity determined. The results shown are mean values of triplicate samples.

To assess the ability of HuM4TS.22 to compete with muM4TS.22 for receptor binding, increasing concentrations of the two antibodies were respectively incubated on ice for one hour with Sp2/0 PDGF-R β transfectant cells and a fixed amount of tracer $^{125}$I-labeled muAb. The sample tubes were processed as in the blocking experiment just described. MuM4TS.22 and HuM4TS.22 competed with equal efficiencies (FIG. 5). The binding affinities calculated from the data were similar: $K_a=2.6\times10^8M^{-1}$ for muM4TS.22 and $4.0\times10^8M^{-1}$ for HuM4TS.22; thus the humanization procedure did not significantly alter the binding affinity of the original antibody.

Figure 6:
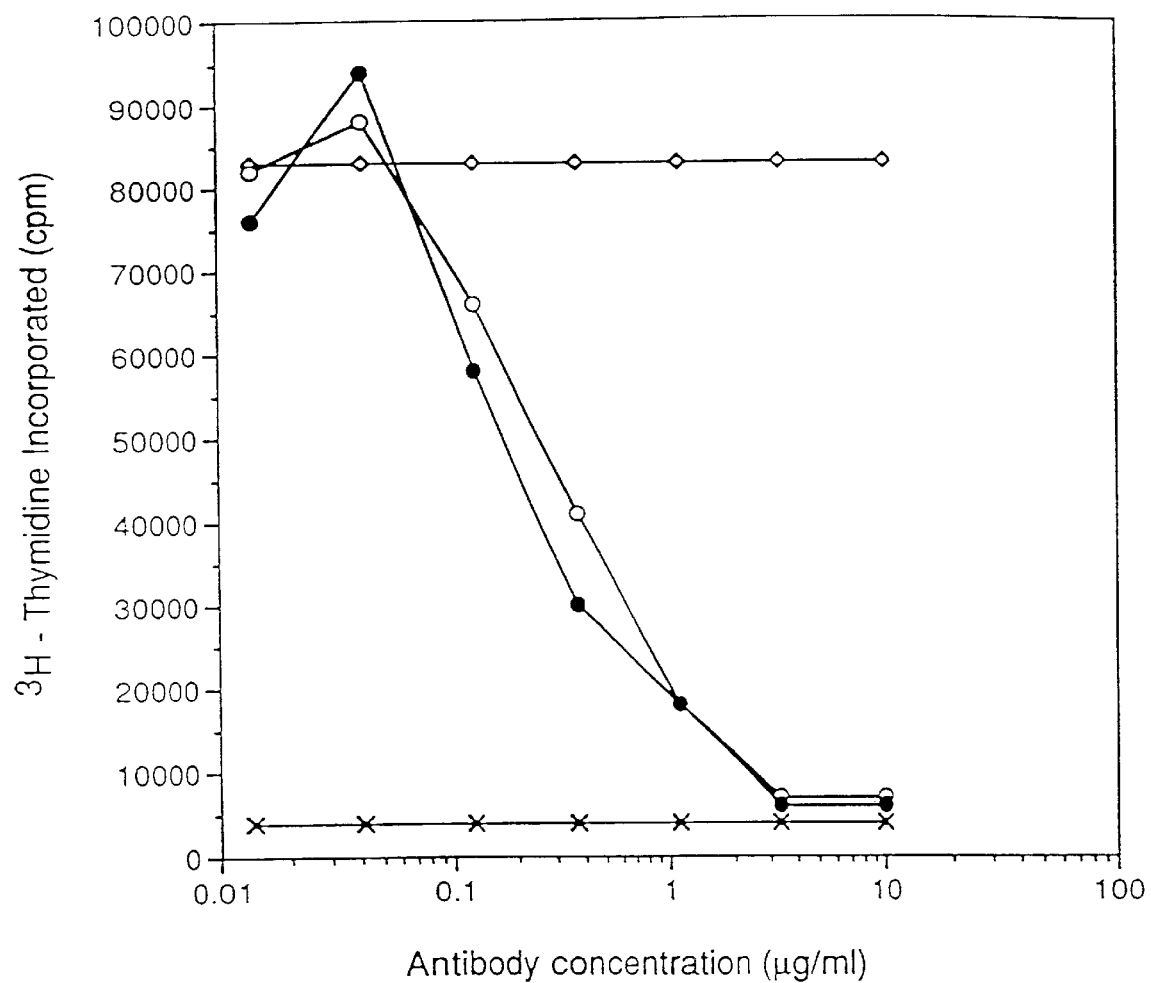
FIG. 6 is a graph depicting the inhibition of PDGF-induced proliferation of CHO cell transfectants expressing PDGF-R β (CHO C4) by muM4TS.22 (closed circles) and HuM4TS.22 (open circles). The cells were incubated with increasing concentrations of both M4TS.22 antibodies or no antibodies (open diamond) for 3 hours before 50 ng/ml PDGF BB was added, as described in the text. The no PDGF BB control is indicated by the Xs. The results shown are mean values of triplicate samples.

Both muM4TS.22 and HuM4TS.22 were tested for their ability to inhibit PDGF-mediated proliferation of CHO PDGF-R β transfectant cells (CHO C4 line), using the method described above in Example 3. As shown in FIG. 6, incubation of the cells with sufficient concentration of the antibodies almost completely inhibited the stimulation of proliferation by PDGF BB. Thus, HuM4TS.22 neutralized the functional activity of PDGF BB about equally as well as muM4TS.22.

EXAMPLE 8
Cloning and Sequencing of muM4TS.11 Variable Region cDNAs

Figure 7D:
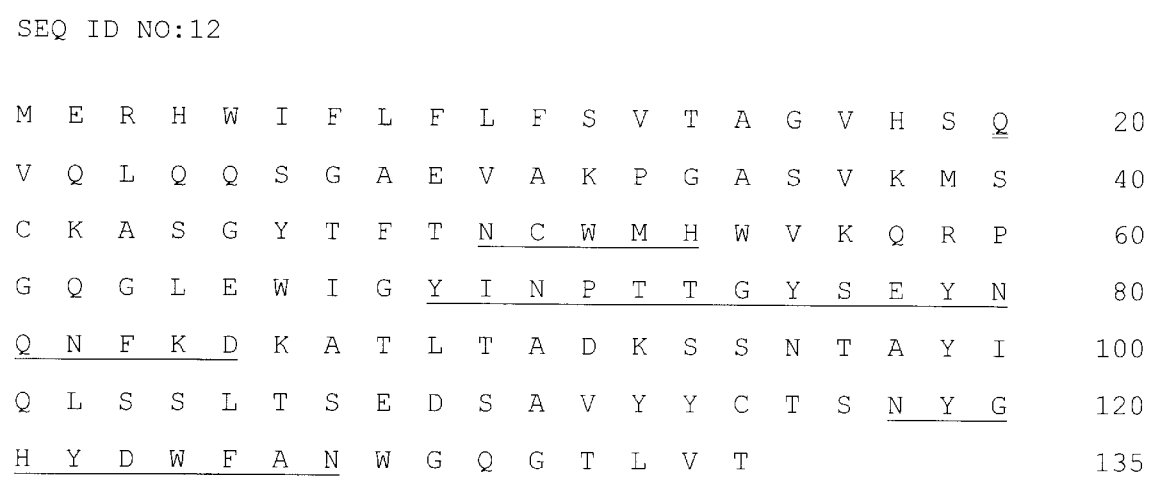

Murine heavy and light chain variable region cDNAs were cloned from MRNA isolated from hybridoma cells using anchored PCR. See, Co et al. (1992). The 5' primers used annealed to poly-dG tails added to the cDNA, and the 3' primers to the constant regions. The amplified gene fragments were then inserted into pUC18, and several heavy and light chain clones were sequenced and respectively found to be the same. These variable region cDNA sequences and the amino acid sequences derived from them are shown in FIG. 7 (SEQ ID NOS:9–12).

EXAMPLE 9
Design of HuM4TS.11 Variable Regions

To retain the binding affinity of the muAb in the HuAb, the general procedures of Queen et al. (1989) were followed as described in Example 5.

The computer program ENCAD was used to construct a molecular model of the muM4TS.11 variable domain, which was used to locate the amino acids in the muM4TS.11 framework that were close enough to the CDRs to potentially interact with them. To design the HuM4TS.11 heavy and light chain variable regions, the CDRs from muM4TS.11 were grafted into the framework regions of the human III-2R antibody. At framework positions where the computer model suggested significant contact with the CDRs, the amino acids from the muAb were substituted for the original human framework amino acids. For HuM4TS.11, this was done at residues 62 and 72 in the light chain and at residues 48, 67, 68, 97, and 98 in the heavy chain. Also, framework residues that occurred only rarely at their positions in the database of HuAbs were replaced by a human consensus amino acid at those positions. For HuM4TS.11 this was done at residue 47 in the light chain and at residues 16, 27, 30, and 116 in the heavy chain.

Figure 8D:
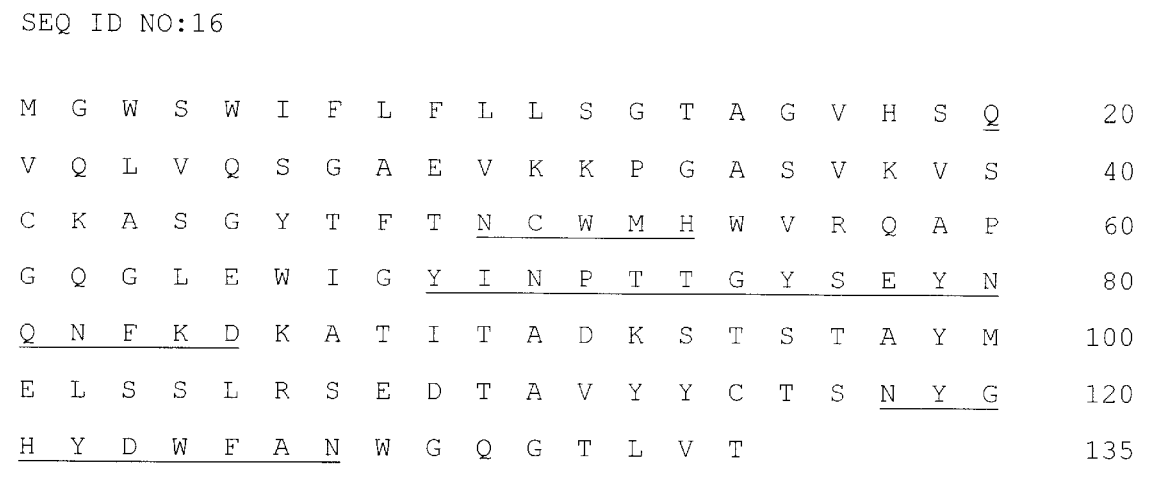

The final sequence of the HuM4TS.11 light and heavy chain variable regions is shown in FIG. 8 (SEQ ID NOS:13–16). However, many of the potential CDR-contact residues are amenable to substitutions of other amino acids that may still allow the antibody to retain substantial affinity to the antigen. Table 3 lists a number of positions in the framework where alternative amino acids may be suitable (LC=light chain, HC=heavy chain).

TABLE 3

| Position | HuM4TS.11 | Alternatives |
|---|---|---|
| LC-5 | T | I, V |
| LC-62 | I | V |
| HC-30 | T | S |
| HC-48 | I | M |
| HC-67 | K | R |
| HC-68 | A | V |
| HC-70 | I | L |

Likewise, many of the framework residues not in contact with the CDRs in the HuM4TS.11 light and heavy chains can accommodate substitutions of amino acids from the corresponding positions of the human III-2R antibody, from other HuAbs, from muM4TS.11, or from other muAbs, without significant loss of the affinity or non-immunogenicity of the HuAb. Table 4 lists a number of positions in the framework where alternative amino acids may be suitable.

TABLE 4

| Position | HuM4TS.11 | Alternatives |
|---|---|---|
| LC-3 | Q | V |
| LC-4 | M | L |
| HC-1 | Q | E |
| HC-75 | S | A, T |
| HC-81 | M | I, L |

Selection of combinations of alternative amino acids might be used to produce versions of HuM4TS.11 that have varying combinations of affinity, specificity, non-immunogenicity, ease of manufacture, and other desirable properties. Thus, the examples in the above tables are offered by way of illustration, not of limitation.

EXAMPLE 10
Construction of HuM4TS.11

Figure 9:
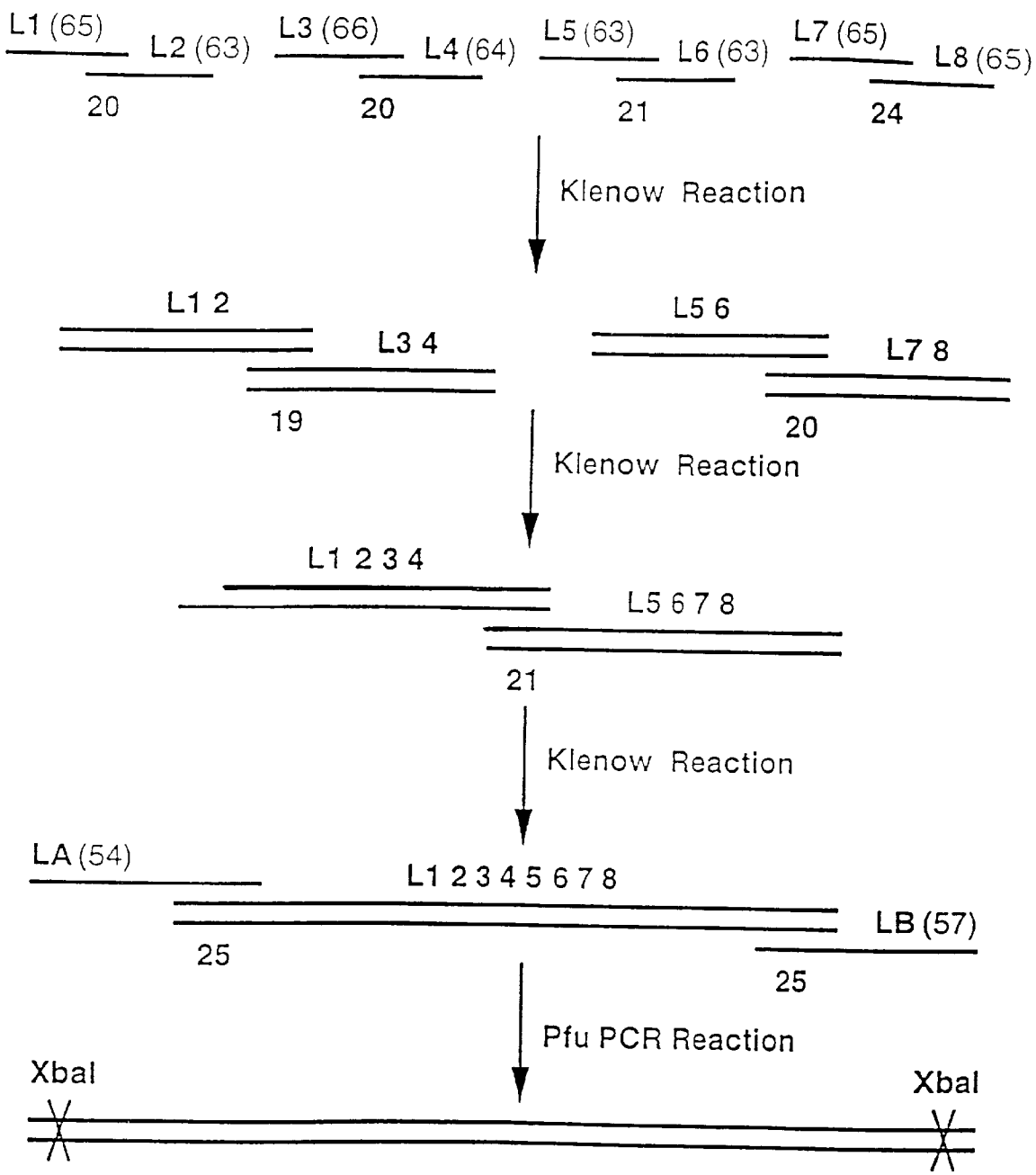
FIG. 9 is a schematic diagram depicting the construction of the HuM4TS.11 light chain variable region gene. The numbers in parentheses indicate the length of each oligonucleotide, and the numbers underneath the lines indicate the length of the overlapping region of each pair of oligonucleotides.

Once the humanized variable region amino acid sequences had been designed as described above, genes were constructed to encode them, including signal peptides, splice donor signals and appropriate restriction endonuclease sites. Each variable region gene was constructed and amplified using ten overlapping synthetic oligonucleotides in four steps as show in FIG. 9: (1) the four central pairs of overlapping oligonucleotides were denatured, allowed to anneal, and extended with the Klenow fragment of DNA polymerase to produce four longer overlapping oligonucleotides from eight shorter ones; (2) these four oligonucleotides were denatured and then similarly combined to form two overlapping fragments of DNA; (3) the resulting pair of oligonucleotides were likewise joined to form the central portion of the gene; and (4) the flanking two flanking oligonucleotides, each containing an XbaI restriction site, were used in PCR to complete and the amplify genes.

The humanized variable region genes were inserted into human expression vectors containing either the human $C_\kappa$ gene (vector pVk, see Co et al. (1992)) or the human $C\gamma_4$ gene (vector pVg4, constructed from the pVg1 vector described in Co et al. (1992) by replacing the γ1 constant region gene with the γ4 constant region gene. Ellison and Hood (1982). After the inserted variable region genes were sequenced, the two expression plasmids were linearized with BamnHI in preparation for transfection. Approximately 20 μg of each plasmid was transfected into 1×10$^7$ Sp2/0-Ag14 cells (a murine myeloma cell line, ATCC CRL 1581) using a Gene Pulser apparatus (Bio-Rad) at 360 V and 25 μF according to the manufacturer's instructions. The cells were plated in a 96-well tissue culture plate, and after two days, selection medium (DMEM, 10% FCS, 1× penicillin-streptomycin (P/S) (Gibco), 1× HT supplement (Sigma), 0.25 mg/mi xanthine, 1 μg/ml mycophenolic acid) was applied.

After approximately two weeks, the clones that appeared were screened for antibody production by ELISA. Antibody from a high-producing clone was prepared by growing the cells to confluency in regular medium (DMEM with 10% FCS, P/S), then replacing the medium with DMEM without serum but containing 0.1% Primatone, and culturing until the cells died. The culture supernatant was run over a protein A-Sepharose column (Pharmacia); antibody was eluted with 0.1M acetic acid, 150 mM NaCl, pH 3.0 and subsequently dialyzed against phosphate-buffered saline (PBS). The purity of the antibody was verified by running it on an acrylamide gel and its concentration was determined by an $OD_{280}$ reading, assuming 1.3 mg of antibody protein has an $OD_{280}$ reading of 1.0.

EXAMPLE 11
Properties of HuM4TS.11

To show that HuM4TS.11 binds specifically to PDGF-R β, antibody was incubated on ice for 30 minutes with Sp2/0 transfectant cells expressing PDGF-R β. The cells were washed with cold PBS, incubated for an additional 30 minutes with FITC-labeled goat-anti-human Ig (Tago Immunologicals) and analyzed by flow cytometry (FACS). 50 ng HuM4TS.11 stained the transfectant cells but did not stain untransfected Sp2/0 cells at all, indicating that the HuAb retains the ability to specifically bind to PDGF-R β. Neither an irrelevant control antibody nor the FITC-labeled goat antibody alone stained either cell type.

Figure 10:
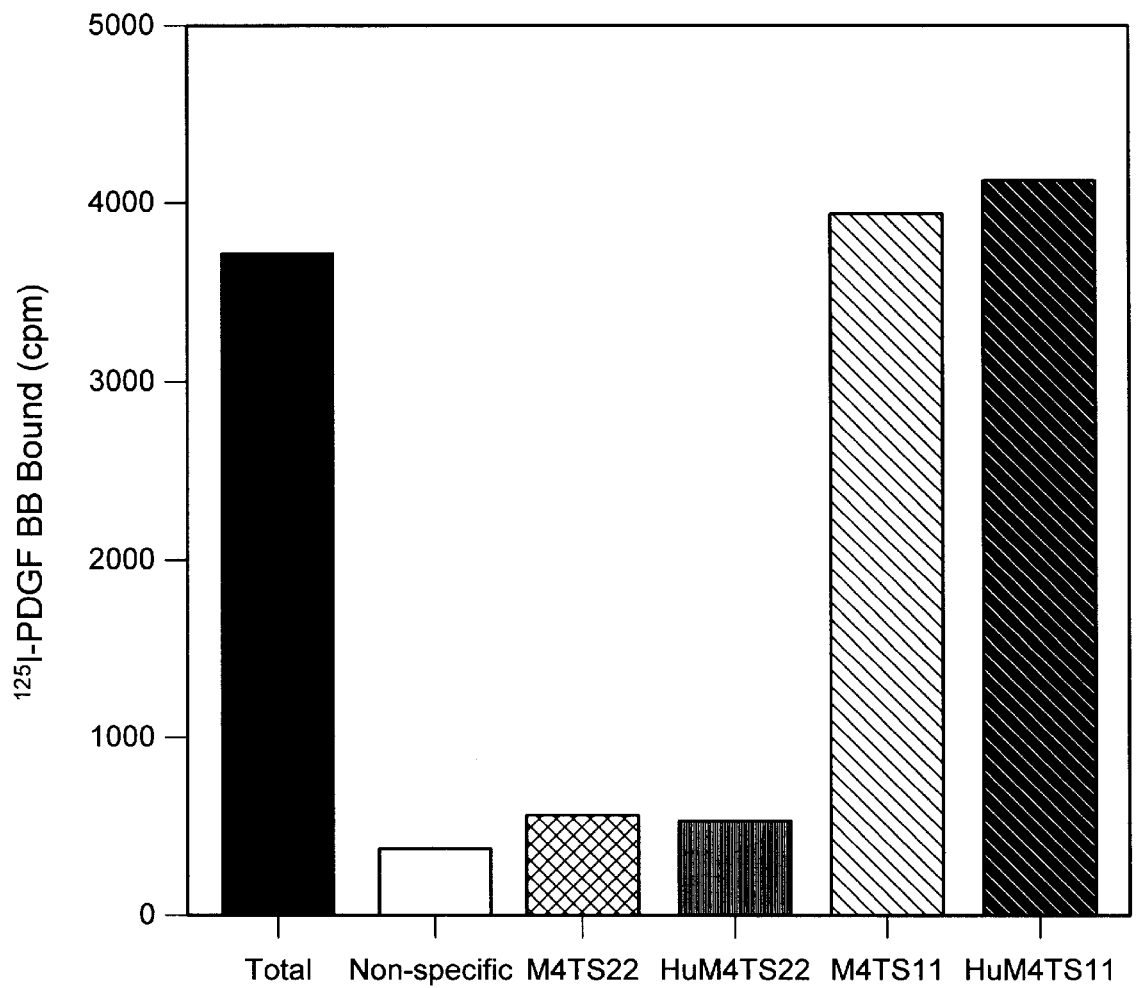
FIG. 10 is a bar graph depicting the inhibition of $^{125}$I-PDGF BB binding to Sp2/0 transfectant cells expressing the PDGF-R β by muM4TS.11 and HuM4TS.11 and controls.

To assess the ability of muM4TS.11 and HuM4TS.11 to block the binding of PDGF BB to the PDGF β receptor, competitive binding experiments of these antibodies with $^{125}$I-PDGF BB were performed according to the method described in Example 3. Surprisingly, neither muM4TS.11 nor HuM4TS.11 were able to inhibit binding of PDGF BB to its receptor (FIG. 10), despite their ability to neutralize the biological activity of PDGF BB as shown below. As positive controls, muM4TS.22 and HuM4TS.22 were included in the same experiment, and these antibodies did have the ability to block binding of PDGF BB to PDGF-R β (FIG. 10).

Figure 11:
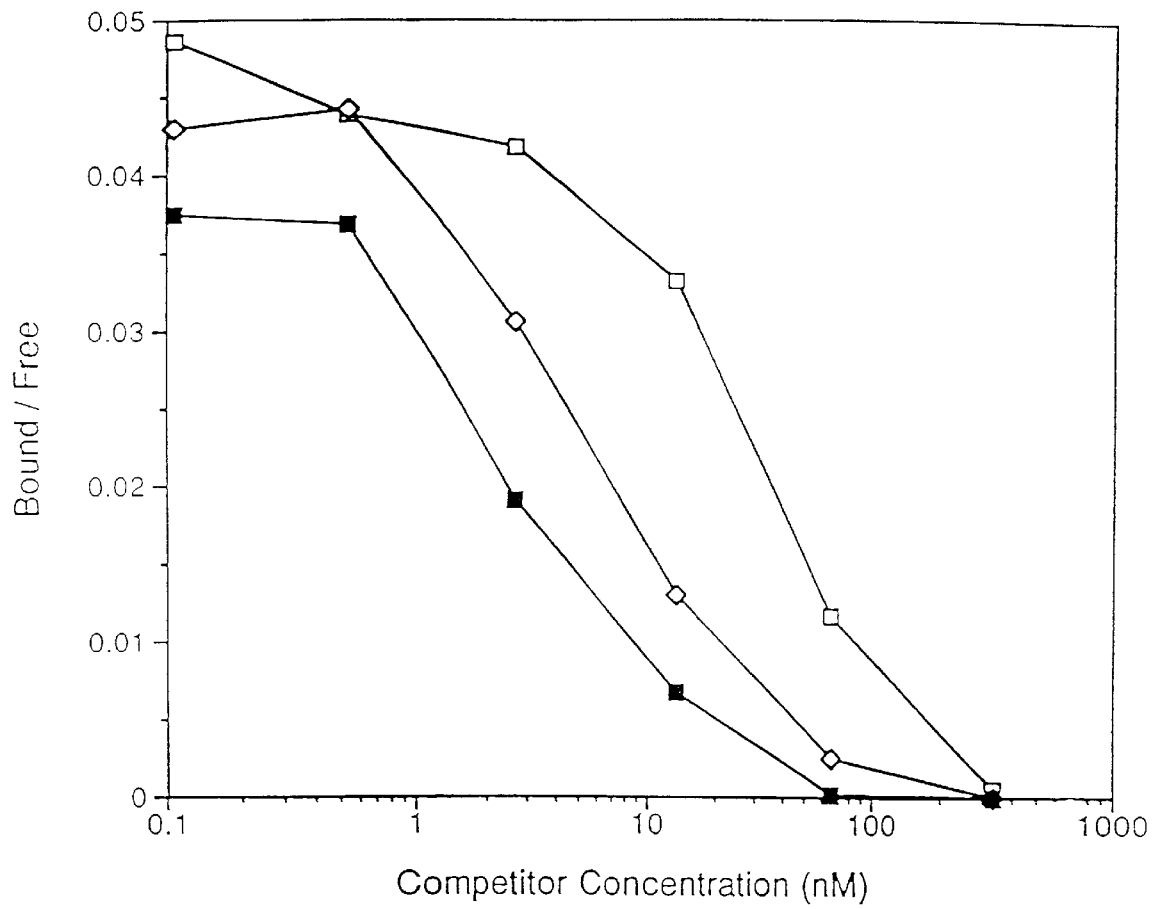
FIG. 11 is a graph depicting competitive binding of muM4TS.11 (closed squares) and HuM4TS.11 (open squares) and HuM4TS.11(gamma 1) (open diamonds). Increasing concentrations of cold competitor antibodies were incubated with the Sp2/0 transfectants expressing PDGF-R β in the presence of radiolabeled tracer muM4TS.11, and the ratio of bound/free radioactivity determined. The results shown are mean values of triplicate samples.

To assess the ability of HuM4TS.11 to compete with the muAb for receptor binding, increasing concentrations of the two antibodies were respectively incubated on ice for one hour with Sp2/0 PDGF-R β transfectant cells and a fixed amount of tracer $^{125}$I-labeled M4TS.11. The sample tubes were processed as in the blocking experiment described. HuM4TS.11 competed less well than muM4TS.11 (FIG. 11). The binding affinities calculated from the data were: $K_a$=5× $10^8 M^{-1}$ for the muAb and $3 \times 10^7 M^{-1}$ for the HuAb.

Figure 12:
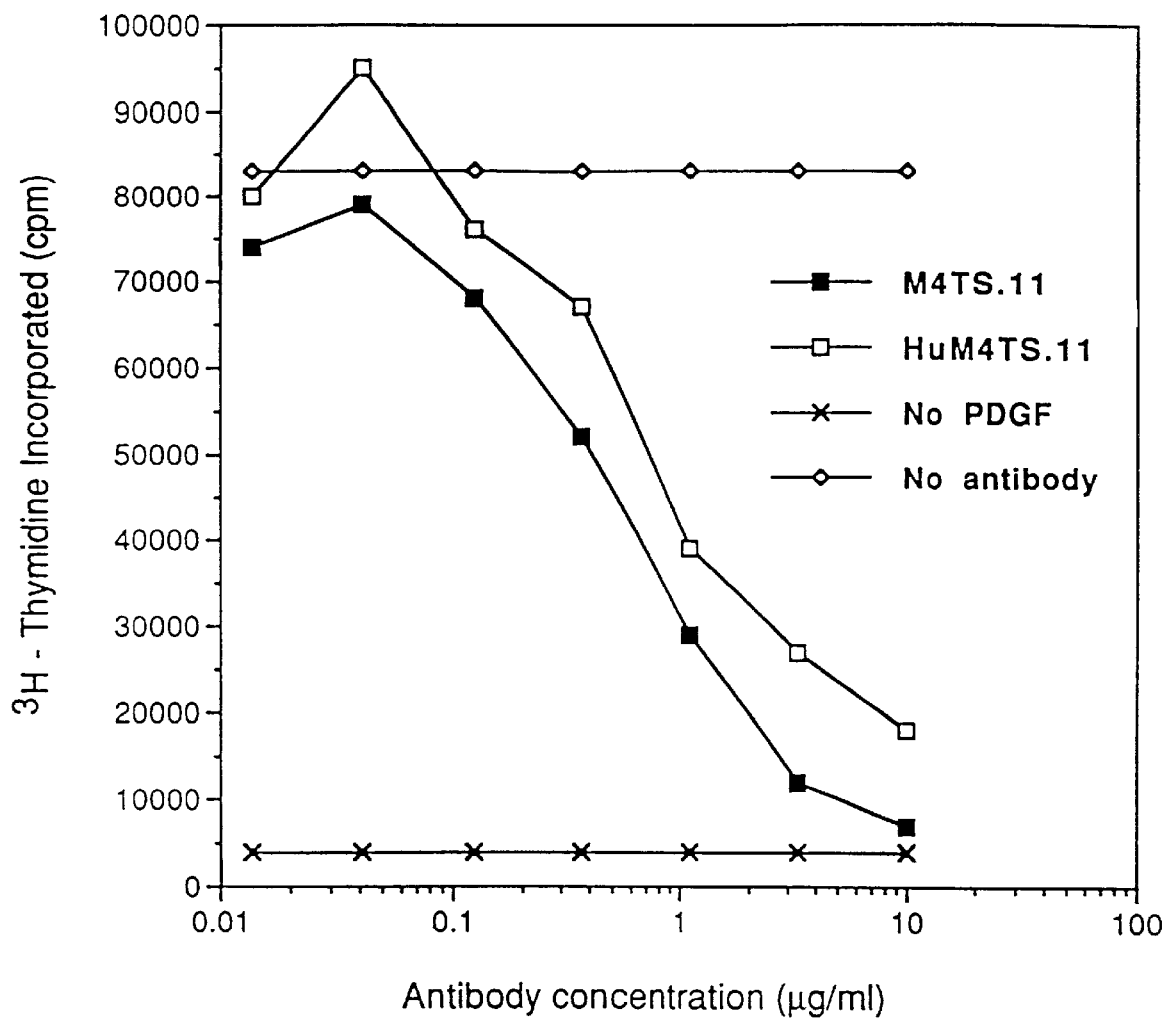
FIG. 12 is a graph depicting inhibition of PDGF-induced proliferation of CHO cell transfectants expressing PDGF-R β (CHO C4) by muM4TS.22 (closed squares) and HuM4TS.22 (open squares). The cells were incubated with increasing concentrations of the indicated antibodies or no antibodies (open diamonds) for 3 hours before 50 ng/ml PDGF BB was added, as described in the text. The results shown are mean values of triplicate samples. The no PDGF BB control is shown by the Xs.

Both muM4TS.11 and HuM4TS.11 were tested for their ability to inhibit PDGF-mediated proliferation of CHO PDGF-R β transfectant cells (CHO C4 line), using the method described above in Example 3. As shown in FIG. 12, incubation of the cells with sufficient concentration of the antibodies almost completely inhibited the stimulation of proliferation by PDGF BB, with muM4TS.11 about two times more effectively than with HuM4TS.11. An irrelevant humanized control antibody had no effect on proliferation (not shown). Thus, HuM4TS.11 inhibited the functional activity of PDGF BB nearly as well as muM4TS.11, although its binding affinity was substantially lower. This may be due to the fact that muM4TS.11 and HuM4TS.11 inhibit PDGF-stimulated proliferation by a mechanism other than competitive inhibition of PDGF binding to its receptor.

EXAMPLE 12

Versions of HuM4TS.11

To determine why HuM4TS.11 has significantly reduced binding affinity relative to muM4TS.11, three additional humanized versions of muM4TS.11 were produced: (1) HuM4TS.11.2, in which a few additional human framework residues were changed to their murine counterparts at positions possibly important to the maintenance of CDR structure, as shown in Table 6 below; (2) HuM4TS.11.3F, a different humanized form of muM4TS.11 in which the human acceptor frameworks are from class III human light and heavy chains instead of the class I chains of antibody III-2R used to make HuM4TS.11, and (3) HuM4TS.11 (gamma1), which has the same variable domains as HuM4TS.11 but has a gamma1 rather than a gamma4 heavy chain constant region. All three antibodies were constructed and produced in the same manner as HuM4TS.11, except the pVg1 expression plasmid (see Co et al. (1992)) was used for HuM4TS.11(gamma1) instead of pVg4. These differences are depicted in Table 5.

TABLE 5

Differences between HuM4TS.11 and HuM4TS.11.2

| Position | HuM4TS.11 | HuM4TS.11.2 |
|---|---|---|
| LC-3 | Q | V |
| LC-4 | M | L |
| LC-69 | S | G |
| HC-38 | R | K |
| HC-40 | A | R |
| HC-70 | I | L |
| HC-81 | M | I |

HuM4TS.11.2 and HuM4TS.11.3F exhibit the same binding characteristics for PDGF-R β and the same level of inhibition of PDGF-stimulated cell proliferation as does HuM4TS.11. However, in a competitive binding experiment, HuM4TS.11 (gamma1) competes within about 3-fold as well as muM4TS.I 1 (FIG. 11), and has a calculated $K_a$ value of $1.6 \times 10^8 M^{-1}$, compared to values of $5 \times 10^8 M^{-1}$ for muM4TS.11 and $3 \times 10^7 M^{-1}$ for HuM4TS.11 given above. Since alterations in the variable domain do not affect binding, but substitution of the gammal constant region for the gamma4 region greatly increases binding affinity, we conclude that the affinity loss of HuM4TS.11 relative to muM4TS.11 is primarily due to its gamma4 isotype. Loss of binding affinity due to the gamma4 isotype has been observed in another antibody (Horgan et al. (1993) J. Immunol. 150:5400), and may be due to structural constraints imposed on the particular antibody by the gamma4 hinge region. See, Horgan et al. (1993).

Although HuM4TS.11(gamma1) has higher binding affinity than HuM4TS.11, these antibodies inhibit PDGF-mediated proliferation of CHO C4 cells about equally well, i.e., have equal biological activity in that assay (data not shown). Hence HuM4TS.11 and HuM4TS.11 (gamma1) will each be useful, depending on whether reduced effector function or high binding affinity is respectively desired. Likewise, versions of HuM4TS.11 with the gamma2 and gamma3 isotypes will be useful; for example HuM4TS.11 (gamma2) should have minimal effector function like HuM4TS.11 but higher binding affinity like HuM4TS (gamma1).

EXAMPLE 13

Epitope Mapping of muM4TS.11, muM4TS.22 and their Humanized Versions

Figure 13A:
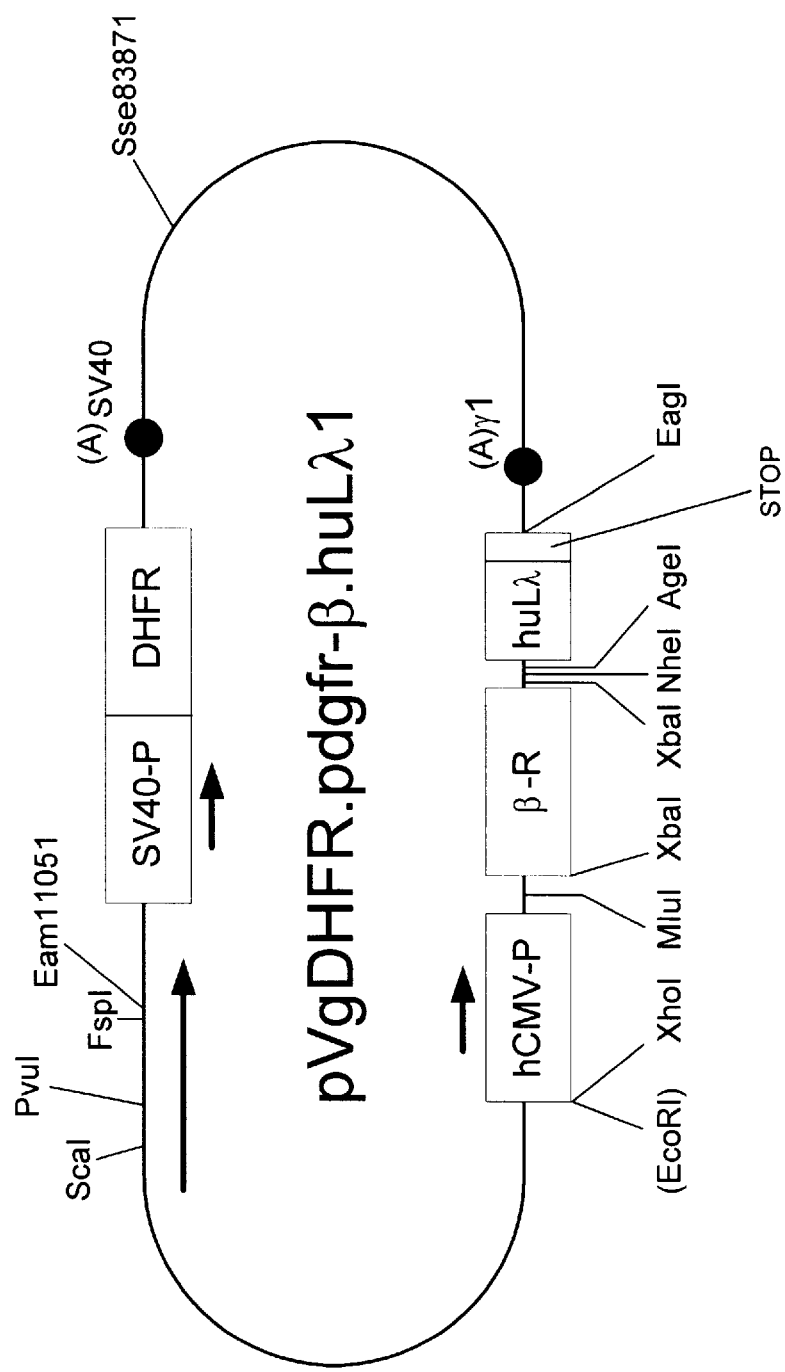
FIG. 13 is a schematic diagram of expression plasmid (A) and PDGF-R β deletion constructs. In (A), hCMV-P is a promoter region from human CMV, β-R is the position where the PDGF-R β deletion construct was inserted, HuLλ1 is the constant region of the human lambda-1 antibody gene, and DHFR is the dihydrofolate reductase gene. In (B), the five extracellular Ig-like domains of PDGF-R β are denoted ED1–ED5, TM is the transmembrane domain, and ID is the intracellular domain. The diagrams in (B) represent, from top to bottom, the entire PDGF-R β and the deletion fusion proteins D1–5, D1–4, D1–3, D1–2, D1 and D5.
Figure 13B:
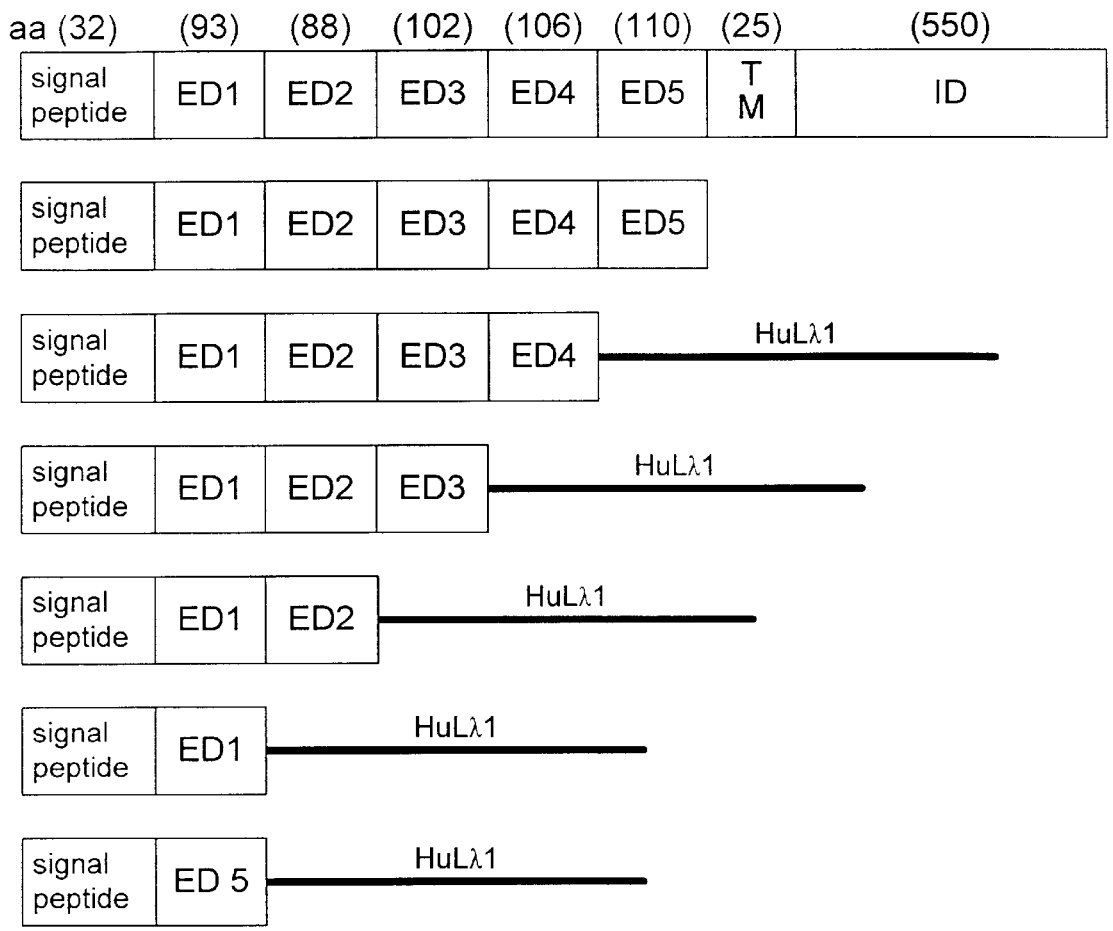
Figure 14A:
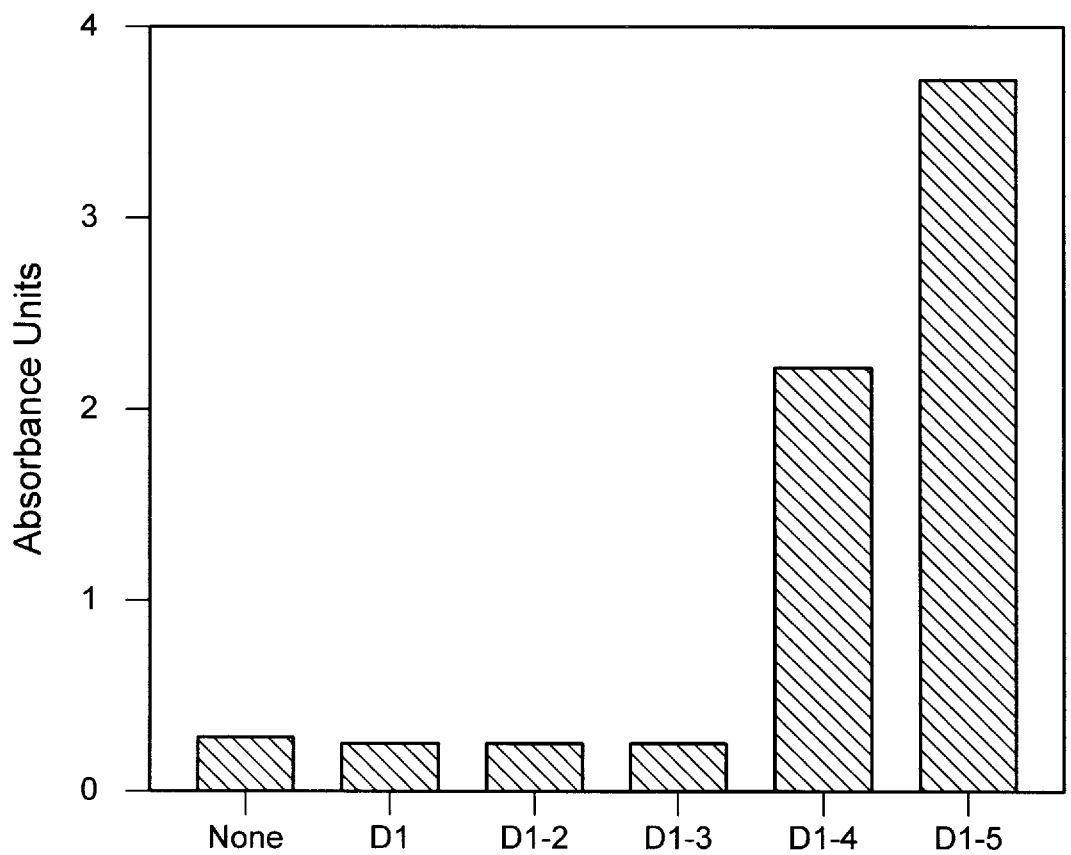
FIG. 14A shows the results obtained with muM4TS.11.
Figure 14B:
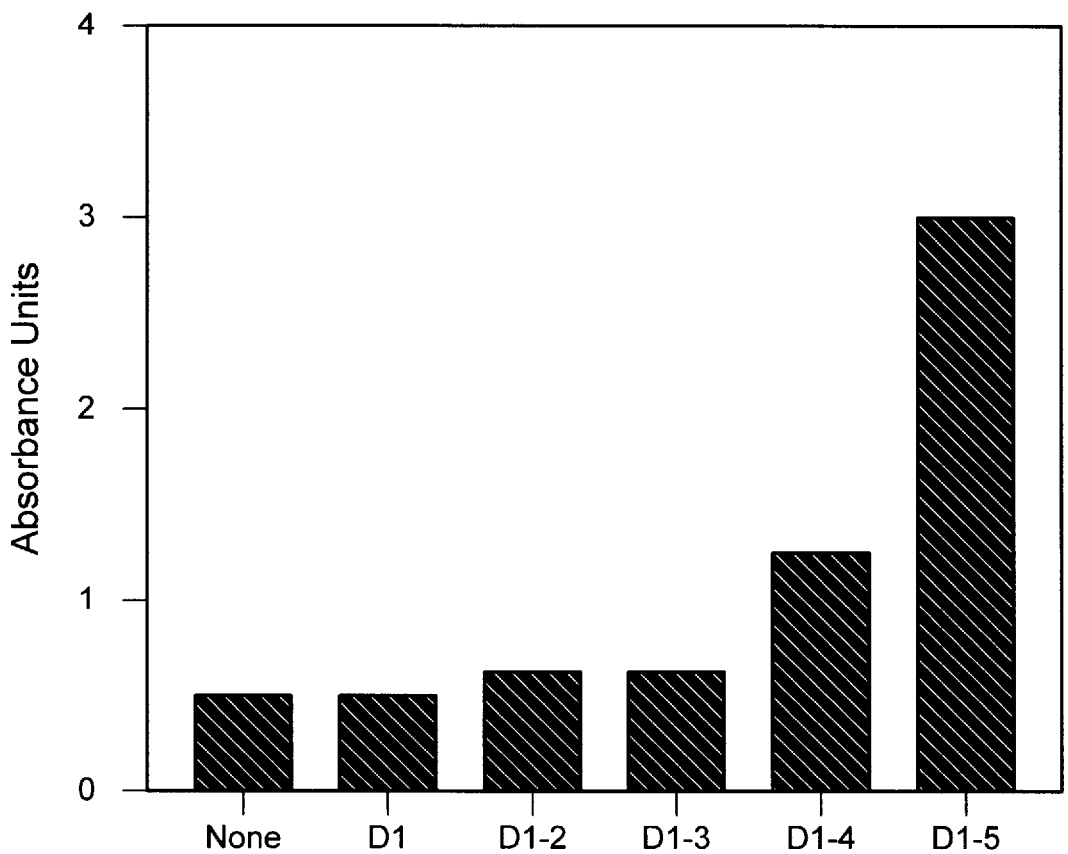
FIG. 14B shows the results obtained with HuM4TS.11.
Figure 14C:
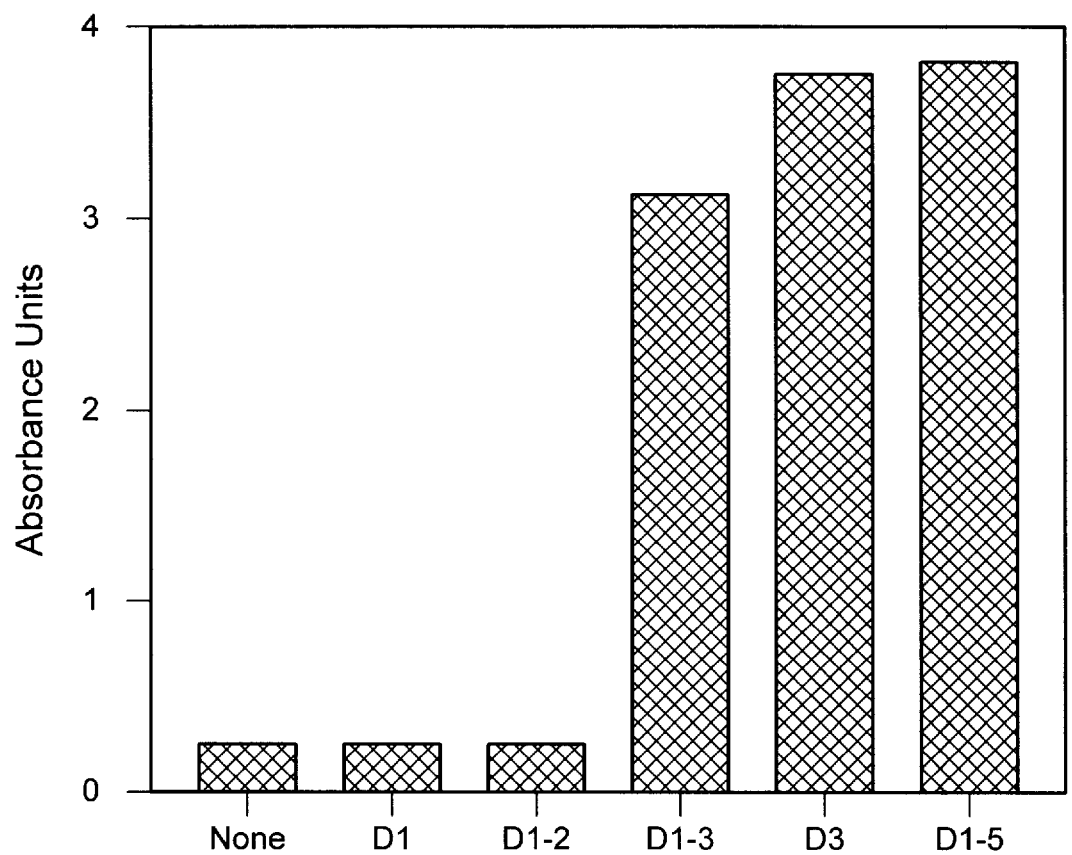
FIG. 14C shows the results obtained with muM4TS.22.
Figure 14D:
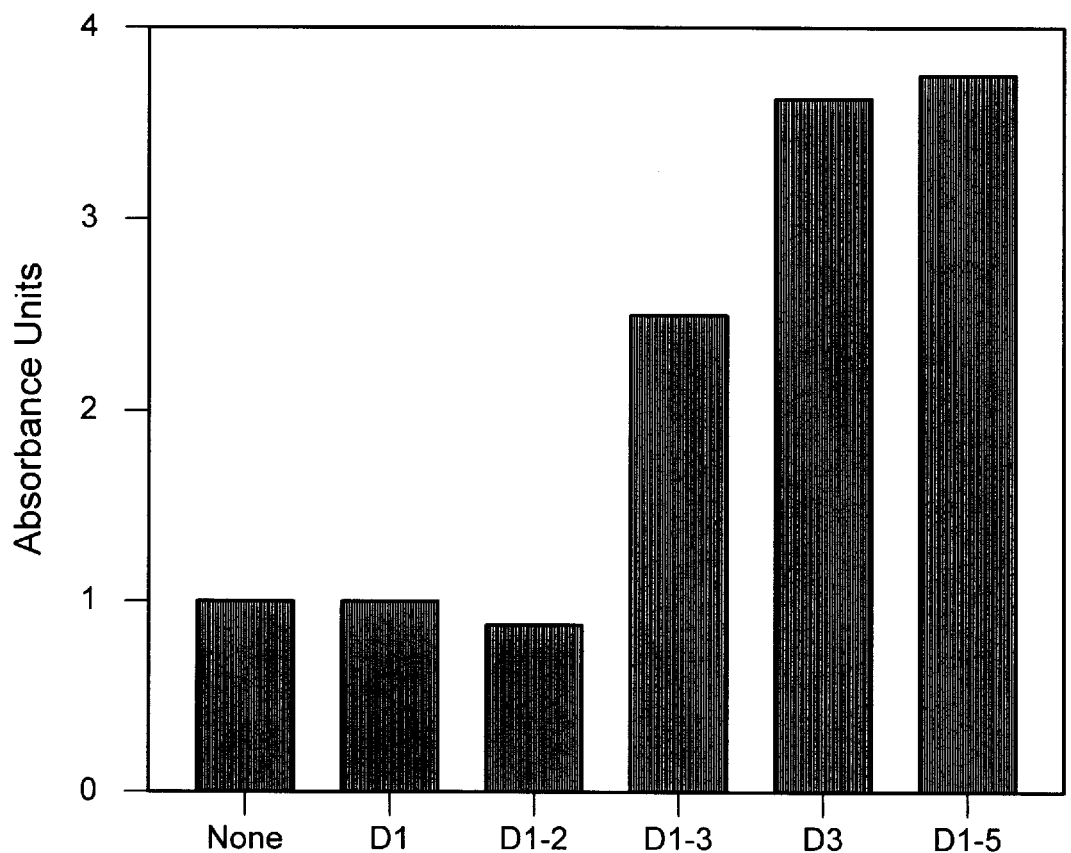
FIG. 14D shows the results obtained with HuM4TS.22.

To localize the binding sites of the M4TS antibodies on the PDGF-R, a series of PDGF-R β deletion mutants, each consisting of one or more adjacent domains of the extracellular portion of the receptor, was constructed by standard methods including PCR. The deletion constructs were each cloned into an expression plasmid (FIG. 13A) where they were fused to the constant region of the human lambda-1 immunoglobulin light chain, to facilitate detection in ELISA. The constructs were as follows (see FIG. 13B):

D1: Domain 1+lambda constant region
D1–2: Domains 1–2+lambda constant region
D1–3: Domains 1–3+lambda constant region
D1–4: Domains 1–4+lambda constant region
D5: Domain 5+lambda constant region
D3: Domain 3+lambda constant region These PDGF-R β deletion fusion proteins were transiently expressed, by transfecting 10 μg of the respective expression plasmids into approximately $10^7$ S194 mouse myeloma cells (ATCC TIB 19) using the DEAE-dextran method in accordance with the method described by Queen et al. (1984) Mol. Cell. Biol. 4:1042. After the transfected cells had died (4–5 days) and been removed by centrifugation, the culture supernatants containing the PDGF-R β deletion proteins were used in ELISA assays, 100 μl/well. First, the relative levels of the various PDGF-R β deletion proteins were measured in an ELISA where the plate was coated with goat anti-human lambda antibody (Tago) and the proteins detected with HRP-conjugated goat anti-human lambda antibody. In the experiment whose results are shown in FIG. 14, the deletion proteins D1, D1–2, D1–3, D1–4 and D3 were all expressed at comparable levels. To determine the ability of the antibodies to bind to each deletion protein, an ELISA was performed in which goat anti-human lambda antibody was used to coat the plate, followed by the cell supernatant and then 0.1 μg of the appropriate antibody, and then bound antibody detected with HRP-conjugated goat-anti-mouse Ig or goat-anti-human Ig antibody as appropriate (Tago). As a positive control, purified soluble PDGF-R β (Example 1) was coated directly on certain wells of the plate (denoted D1–5 in FIG. 14).

The results of this experiment (FIG. 14) show that muM4TS.11 and HuM4TS.11 do not bind to deletion proteins containing only the first through third domains of PDGF-R β, but do bind to protein D1–4 containing the fourth domain, showing that the binding epitope is in the fourth domain. MuM4TS.22 and HuM4TS.22 do not bind to deletion proteins containing only the first through second domains of PDGF-R β, but do bind to protein D1–3 containing the third domain, showing that the binding epitope is in the third domain. This is confirmed by the fact that muM4TS.22 and HuM4TS.22 bind to the protein D3 (FIG. 14) containing only the third domain. In a separate experiment, the protein D5 containing only the fifth domain was similarly expressed by transient transfection, and none of muM4TS.11 and HuM4TS.11, muM4TS.22 and HuM4TS.22 bound to it in an ELISA, so their epitopes do not involve that domain.

EXAMPLE 14
Inhibition of Restenosis After Vascular Injury in Rats

To determine whether muM4TS.11 inhibits PDGF-mediated proliferation of rat cells in vitro, the following experiment was performed. Rat aortic smooth muscle cells (SMC) were plated at a 1:3 split ratio in 10% FCS and made quiescent 24 hours later by changing the medium to 1% control process serum replacement II (Sigma, St. Louis, Mo.). Three to five days later, the cells were stimulated with PDGF BB (10 ng/ml). At the time of stimulation, increasing doses of the specific MAb or mouse IgG (control) were added. Cell proliferation was determined by measuring $^3$H-thymidine incorporated into DNA when the cells were pulsed from 19 to 26 hr after stimulation. MuM4TS.11 inhibited proliferation in a concentration-dependent manner with an $IC_{50}$ of about 0.5 μg/ml. These results also imply that muM4TS.11 binds to the rat PDGF-R β, and rats may be used for in vivo experiments with the antibody.

In preliminary experiments to determine the pharmacokinetics of muM4TS.11 in rats, an initial dose of antibody was injected and blood samples obtained at 1, 2, 3, 6, 12, 24, 36, and 48 hr. Antibody levels in plasma were measured by ELISA. The half-life of the antibody in rats was approximately 1 day. Based on these results, it was decided to treat the animals with a "high-dose" regimen of a 4 mg bolus of muM4TS.11 prior to vascular injury, followed by 2 mg IV every 24 hr for 4 days. This dosage regimen was sufficient to maintain a level of antibody in the rats significantly higher than the concentration determined above to inhibit PDGF-mediated proliferation of rat SMC in vitro for at least 7 days, which exceeds the time period of maximal SMC proliferation after vascular injury found in previous experiments. (In humans, proportionally smaller and less frequent doses are likely to be sufficient for a humanized anti-PDGF-R β antibody such as HuM4TS.11 or HuM4TS.22 to be effective, because of the expected longer half-life in humans and higher affinity for human PDGF-R β of these non-immunogenic HuAbs).

To perform the vascular injury, under sterile conditions and after general anesthesia the left common carotid arteries of S-D rats were exposed. Anesthesia was induced with ketamine and xilaxine by IP injection. Additional anesthesia was given at half a dose every forty-five minutes. Through a midline neck incision the left common, external and internal carotid arteries were exposed. A 2F Fogarty balloon catheter was introduced in the left external carotid artery. The balloon was inflated sufficiently to generate slight resistance and withdrawn 3 times to consistently produce endothelial denudation of the entire length of the left common carotid artery (LCCA), thus simulating vascular injury after balloon angioplasty in human patients. Upon removal of the catheter, the left external carotid artery was ligated with 3.0 silk. The skin was closed with surgical wound clips.

In this model, the rats were sacrificed 21 days after the balloon injury. At the time of sacrifice, the rats were first anesthetized. Via a medline abdominal incision the distal abdominal aorta was exposed and through an 18 gauge IV catheter introduced above the aortic bifurcation, the aorta was flushed with 50 cc of lactated Ringer's Solution at 120 mm Hg followed by in vivo fixation with 200 ml 4% paraformaldehyde solution infused over 5 min at 120 mm Hg. Once the perfusion was started, the animals were sacrificed with an overdose of pentothal via the IV catheter. After 5 min of perfusion-fixation the entire right and left carotid arteries were retrieved, including the aortic arch, innominate artery and carotid bifurcation. The arteries were further fixed by immersion in the same fixative used for perfusion.

Figure 15:
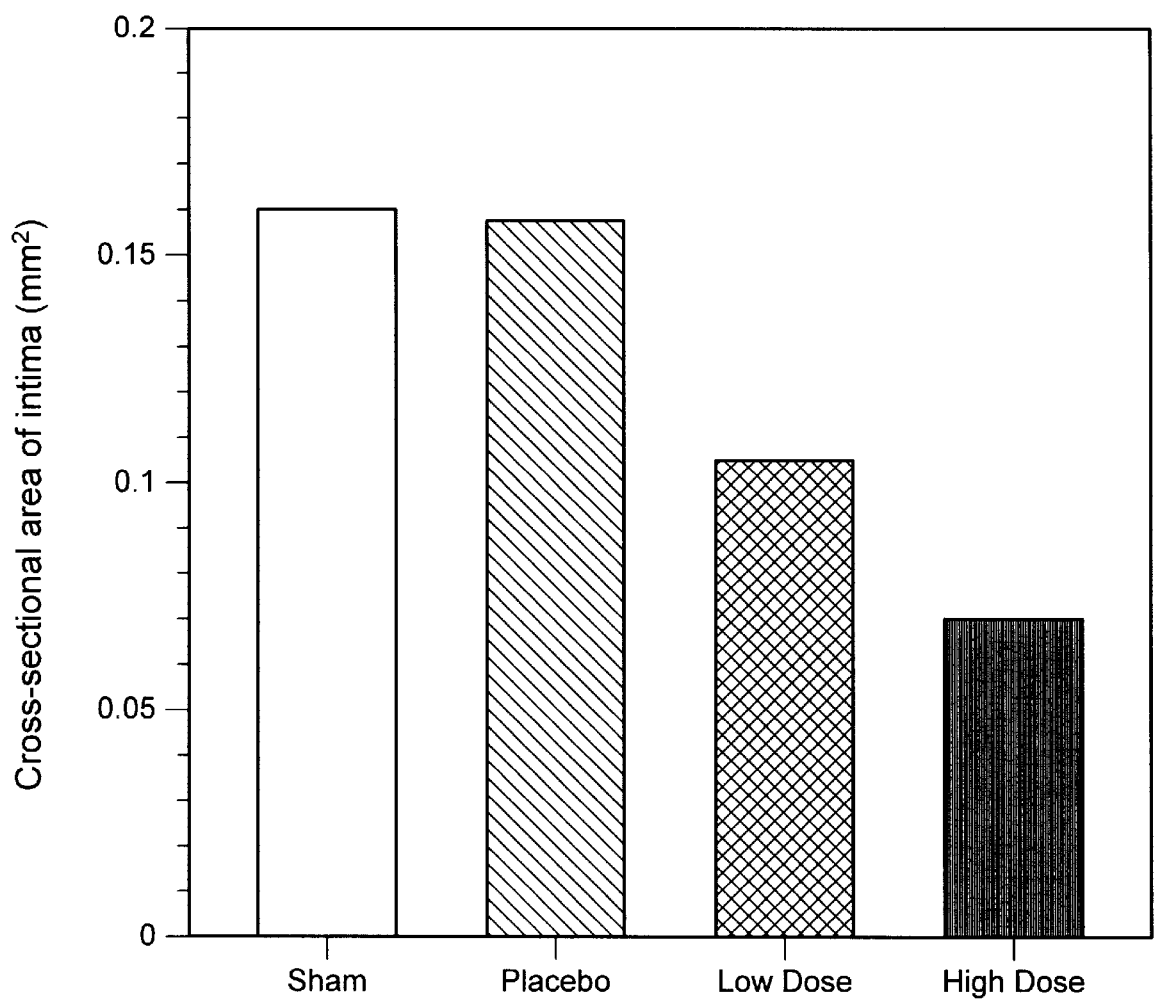
FIG. 15 is a bar graph depicting the mean cross-sectional areas of intima of arteries of groups of rats subjected to balloon injury and given the indicated treatment regimen.

For measurement of intimal thickening, the left common carotid arteries were sectioned every 3 mm, from the proximal to the distal end. The segments were immersed in paraffin, sectioned, mounted in glass slides and stained with hematoxilin and eosin and elastin stain. Cross-sectional areas for lumen, intima and media of the artery were determined as a mean of the 3 segments with the greatest intimal thickness. Morphometric analysis was performed by an observer blinded to drug regimen using an automated image analysis system with a computerized digital microscopic planimetry algorithm (Bioquant program). Differences between placebo or control groups and treated groups were analyzed for statistical significance by analysis of variance and a two-tailed, unpaired Student's t test Four groups of rats underwent carotid balloon injury as explained above (FIG. 15). One group (n=10) received the high-dose of muM4TS.11 described above, and a second group (n=9) received a low-dose regimen equal to 10% of the high-dose regimen. A placebo group (n=7) received the high-dose amount of non-specific mouse IgG, and a "sham" control group (n=7) received no specific treatment after injury. The high dose muM4TS.11 group had approximately 60% less thickening of the artery intima than the placebo or control groups and the low dose group had approximately 40% less, which are highly statistically significant results (p=0.0001). There was no significant thickening of the outer part of the artery wall, the media. Hence, muM4TS.11 strongly and specifically inhibited thickening of the inner part of the artery wall (intimal hyperplasia), the measure of restenosis, after injury with a balloon catheter simulating angioplasty.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

What is claimed is:

1. An antibody that specifically binds to the PDGF beta receptor not within the fifth extracellular Ig-like domain, wherein the antibody inhibits PDGF BB-induced proliferation of a cell expressing the PDGF beta receptor, and where the inhibition is greater than 80% achieved at an antibody concentration of 10 µg/ml.

2. The antibody according to claim 1, wherein the antibody inhibits binding of PDGF BB to a cell expressing the PDGF beta receptor.

3. The antibody according to claim 1, wherein the antibody binds to the third extracellular Ig-like domain of the PDGF beta receptor.

4. The antibody according to claim 2, wherein the antibody is humanized.

5. A humanized antibody that specifically binds to the PDGF beta receptor not within the fifth extracellular Ig-like domain, wherein the antibody inhibits PDGF BB-induced proliferation of a cell expressing the PDGF beta receptor, and where the inhibition is greater than 80% achieved at an antibody concentration of 10 µg/ml and wherein the antibody comprises a light chain variable region which has the mature amino acid sequence of SEQ ID NO:6 and a heavy chain variable region which has the mature amino acid sequence of SEQ ID NO:8.

6. The antibody according to claim 5, wherein the antibody is HuM4TS.22.

7. An antibody that specifically binds to the PDGF beta receptor not within the fifth extracellular Ig-like domain, wherein the antibody inhibits PDGF BB-induced proliferation of a cell expressing the PDGF beta receptor, and where the inhibition is greater than 80% achieved at an antibody concentration of 10 µg/ml and wherein the antibody does not inhibit binding of PDGF BB to a cell expressing the PDGF beta receptor.

8. The antibody according to claim 1, wherein the antibody binds to the fourth extracellular Ig-like domain of the PDGF beta receptor.

9. The antibody according to claim 7, wherein the antibody is humanized.

10. A humanized antibody that specifically binds to the PDGF beta receptor not within the fifth extracellular Ig-like domain, wherein the antibody inhibits PDGF BB-induced proliferation of a cell expressing the PDGF beta receptor, and where the inhibition is greater than 80% achieved at an antibody concentration of 10 µg/ml and wherein the antibody comprises a light chain variable region which has the mature amino acid sequence of SEQ ID NO:14 and a heavy chain variable region which has the mature amino acid sequence of SEQ ID NO:16.

11. The antibody according to claim 10, wherein the antibody is HuM4TS.22.

12. A composition comprising any of the antibodies of claims 1, 2, 3, 4, 5, 6, 7, 8, 9, 10, or 11 and a pharmaceutically acceptable excipient.

13. The composition according to claim 12, further comprising a graft or stent coated with the composition.

\* \* \* \* \*

UNITED STATES PATENT AND TRADEMARK OFFICE
CERTIFICATE OF CORRECTION

PATENT NO. : 5,882,644

DATED : March 16, 1999

INVENTOR(S) : Chung N. CHANG, Nicholas F. LANDOLFI, and Ulrich MARTIN

It is certified that error appears in the above-identified patent and that said Letters Patent is hereby corrected as shown below:

At Column 6, line, 5, delete "Inuunol." and insert --Immunol.--.

At Column 23, line 58, delete "mg/mil" and insert --mg/ml--.

At Column 26, line 11, delete "and (4) the flanking two flanking" and insert --and (4) the final two flanking--.

At Column 26, line 22, delete "BamnHI" and insert --BamHI--.

At Column 27, line 65, delete "muM4TS.I1" and insert --muM4TS.11--.

Signed and Sealed this

Twenty-seventh Day of July, 1999

Attest:

Q. TODD DICKINSON

*Attesting Officer*     *Acting Commissioner of Patents and Trademarks*